(12) United States Patent
Mazanec

(10) Patent No.: US 12,318,607 B2
(45) Date of Patent: Jun. 3, 2025

(54) IMPLANTABLE COCHLEAR SYSTEM WITH INTEGRATED COMPONENTS AND LEAD CHARACTERIZATION

(71) Applicant: Envoy Medical Corporation, White Bear Lake, MN (US)

(72) Inventor: Paul R. Mazanec, Ham Lake, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 0 days.

(21) Appl. No.: 18/310,307

(22) Filed: May 1, 2023

(65) Prior Publication Data

US 2023/0264016 A1 Aug. 24, 2023

Related U.S. Application Data

(62) Division of application No. 16/797,392, filed on Feb. 21, 2020, now Pat. No. 11,672,970.
(Continued)

(51) Int. Cl.
*A61N 1/05* (2006.01)
*A61N 1/02* (2006.01)
(Continued)

(52) U.S. Cl.
CPC ........... *A61N 1/0541* (2013.01); *A61N 1/025* (2013.01); *A61N 1/0488* (2013.01); *A61N 1/08* (2013.01);
(Continued)

(58) Field of Classification Search
None
See application file for complete search history.

(56) References Cited

U.S. PATENT DOCUMENTS 2,827,041 A 3/1958 Pierson
4,400,590 A 8/1983 Michelson
(Continued)

FOREIGN PATENT DOCUMENTS

CN 104394930 A 3/2015
CN 110086237 A 8/2019
(Continued)

OTHER PUBLICATIONS

European Patent Application No. 20759643.8, European Search Report dated Oct. 5, 2022, 11 pages.
(Continued)

*Primary Examiner* — Erica S Lee
(74) *Attorney, Agent, or Firm* — Fredrikson & Byron, P.A.

(57) ABSTRACT

Cochlear implant systems can include a cochlear electrode, a stimulator in electrical communication with the cochlear electrode, a sensor configured to receive a stimulus signal and generate an input signal based on the received stimulus signal, and a signal processor in communication with the stimulator and the sensor. The signal processor can include an analog filtering stage configured to generate an analog filtered signal from a received input signal and a digital filtering stage configured to generate a digitally filtered signal from the analog filtered signal. The analog filtering stage and digital filtering stage can be used to normalize the frequency response of the digitally filtered signal with respect to the stimulus signal.

16 Claims, 27 Drawing Sheets

Related U.S. Application Data

(60) Provisional application No. 62/808,634, filed on Feb. 21, 2019.

(51) Int. Cl.

| | | |
|---|---|---|
| *A61N 1/04* | (2006.01) | |
| *A61N 1/08* | (2006.01) | |
| *A61N 1/36* | (2006.01) | |
| *A61N 1/372* | (2006.01) | |
| *A61N 1/378* | (2006.01) | |
| *G16H 40/67* | (2018.01) | |
| *H04W 4/80* | (2018.01) | |
| *H04W 12/50* | (2021.01) | |

(52) U.S. Cl.
CPC ..... *A61N 1/36038* (2017.08); *A61N 1/36039* (2017.08); *A61N 1/36171* (2013.01); *A61N 1/37217* (2013.01); *A61N 1/37235* (2013.01); *A61N 1/37241* (2013.01); *A61N 1/37247* (2013.01); *A61N 1/37258* (2013.01); *A61N 1/37282* (2013.01); *A61N 1/378* (2013.01); *G16H 40/67* (2018.01); *H04W 4/80* (2018.02); *H04W 12/50* (2021.01)

(56) References Cited

U.S. PATENT DOCUMENTS

| | | | |
|---|---|---|---|
| 4,495,384 A | 1/1985 | Scott et al. | |
| 4,729,366 A | 3/1988 | Schaefer | |
| 4,850,962 A | 7/1989 | Schaefer | |
| 4,918,745 A | 4/1990 | Hutchison | |
| 5,540,095 A | 7/1996 | Sherman et al. | |
| 5,755,742 A | 5/1998 | Schuelke et al. | |
| 5,762,583 A | 6/1998 | Adams et al. | |
| 6,195,585 B1 | 2/2001 | Karunasiri et al. | |
| 6,212,431 B1 | 4/2001 | Hahn et al. | |
| 6,259,951 B1 | 7/2001 | Kuzma et al. | |
| 6,272,382 B1 | 8/2001 | Faltys et al. | |
| 6,308,101 B1 | 10/2001 | Faltys et al. | |
| 6,358,281 B1 | 3/2002 | Berrang et al. | |
| 6,391,024 B1 | 5/2002 | Sun et al. | |
| 7,225,028 B2 | 5/2007 | Della Santina et al. | |
| 7,319,906 B2 | 1/2008 | Kuzma et al. | |
| 7,376,563 B2 | 5/2008 | Leysieffer et al. | |
| 7,524,278 B2 | 4/2009 | Madsen et al. | |
| 7,729,775 B1 | 6/2010 | Saoji et al. | |
| 7,864,968 B2 | 1/2011 | Kulkarni et al. | |
| 8,554,329 B1 | 10/2013 | Mann et al. | |
| 8,626,308 B2 | 1/2014 | Meskens | |
| 8,655,449 B2 | 2/2014 | Haller et al. | |
| 8,954,158 B2 | 2/2015 | Smith | |
| 9,061,140 B2 | 6/2015 | Shi et al. | |
| 9,205,272 B2 | 12/2015 | Suaning et al. | |
| 9,504,076 B2 | 11/2016 | El-Hoiydi et al. | |
| 9,539,430 B2 | 1/2017 | Mishra et al. | |
| 9,693,155 B2 | 6/2017 | Meister et al. | |
| 9,716,952 B2 | 7/2017 | Mauger | |
| 9,999,770 B2 | 6/2018 | Walravens et al. | |
| 11,324,958 B2 | 5/2022 | Anderson et al. | |
| 2002/0015506 A1* | 2/2002 | Aceti | H04R 25/70 381/317 |
| 2002/0039425 A1 | 4/2002 | Burnett et al. | |
| 2002/0099421 A1 | 7/2002 | Goldsmith et al. | |
| 2004/0230254 A1 | 11/2004 | Harrison et al. | |
| 2005/0033384 A1 | 2/2005 | Sacha | |
| 2005/0197677 A1 | 9/2005 | Stevenson | |
| 2006/0122664 A1 | 6/2006 | Sacha et al. | |
| 2006/0183965 A1 | 8/2006 | Kasic et al. | |
| 2008/0195179 A1 | 8/2008 | Quick | |
| 2008/0300658 A1 | 12/2008 | Meskens | |
| 2009/0018616 A1 | 1/2009 | Quick et al. | |
| 2009/0082831 A1 | 3/2009 | Paul et al. | |
| 2009/0171421 A1 | 7/2009 | Atalar et al. | |
| 2009/0187233 A1 | 7/2009 | Stracener | |
| 2009/0192565 A1 | 7/2009 | Lee et al. | |
| 2010/0010582 A1 | 1/2010 | Carbunaru et al. | |
| 2010/0030012 A1 | 2/2010 | Meskens | |
| 2010/0042183 A1 | 2/2010 | Beck | |
| 2010/0317913 A1 | 12/2010 | Conn et al. | |
| 2011/0066210 A1 | 3/2011 | Wilson | |
| 2011/0082521 A1 | 4/2011 | Botros et al. | |
| 2011/0098785 A1 | 4/2011 | Mishra | |
| 2011/0116669 A1 | 5/2011 | Karunasiri | |
| 2011/0137180 A1 | 6/2011 | Johnson et al. | |
| 2011/0144719 A1 | 6/2011 | Perkins et al. | |
| 2011/0160808 A1 | 6/2011 | Lyden et al. | |
| 2011/0280426 A1 | 11/2011 | Bachler | |
| 2011/0295331 A1 | 12/2011 | Wells et al. | |
| 2012/0063610 A1 | 3/2012 | Kaulberg et al. | |
| 2012/0215285 A1 | 8/2012 | Tahmasian et al. | |
| 2012/0277835 A1 | 11/2012 | Della Santina et al. | |
| 2013/0018216 A1 | 1/2013 | Beckerle et al. | |
| 2013/0023953 A1 | 1/2013 | Van Den Honert | |
| 2013/0193914 A1 | 8/2013 | Gaddam et al. | |
| 2013/0197613 A1 | 8/2013 | Kelly et al. | |
| 2013/0223664 A1 | 8/2013 | Meskens et al. | |
| 2013/0238055 A1 | 9/2013 | Marnfeldt et al. | |
| 2013/0268025 A1 | 10/2013 | Ranu | |
| 2013/0278226 A1 | 10/2013 | Cong et al. | |
| 2013/0317584 A1 | 11/2013 | Stevenson et al. | |
| 2014/0058482 A1 | 2/2014 | Gupta et al. | |
| 2014/0070761 A1 | 3/2014 | Labbe et al. | |
| 2014/0155947 A1 | 6/2014 | Kroll et al. | |
| 2014/0247954 A1* | 9/2014 | Hall | H04R 17/02 381/92 |
| 2014/0270211 A1* | 9/2014 | Solum | H04R 25/30 381/60 |
| 2014/0275730 A1 | 9/2014 | Lievens et al. | |
| 2014/0309712 A1 | 10/2014 | Masaki et al. | |
| 2014/0350652 A1 | 11/2014 | Suwito | |
| 2015/0125012 A1 | 5/2015 | Sabin | |
| 2015/0174416 A1 | 6/2015 | Angara et al. | |
| 2015/0224312 A1 | 8/2015 | Platz et al. | |
| 2015/0256945 A1 | 9/2015 | Mazanec | |
| 2015/0374988 A1 | 12/2015 | Laudanski | |
| 2015/0375003 A1 | 12/2015 | Meskens | |
| 2016/0050500 A1 | 2/2016 | Liao et al. | |
| 2016/0227333 A1 | 8/2016 | Babico | |
| 2016/0287870 A1* | 10/2016 | Yip | A61N 1/36038 |
| 2017/0043162 A1 | 2/2017 | Lopez-Poveda | |
| 2017/0077938 A1 | 3/2017 | Heubi | |
| 2017/0094396 A1 | 3/2017 | Chandramohan et al. | |
| 2017/0161449 A1 | 6/2017 | Meskens | |
| 2017/0259072 A1 | 9/2017 | Newham et al. | |
| 2017/0360364 A1 | 12/2017 | Heasman et al. | |
| 2018/0028811 A1 | 2/2018 | Van Gerwen et al. | |
| 2018/0028827 A1 | 2/2018 | Schilling et al. | |
| 2018/0041848 A1 | 2/2018 | Nielsen et al. | |
| 2018/0050197 A1 | 2/2018 | Mazanec et al. | |
| 2018/0050198 A1 | 2/2018 | Mazanec et al. | |
| 2018/0050203 A1 | 2/2018 | Mazanec et al. | |
| 2018/0059870 A1 | 3/2018 | Krah | |
| 2018/0264269 A1 | 9/2018 | Meadows | |
| 2018/0317027 A1 | 11/2018 | Bolner et al. | |
| 2018/0333577 A1 | 11/2018 | Nygard et al. | |
| 2018/0361151 A1 | 12/2018 | Ridler et al. | |
| 2019/0045308 A1 | 2/2019 | Chen et al. | |
| 2019/0046116 A1 | 2/2019 | Shah et al. | |
| 2019/0190296 A1 | 6/2019 | Paralikar et al. | |
| 2019/0217101 A1 | 7/2019 | Shi et al. | |
| 2019/0231203 A1 | 8/2019 | Harczos | |
| 2019/0344073 A1 | 11/2019 | Baker et al. | |
| 2019/0358450 A1 | 11/2019 | Lo et al. | |
| 2020/0054877 A1 | 2/2020 | Calixto et al. | |
| 2021/0084417 A1 | 3/2021 | Bagazov et al. | |
| 2021/0121707 A1 | 4/2021 | Fried et al. | |
| 2021/0135704 A1 | 5/2021 | El-Hoiydi et al. | |
| 2021/0187293 A1 | 6/2021 | Friedling | |
| 2021/0361194 A1 | 11/2021 | Arab et al. | |

(56) References Cited

U.S. PATENT DOCUMENTS

| | | |
|---|---|---|
| 2022/0203104 A1 | 6/2022 | Hernandez et al. |
| 2022/0339445 A1 | 10/2022 | Litvak et al. |

FOREIGN PATENT DOCUMENTS

| | | |
|---|---|---|
| DE | 4419070 A1 | 12/1994 |
| DE | 60107062 T2 | 12/2004 |
| DE | 102013214049 B4 | 3/2015 |
| EP | 1043914 A2 | 10/2000 |
| EP | 1683544 B1 | 11/2010 |
| EP | 2884766 B1 | 2/2018 |
| EP | 3120579 B1 | 2/2020 |
| JP | 2016024111 A | 2/2016 |
| TW | 201142830 A | 12/2011 |
| WO | 2007137032 A2 | 11/2007 |
| WO | 2010056768 A1 | 5/2010 |
| WO | 2014037888 A1 | 3/2014 |
| WO | 2014054215 A1 | 4/2014 |
| WO | 2015077773 A1 | 5/2015 |
| WO | 2016122606 A1 | 8/2016 |
| WO | 2017100866 A1 | 6/2017 |
| WO | 2018035329 A1 | 2/2018 |
| WO | 2018144732 A1 | 8/2018 |

OTHER PUBLICATIONS

International Patent Application No. PCT/US2020/019166, International Search Report and Written Opinion mailed Jul. 28, 2020, 33 pages.

Yip et al. "A Fully-Implantable Cochlear Implant SoC With Piezoelectric Middle-Ear Sensor and Arbitrary Waveform Neural Stimulation" IEEE J Solid-State Circuits. Author Manuscript; Available in PMC Jan. 1, 2016, pp. 36.

* cited by examiner

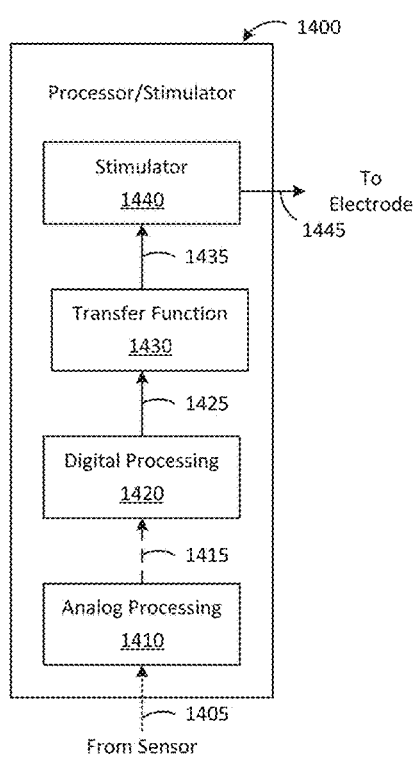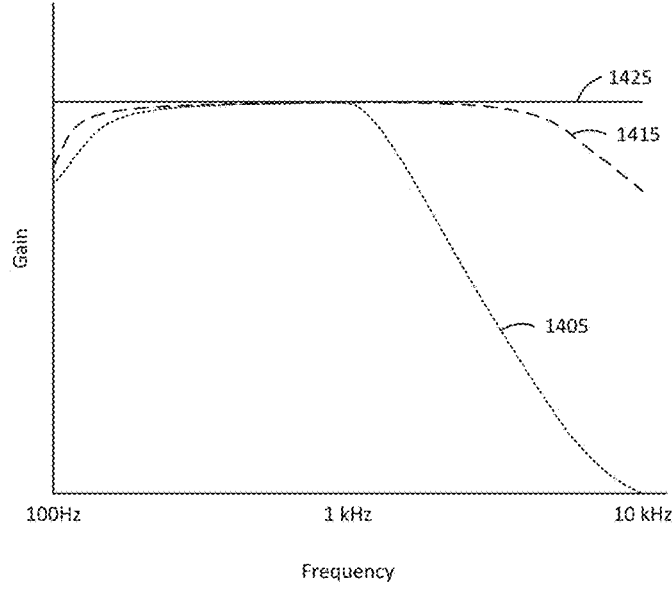
FIG. 14A
FIG. 14B

|  | Simulated Transfer Function 1 | Simulated Transfer Function 2 | Simulated Transfer Function 3 | ... | Simulated Transfer Function m |
|---|---|---|---|---|---|
| Sound 1 | Stimulation Signal (1,1) | Stimulation Signal (1,2) | Stimulation Signal (1,3) | ... | Stimulation Signal (1,m) |
| Sound 2 | Stimulation Signal (2,1) | Stimulation Signal (2,2) | Stimulation Signal (2,3) | ... | Stimulation Signal (2,m) |
| Sound 3 | Stimulation Signal (3,1) | Stimulation Signal (3,2) | Stimulation Signal (3,3) | ... | Stimulation Signal (3,m) |
| ⋮ | ⋮ | ⋮ | ⋮ | ⋱ | ⋮ |
| Sound n | Stimulation Signal (n,1) | Stimulation Signal (n,2) | Stimulation Signal (n,3) | ... | Stimulation Signal (n,m) |

FIG. 18

|  | Programmer | Charger | Smartphone/Tablet | Smartwatch/Wearable | Fob |
|---|---|---|---|---|---|
| On/Off | X | X | X | X | X |
| Switch Profile/Transfer Function | X | X | X | X | X |
| Adjust Volume | X | X | X | X | X |
| Adjust Mix | X | X | X | X | |
| Receive Audio Stream | X | | X | X | |
| Broadcast Audio Stream | X | | X | X | |
| Emergency Shut-off | X | X | X | X | X |
| Initial Wireless Pairing | | X | | | |

FIG. 23

IMPLANTABLE COCHLEAR SYSTEM WITH INTEGRATED COMPONENTS AND LEAD CHARACTERIZATION

RELATED APPLICATIONS

This application is a divisional of U.S. patent application Ser. No. 16/797,392, filed Feb. 21, 2020, which claims the benefit of U.S. Provisional Patent Application No. 62/808,634, filed Feb. 21, 2019. The contents of each of these applications is incorporated herein by reference.

BACKGROUND

A cochlear implant is an electronic device that may be at least partially implanted surgically into the cochlea, the hearing organ of the inner ear, to provide improved hearing to a patient. Cochlear implants may include components that are worn externally by the patient and components that are implanted internally in the patient.

External components may include a microphone, a processor, and a transmitter. Cochlear implants may detect sounds via an ear level microphone that conveys these sounds to a wearable processor. Some processors may be worn behind the patient's ear. An electronic signal from the processor may be sent to a transmission coil worn externally behind the ear over the implant. The transmission coil may send a signal to the implant receiver, located under the patient's scalp.

Internal components may include a receiver and one or more electrodes. Some cochlear implants may include additional processing circuitry among the internal components. The receiver may direct signals to one or more electrodes that have been implanted within the cochlea. The responses to these signals may then be conveyed along the auditory nerve to the cortex of the brain where they are interpreted as sound.

Some cochlear implants may be fully implanted and include a mechanism for measuring sound similar to a microphone, signal processing electronics, and means for directing signals to one or more electrodes implanted within the cochlea. Fully implanted cochlear implants typically do not include a transmission coil or a receiver coil.

Internal components of such cochlear implant systems typically require electrical power to operate. Thus, a power supply is typically included along with the other internal components. However, performance of such power supplies often degrades over time, and the power supply may require replacement. Additionally, processing circuitry technology continues to advance quickly. Improvements to processing technology over time may render the processing technology in the implanted processing circuitry outdated. Thus, there may be times when it is advantageous to replace/upgrade the processing circuitry.

However, such replacement procedures can be difficult. The location of the implanted internal components is not the most amenable to surgical procedures and tends not to fully heal after many incisions. Additionally, replacement of some components, such as a signal processor, can require removing and reintroducing components such as electrical leads into the patient's cochlear tissue, which can be damaging to the tissue and negatively impact the efficacy of cochlear stimulation.

Additionally, different challenges exist for communicating electrical signals through a patient's body. For example, safety standards can limit the amount of current that can safely flow through a patient's body (particularly DC current). Additionally, the patient's body can act as an undesired signal path between different components within the body (e.g., via contact with the housing or "can" of each component). This can lead to reduced signal strength and/or undesired communication or interference between components. In some cases, electrical signals may even stimulate undesired regions of the patient's cochlear tissue, interfering with the efficacy of the cochlear implant.

SUMMARY

Some aspects of the disclosure are generally directed toward cochlear implant systems. Such systems can include a cochlear electrode, a stimulator in electrical communication with the cochlear electrode, an input source, and a signal processor. The signal processor can be configured to receive an input signal from the input source and output a stimulation signal to the stimulator based on the received input signal and a transfer function of the signal processor.

In some examples, the signal processor includes an analog processing stage and a digital processing stage. In some such examples, the signal processor is configured to receive an input signal from an input source and input the received input signal to the analog processing stage to generate an analog processed signal. The signal processor can input the analog processed signal to the digital processing stage to generate a digitally processed signal. In some examples, the signal processor is configured such that the digitally processed signal corresponds to a normalized stimulus signal having reduced gain variability across a range of frequencies and compensating for variability in the frequency response of the middle ear sensor.

In some embodiments, the analog processing stage and/or the digital processing stage are adjustable to normalize the frequency response of the combined analog processing stage and digital processing stage. In some examples, normalizing the frequency response makes a ratio of a digital processed signal to a received corresponding stimulus signal approximately consistent across a plurality of frequencies or frequency ranges.

Some aspects of the disclosure relate to a method for compensating for variability in a middle ear sensor. In some examples, methods include receiving a stimulus signal via a middle ear sensor and generating, via the middle ear sensor, an input signal based on the stimulus signal. Methods can include applying an analog filter to the generated input signal to generate an analog filtered signal and applying a digital filter to the generated analog filtered signal to generate a digitally filtered signal.

In some examples, methods include measuring a frequency response of the digitally filtered signal and/or the analog filtered signal with respect to the input signal and adjusting the digital filter to normalize the frequency response of the digitally filtered signal with respect to the stimulus signal. In some examples, such methods further include applying a plurality of stimulus signals to the middle ear sensor having known frequency content. In some such examples, measuring the frequency response of the digitally filtered signal with respect to the stimulus signal is performed for each of the plurality of stimulus signals.

BRIEF DESCRIPTION OF THE DRAWINGS

FIG. 14A is a schematic diagram showing an exemplary signal processing configuration for adapting to variability in a sensor frequency response.

FIG. 14B shows an exemplary gain vs. frequency response curve for signals at various stages in the processing configuration.

FIG. 18 is a schematic representation of an exemplary database of pre-processed sound signals.

FIG. 23 is a chart showing the various parameters that are adjustable by each of a variety of external devices.

DETAILED DESCRIPTION

Figure 1:
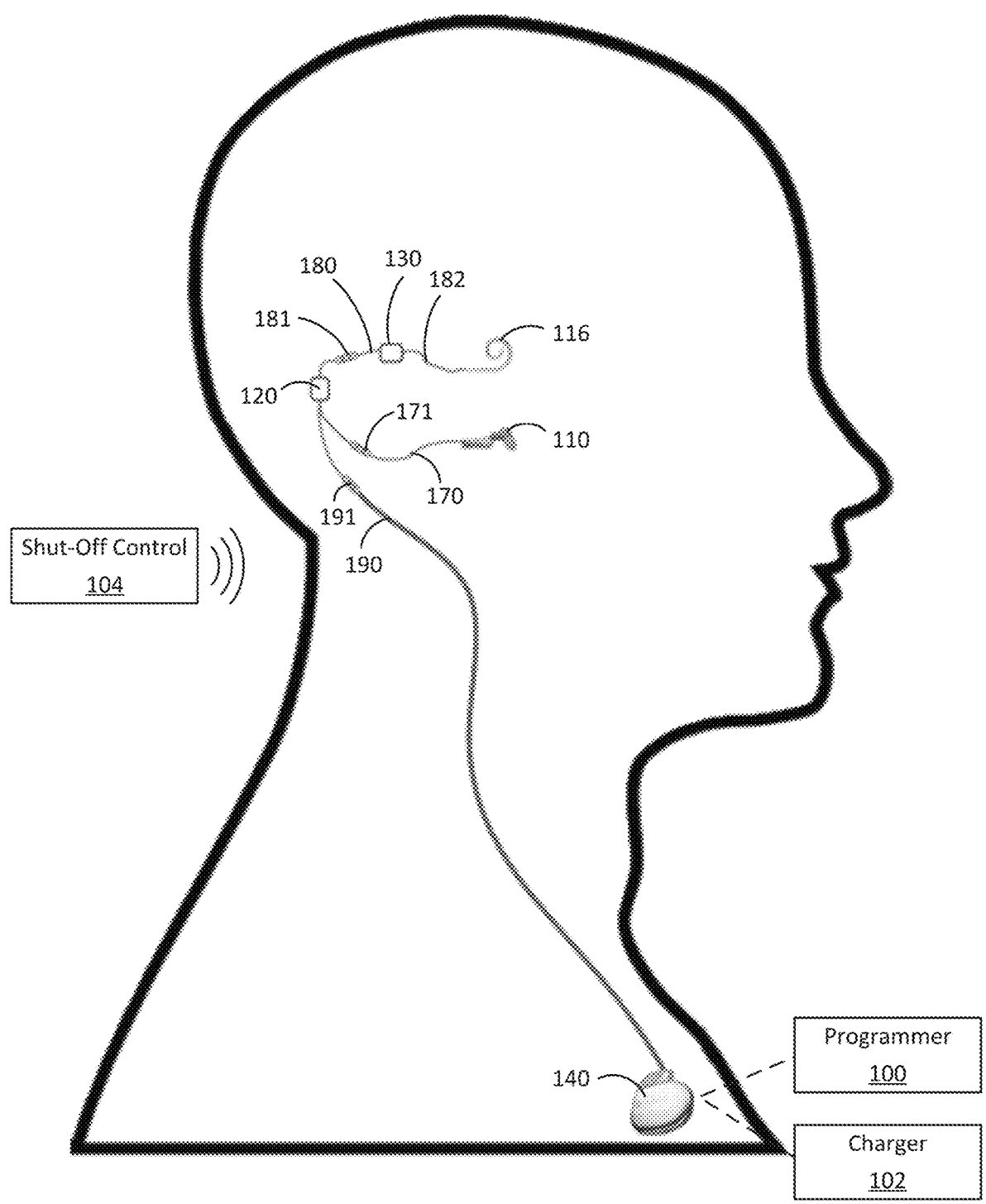
FIG. 1 shows a schematic illustration of a fully implantable cochlear implant system.

FIG. 1 shows a schematic illustration of a fully implantable cochlear implant system. The system of FIG. 1 includes a middle ear sensor 110 in communication with a signal processor 120. The middle ear sensor 110 can be configured to detect incoming sound waves, for example, using the ear structure of a patient. The signal processor 120 can be configured to receive a signal from the middle ear sensor 110 and produce an output signal based thereon. For example, the signal processor 120 can be programmed with instructions to output a certain signal based on a received signal. In some embodiments, the output of the signal processor 120 can be calculated using an equation based on received input signals. Alternatively, in some embodiments, the output of the signal processor 120 can be based on a lookup table or other programmed (e.g., in memory) correspondence between the input signal from the middle ear sensor 110 and the output signal. While not necessarily based explicitly on a function, the relationship between the input to the signal processor 120 (e.g., from the middle ear sensor 110) and the output of the signal processor 120 is referred to as the transfer function of the signal processor 120.

The system of FIG. 1 further includes a cochlear electrode 116 implanted into the cochlear tissues of a patient. The cochlear electrode 116 is in electrical communication with an electrical stimulator 130, which can be configured to provide electrical signals to the cochlear electrode 116 in response to input signals received by the electrical stimulator 130. In some examples, the cochlear electrode 116 is fixedly attached to the electrical stimulator 130. In other examples, the cochlear electrode 116 is removably attached to the electrical stimulator 130. As shown, the electrical stimulator 130 is in communication with the signal processor 120. In some embodiments, the electrical stimulator 130 provides electrical signals to the cochlear electrode 116 based on output signals from the signal processor 120.

In various embodiments, the cochlear electrode 116 can include any number of contact electrodes in electrical contact with different parts of the cochlear tissue. In such embodiments, the electrical stimulator 130 can be configured to provide electrical signals to any number of such contact electrodes to stimulate the cochlear tissue. For example, in some embodiments, the electrical stimulator 130 is configured to activate different contact electrodes or combinations of contact electrodes of the cochlear electrode 116 in response to different input signals received from the signal processor 120. This can help the patient differentiate between different input signals.

During exemplary operation, the middle ear sensor 110 detects audio signals, for example, using features of the patient's ear anatomy as described elsewhere herein and in U.S. Patent Publication No. 2013/0018216, which is hereby incorporated by reference in its entirety. The signal processor 120 can receive such signals from the middle ear sensor 110 and produce an output to the electrical stimulator 130 based on the transfer function of the signal processor 120. The electrical stimulator 130 can then stimulate one or more contact electrodes of the cochlear electrode 116 based on the received signals from the signal processor 120.

Figure 2:
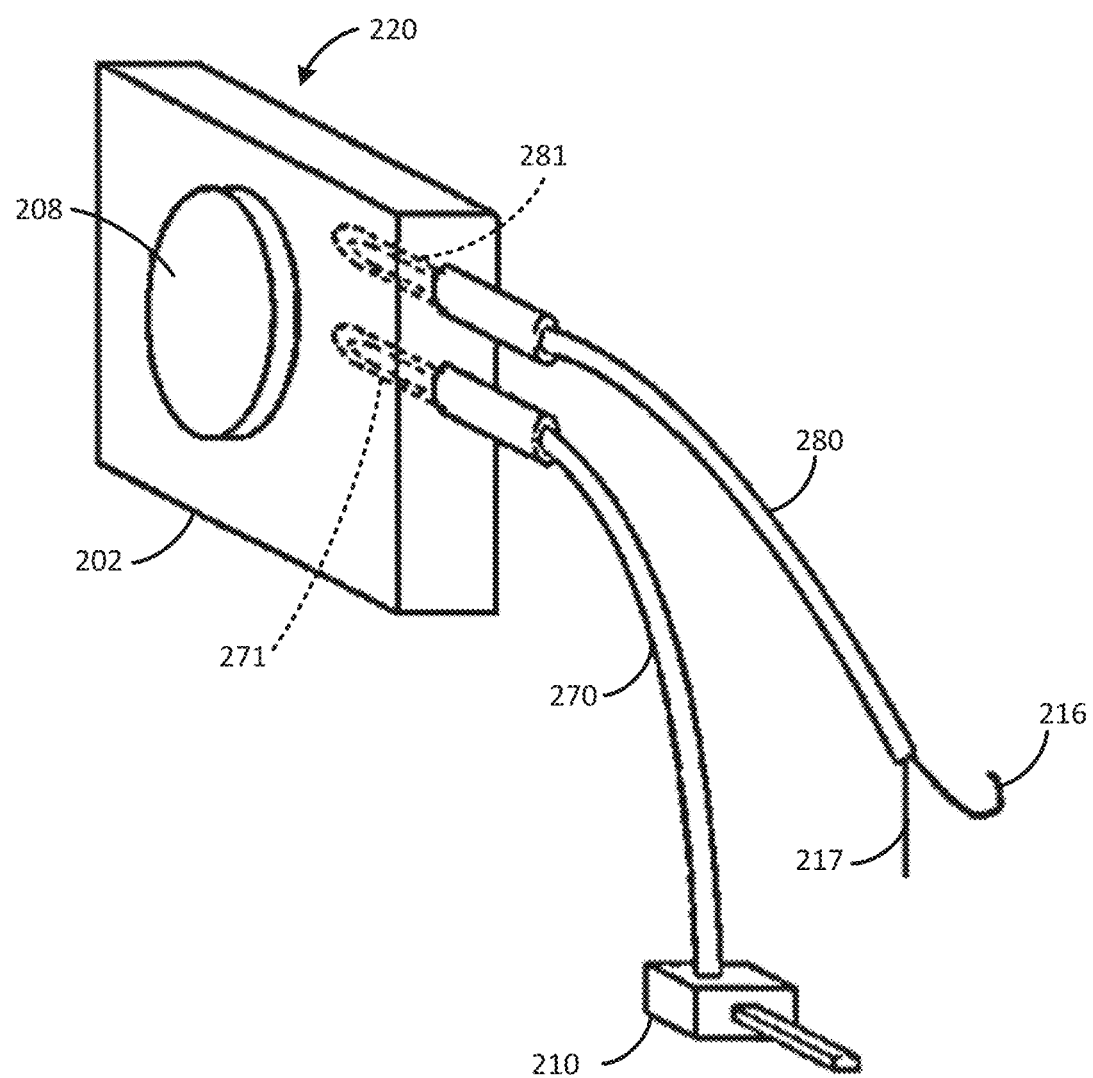
FIG. 2 shows an embodiment of a fully-implantable cochlear implant.

Referring to FIG. 2, an embodiment of a fully-implantable cochlear implant is shown. The device in this embodiment includes a processor 220 (e.g., signal processor), a sensor 210, a first lead 270 connecting the sensor 210 to the processor 220, and a combination lead 280 attached to the processor 220, wherein combination lead 280 contains both a ground electrode 217 and a cochlear electrode 216. The illustrated processor 220 includes a housing 202, a coil 208, first female receptacle 271 and second female receptacle 281 for insertion of the leads 270 and 280, respectively.

In some embodiments, coil 208 can receive power and/or data from an external device, for instance, including a transmission coil (not shown). Some such examples are described in U.S. Patent Publication No. 2013/0018216, which is incorporated by reference. In other examples, processor 220 is configured to receive power and/or data from other sources, such as an implantable battery and/or communication module as shown in FIG. 1. Such battery and/or communication module can be implanted, for example, into the pectoral region of the patient in order to provide adequate room for larger equipment (e.g., a relatively large battery) for prolonged operation (e.g., longer battery life). Additionally, in the event a battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

Figure 3A:
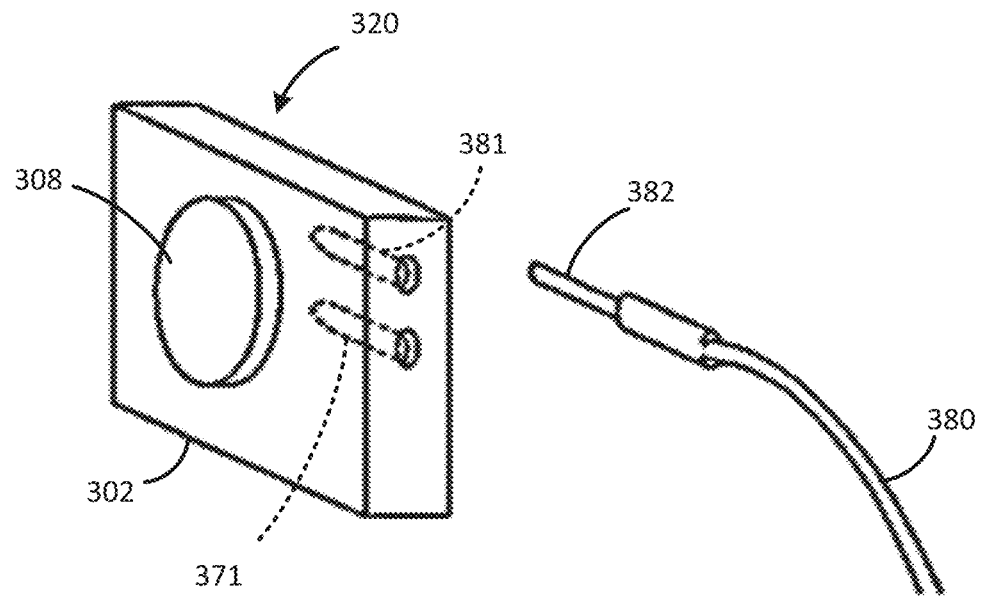
FIGS. 3A and 3B are exemplary illustrations showing communication with the signal processor.
Figure 3B:
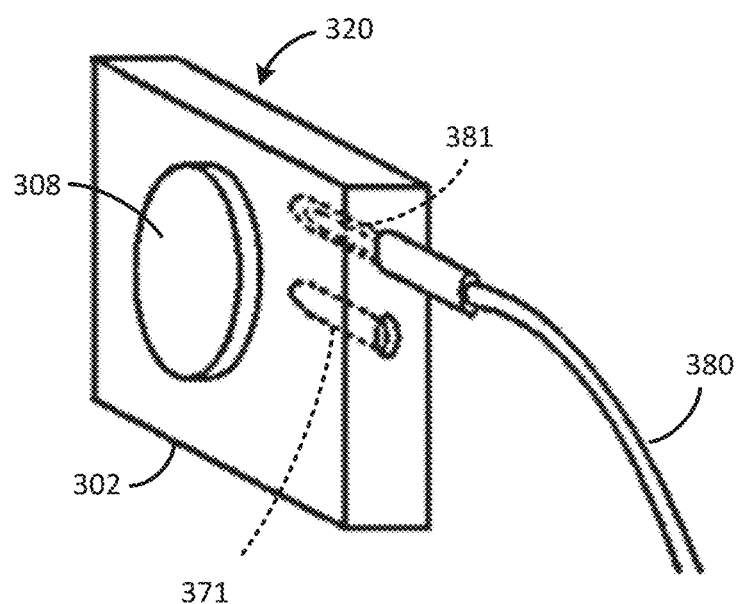

FIGS. 3A and 3B are exemplary illustrations showing communication with a signal processor. For example, referring to FIGS. 3A and 3B, the processor 320, includes a housing 302, a coil 308, and a generic lead 380 are shown. The lead 380 is removable and can be attached to the processor 320 by insertion of a male connector 382 of the generic lead 380 into any available female receptacle, shown here as 371 or 381. FIG. 3A shows the processor 320 with the generic lead 380 removed. FIG. 3B shows the processor 320 with the generic lead 380 attached. The male connector 382 is exchangeable, and acts as a seal to prevent or minimize fluid transfer into the processor 320.

Figure 4:
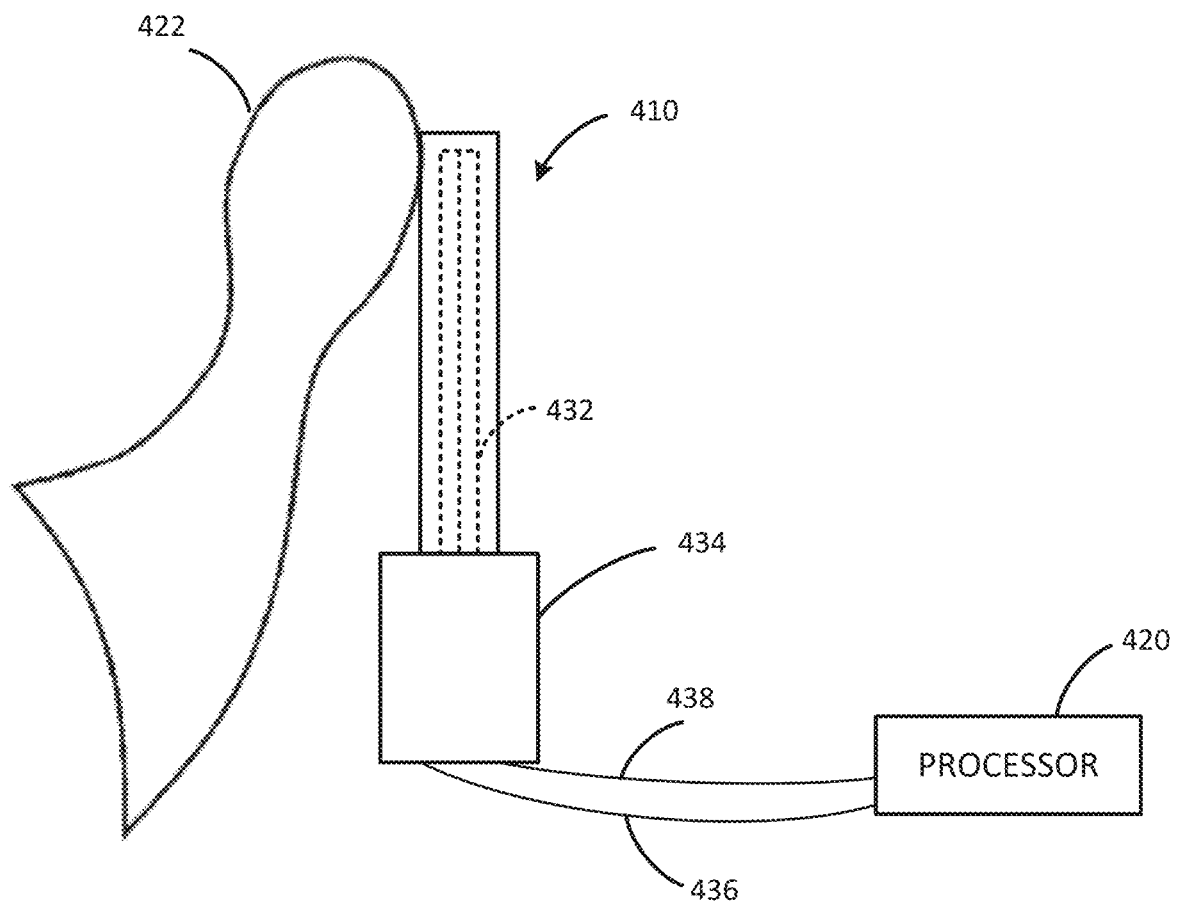
FIGS. 4 and 5 illustrate embodiments of an exemplary middle ear sensor for use in conjunction with anatomical features of a patient.
Figure 5:
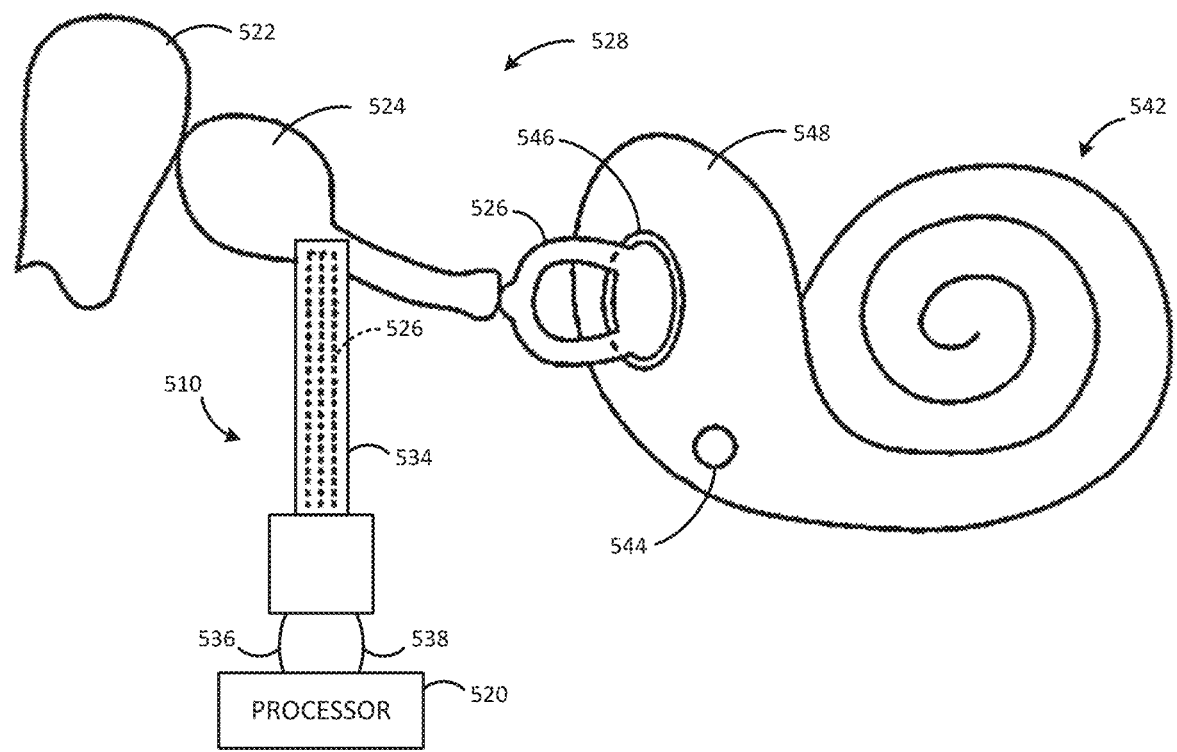

FIGS. 4 and 5 illustrate embodiments of an exemplary middle ear sensor for use in conjunction with anatomical features of a patient. Referring to FIG. 4, an embodiment of the sensor 410 of a fully-implantable cochlear implant is shown. Here, the sensor 410 is touching the malleus 422. The sensor may include a cantilever 432 within a sensor housing 434. The sensor 410 may be in communication with the processor 420 by at least two wires 436 and 438, which may form a first lead (e.g., 270). Both wires can be made of biocompatible materials but need not necessarily be the same biocompatible material. Examples of such biocompatible materials can include tungsten, platinum, palladium, and the like. In various embodiments, one, both, or neither of wires 436 and 438 are coated with a coating and/or disposed inside a casing, such as described in U.S. Patent Publication No. 2013/0018216, which is incorporated by reference.

The illustrated cantilever 432 includes at least two ends, where at least one end is in operative contact with the tympanic membrane or one or more bones of the ossicular chain. The cantilever 432 may be a laminate of at least two layers of material. The material used may be piezoelectric. One example of such a cantilever 432 is a piezoelectric bimorph, which is well-known in the art (see for example, U.S. Pat. No. 5,762,583). In one embodiment, the cantilever is made of two layers of piezoelectric material. In another embodiment, the cantilever is made of more than two layers of piezoelectric material. In yet another embodiment, the cantilever is made of more than two layers of piezoelectric material and non-piezoelectric material.

The sensor housing 434 of the sensor 410 may be made of a biocompatible material. In one embodiment, the biocompatible material may be titanium or gold. In another embodiment, the sensor 410 may be similar to the sensor described in U.S. Pat. No. 7,524,278 to Madsen et al., or available sensors, such as that used in the ESTEEM™ implant (Envoy Medical, Corp., St. Paul, Minn.), for example. In alternative embodiments, the sensor 410 may be an electromagnetic sensor, an optical sensor, or an accelerometer. Accelerometers are known in the art, for example, as described in U.S. Pat. No. 5,540,095.

Referring to FIG. 5, an embodiment of the sensor 510 of a fully-implantable cochlear implant is shown. Also shown are portions of the subject's anatomy, which includes, if the subject is anatomically normal, at least the malleus 522, incus 524, and stapes 526 of the middle ear 528, and the cochlea 548, oval window 546, and round window 544 of the inner ear 542. Here, the sensor 510 is touching the incus 524. The sensor 510 in this embodiment can be as described for the embodiment of sensor 410 shown in FIG. 4. Further, although not shown in a drawing, the sensor 510 may be in operative contact with the tympanic membrane or the stapes, or any combination of the tympanic membrane, malleus 522, incus 524, or stapes 526.

FIGS. 4 and 5 illustrate an exemplary middle ear sensor for use with systems described herein. However, other middle ear sensors can be used, such as sensors using microphones or other sensors capable of receiving an input corresponding to detected sound and outputting a corresponding signal to the signal processor. Additionally or alternatively, systems can include other sensors configured to output a signal representative of sound received at or near a user's ear, such as a microphone or other acoustic pickup located in the user's outer ear or implanted under the user's skin. Such devices may function as an input source, for example, to the signal processor such that the signal processor receives an input signal from the input source and generates and output one or more stimulation signals according to the received input signal and the signal processor transfer function.

Referring back to FIG. 1, the signal processor 120 is shown as being in communication with the middle ear sensor 110, the electrical stimulator 130, and the implantable battery and/or communication module 140. As described elsewhere herein, the signal processor 120 can receive input signals from the middle ear sensor 110 and/or other input source(s) and output signals to the electrical stimulator 130 for stimulating the cochlear electrode 116. The signal processor 120 can receive data (e.g., processing data establishing or updating the transfer function of the signal processor 120) and/or power from the implantable battery and/or communication module 140. In some embodiments, the signal processor 120 can communicate with such components via inputs such as those shown in FIG. 3.

In some embodiments, the implantable battery and/or communication module 140 can communicate with external components, such as a programmer 100 and/or a battery charger 102. The battery charger 102 can wirelessly charge the battery in the implantable battery and/or communication module 140 when brought into proximity with the implantable battery and/or communication module 140 in the pectoral region of the patient. Such charging can be accomplished, for example, using inductive charging. The programmer 100 can be configured to wirelessly communicate with the implantable battery and/or communication module 140 via any appropriate wireless communication technology, such as Bluetooth, Wi-Fi, and the like. In some examples, the programmer 100 can be used to update the system firmware and/or software. In an exemplary operation, the programmer 100 can be used to communicate an updated signal processor 120 transfer function to the implantable battery and/or communication module 140. In various embodiments, the programmer 100 and charger 102 can be separate devices or can be integrated into a single device.

In the illustrated example of FIG. 1, the signal processor 120 is connected to the middle ear sensor 110 via lead 170. In some embodiments, lead 170 can provide communication between the signal processor 120 and the middle ear sensor 110. In some embodiments, lead 170 can include a plurality of isolated conductors providing a plurality of communication channels between the middle ear sensor 110 and the signal processor 120. The lead 170 can include a coating such as an electrically insulating sheath to minimize any conduction of electrical signals to the body of the patient.

Figure 6:
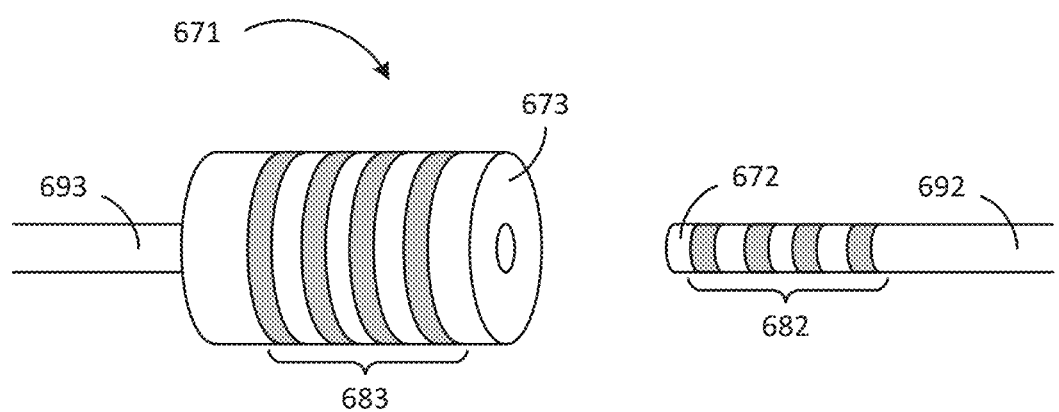
FIG. 6 shows an illustration of an exemplary detachable connector.

In various embodiments, one or more communication leads can be detachable such that communication between two components can be disconnected in order to electrically and/or mechanically separate such components. For instance, in some embodiments, lead 170 includes a detachable connector 171. Detachable connector 171 can facilitate decoupling of the signal processor 120 and middle ear sensor 110. FIG. 6 shows an illustration of an exemplary detachable connector. In the illustrated example, the detachable connector 671 includes a male connector 672 and a female connector 673. In the illustrated example, the male connector 672 includes a plurality of isolated electrical contacts 682 and female connector 673 includes a corresponding plurality of electrical contacts 683. When the male connector 672 is inserted into the female connector 673, contacts 682 make electrical contact with contacts 683. Each corresponding pair of contacts 682, 683 can provide a separate channel of communication between components connected via the detachable connector 671. In the illustrated example, four channels of communication are possible, but it will be appreciated that any number of communication channels are possible. Additionally, while shown as individual circumferentially extending contacts 683, other configurations are possible.

In some embodiments, male 672 and female 673 connectors are attached at the end of leads 692, 693, respectively. Such leads can extend from components of the implantable cochlear system. For example, with reference to FIG. 1, in some embodiments, lead 170 can include a first lead extending from the middle ear sensor 110 having one of a male (e.g., 672) or a female (e.g., 673) connector and a second lead extending from the signal processor 120 having the other of the male or female connector. The first and second leads can be connected at detachable connector 171 in order to facilitate communication between the middle ear sensor 110 and the signal processor 120.

In other examples, a part of the detachable connector 171 can be integrated into one of the middle ear sensor 110 and the signal processor 120 (e.g., as shown in FIG. 3). For example, in an exemplary embodiment, the signal processor 120 can include a female connector (e.g., 673) integrated into a housing of the signal processor 120. Lead 170 can extend fully from the middle ear sensor 110 and terminate at a corresponding male connector (e.g., 672) for inserting into the female connector of the signal processor 120. In still further embodiments, a lead (e.g., 170) can include connectors on each end configured to detachably connect with connectors integrated into each of the components in communication. For example, lead 170 can include two male connectors, two female connectors, or one male and one female connector for detachably connecting with corresponding connectors integral to the middle ear sensor 110 and the signal processor 120. Thus, lead 170 may include two or more detachable connectors.

Similar communication configurations can be established for detachable connector 181 of lead 180 facilitating communication between the signal processor 120 and the stimulator 130 and for detachable connector 191 of lead 190 facilitating communication between the signal processor 120 and the implantable battery and/or communication module 140. Leads (170, 180, 190) can include pairs of leads having corresponding connectors extending from each piece of communicating equipment, or connectors can be built in to any one or more communicating components.

In such configurations, each of the electrical stimulator 130, signal processor 120, middle ear sensor 110, and battery and/or communication module can each be enclosed in a housing, such as a hermetically sealed housing comprising biocompatible materials. Such components can include feedthroughs providing communication to internal components enclosed in the housing. Feedthroughs can provide electrical communication to the component via leads extending from the housing and/or connectors integrated into the components.

In a module configuration such as that shown in FIG. 1, various components can be accessed (e.g., for upgrades, repair, replacement, etc.) individually from other components. For example, as signal processor 120 technology improves (e.g., improvements in size, processing speed, power consumption, etc.), the signal processor 120 implanted as part of the system can be removed and replaced independently of other components. In an exemplary procedure, an implanted signal processor 120 can be disconnected from the electrical stimulator 130 by disconnecting detachable connector 181, from the middle ear sensor 110 by disconnecting detachable connector 171, and from the implantable battery and/or communication module 140 by disconnecting detachable connector 191. Thus, the signal processor 120 can be removed from the patient while other components such as the electrical stimulator 130, cochlear electrode 116, middle ear sensor 110, and battery and/or communication module can remain in place in the patient.

After the old signal processor is removed, a new signal processor can be connected to the electrical stimulator 130, middle ear sensor 110, and implantable battery and/or communication module 140 via detachable connectors 181, 171, and 191, respectively. Thus, the signal processor (e.g., 120) can be replaced, repaired, upgraded, or any combination thereof, without affecting the other system components. This can reduce, among other things, the risk, complexity, duration, and recovery time of such a procedure. In particular, the cochlear electrode 116 can be left in place in the patient's cochlea while other system components can be adjusted, reducing trauma to the patient's cochlear tissue.

Such modularity of system components can be particularly advantageous when replacing a signal processor 120, such as described above. Processor technology continues to improve and will likely continue to markedly improve in the future, making the signal processor 120 a likely candidate for significant upgrades and/or replacement during the patient's lifetime. Additionally, in embodiments such as the embodiment shown in FIG. 1, the signal processor 120 communicates with many system components. For example, as shown, the signal processor 120 is in communication with each of the electrical stimulator 130, the middle ear sensor 110, and the implantable battery and/or communication module 140. Detachably connecting such components with the signal processor 120 (e.g., via detachable connectors 181, 171, and 191) enables replacement of the signal processor 120 without disturbing any other components. Thus, in the event of an available signal processor 120 upgrade and/or a failure of the signal processor 120, the signal processor 120 can be disconnected from other system components and removed.

While many advantages exist for a replaceable signal processor 120, the modularity of other system components can be similarly advantageous, for example, for upgrading any system component. Similarly, if a system component (e.g., the middle ear sensor 110) should fail, the component can be disconnected from the rest of the system (e.g., via detachable connector 171) and replaced without disturbing the remaining system components. In another example, even a rechargeable battery included in the implantable battery and/or communication module 140 may eventually wear out and need replacement. The implantable battery and/or communication module 140 can be replaced or accessed (e.g., for replacing the battery) without disturbing other system components. Further, as discussed elsewhere herein, when the implantable battery and/or communication module 140 is implanted in the pectoral region of the patient, such as in the illustrated example, such a procedure can leave the patient's head untouched, eliminating unnecessarily frequent access beneath the skin.

While various components are described herein as being detachable, in various embodiments, one or more components configured to communicate with one another can be integrated into a single housing. For example, in some embodiments, signal processor 120 can be integrally formed with the stimulator 130 and cochlear electrode 116. For example, in an exemplary embodiment, processing and stimulation circuitry of a signal processor 120 and stimulator 130 can be integrally formed as a single unit in a housing coupled to a cochlear electrode. Cochlear electrode and the signal processor/stimulator can be implanted during an initial procedure and operate as a single unit.

In some embodiments, while the integral signal processor/stimulator/cochlear electrode component does not get removed from a patient due to potential damage to the cochlear tissue into which the cochlear electrode is implanted, system upgrades are still possible. For example, in some embodiments, a module signal processor may be implanted alongside the integral signal processor/stimulator component and communicate therewith. In some such examples, the integral signal processor may include a built-in bypass to allow a later-implanted signal processor to interface directly with the stimulator. Additionally or alternatively, the modular signal processor can communicate with the integral signal processor, which may be programmed with a unity transfer function. Thus, in some such embodiments, signals from the modular signal processor may be essentially passed through the integral signal processor unchanged so that the modular signal processor effectively controls action of the integral stimulator. Thus, in various embodiments, hardware and/or software solutions exist for upgrading an integrally attached signal processor that may be difficult or dangerous to remove.

Figure 7:
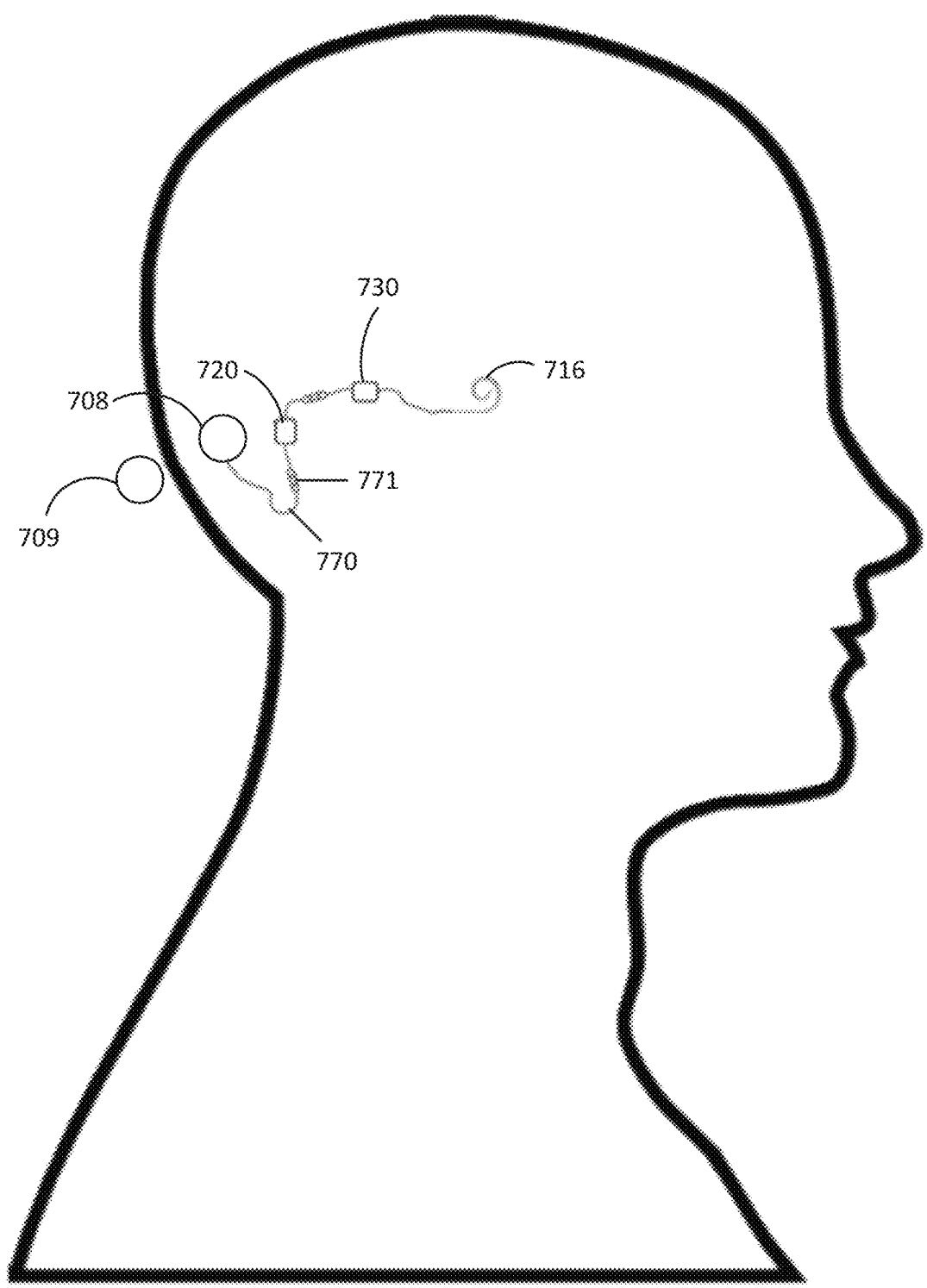
FIG. 7 shows an exemplary cochlear implant system in a patient that is not fully physically developed, such as a child.

Another advantage to a modular cochlear implant system such as shown in FIG. 1 is the ability to implant different system components into a patient at different times. For example, infants and children are typically not suited for a fully implantable system such as shown in FIG. 1. Instead, such patients typically are candidates to wear a traditional cochlear implant system. For example, FIG. 7 shows an exemplary cochlear implant system in a patient that is not fully physically developed, such as a child. The system includes a cochlear electrode 716 implanted into the cochlear tissue of the patient. The cochlear electrode 716 of FIG. 7 can include many of the properties of the cochlear electrodes described herein. The cochlear electrode 716 can be in electrical communication with an electrical stimulator 730, which can be configured to stimulate portions of the cochlear electrode 716 in response to an input signal, such as described elsewhere herein. The electrical stimulator 730 can receive input signals from a signal processor 720.

In some cases, components such as a middle ear sensor are incompatible with a patient who is not fully physically developed. For example, various dimensions within a growing patient's anatomy, such as spacing between anatomical structures or between locations on anatomical structures (e.g., equipment attachment points) may change as the patient grows, thereby potentially rendering a middle ear sensor that is extremely sensitive to motion ineffective. Similarly, the undeveloped patient may not be able to support the implantable battery and/or communication module. Thus, the signal processor 720 can be in communication with a communication device for communicating with components external to the patient. Such communication components can include, for example, a coil 708, shown as being connected to the signal processor 720 via lead 770. The coil 708 can be used to receive data and/or power from devices external to the user. For example, microphone or other audio sensing device (not shown) can be in communication with an external coil 709 configured to transmit data to the coil 708 implanted in the patient. Similarly, a power source (e.g., a battery) can be coupled to an external coil 709 and configured to provide power to the implanted components via the implanted coil 708. Additionally, processing data (e.g., updates to the signal processor 720 transfer function)

can also be communicated to the implanted coil 708 from an external coil 709. While generally discussed using coil 708, it will be appreciated that communication between external and implanted components (e.g., the signal processor 720) can be performed using other communication technology, such as various forms of wireless communication. As shown, in the embodiment of FIG. 7, the signal processor 720 is coupled to the coil 708 via lead 770 and detachable connector 771. Accordingly, the coil 708 can be detached from the signal processor 720 and removed without disrupting the signal processor 720.

When a patient has become fully developed, for example, to the point that the patient can safely accommodate a middle ear sensor and an implantable battery and/or communication module, the coil 708 can be removed and remaining components of the fully implantable system can be implanted. That is, once a patient is developed, the cochlear implant system (e.g., of FIG. 7) can be updated to a fully implantable cochlear implant system (e.g., of FIG. 1). In some examples, the patient is considered sufficiently developed once the patient reaches age 18 or another predetermined age. Additional or alternative criteria may be used, such as when various anatomical sizes or determined developmental states are achieved.

Figure 8:
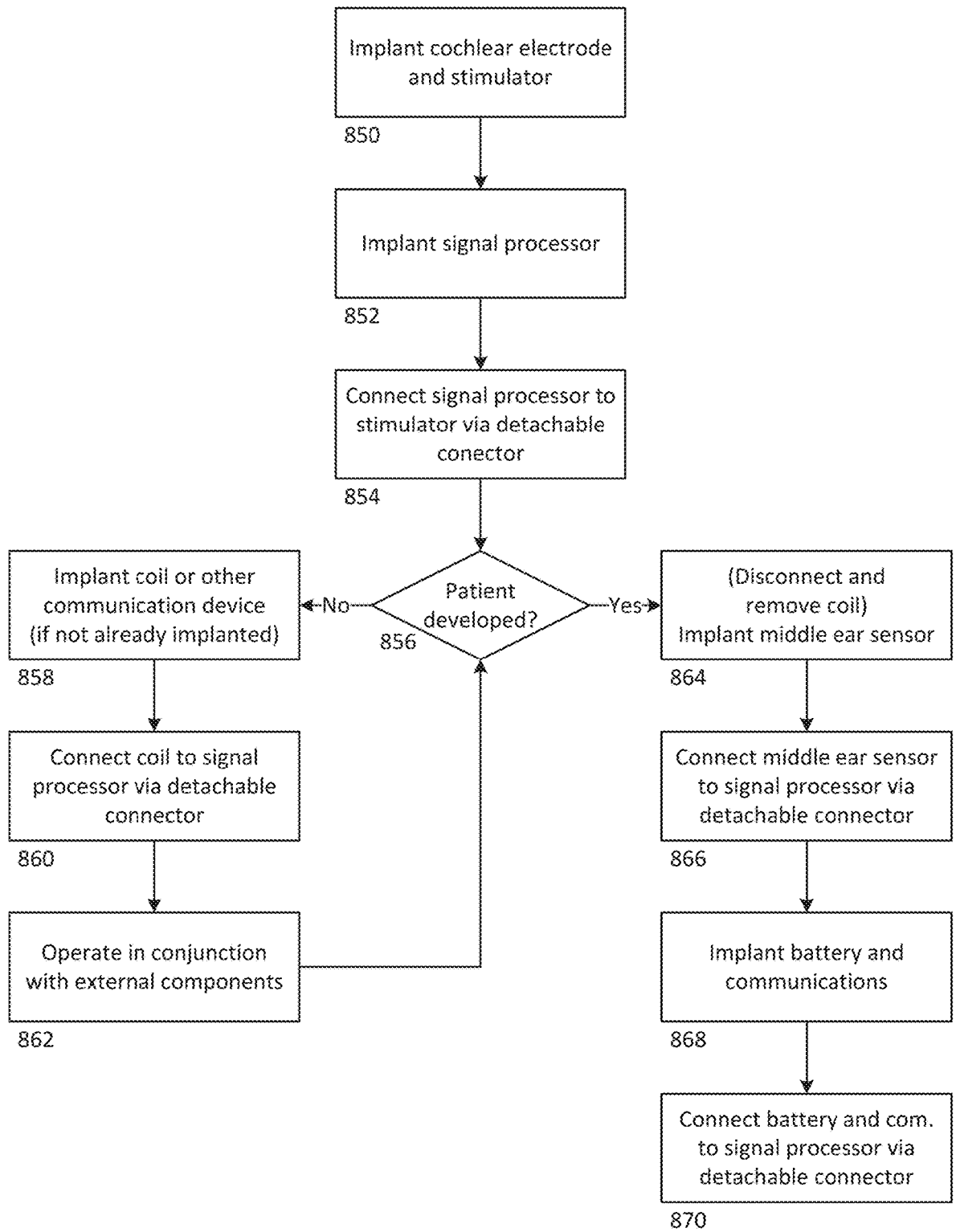
FIG. 8 is a process-flow diagram illustrating an exemplary process for installing and/or updating an implantable cochlear implant system into a patient.

FIG. 8 is a process-flow diagram illustrating an exemplary process for installing and/or updating an implantable cochlear implant system into a patient. A cochlear electrode can be implanted in communication with the patient's cochlear tissue and an electrical stimulator can be implanted in communication with the cochlear electrode (step 850). A signal processor can be implanted into the patient (step 852). As described elsewhere herein, the signal processor can be connected to the electrical stimulator via a detachable connector (step 854). In examples in which the signal processor is integrally formed with one or more components, such as the stimulator and cochlear electrode, steps 850, 852, and 854 can be combined into a single step comprising implanting the cochlear electrode, stimulator, and signal processor component.

If, at the time of implementing the process of FIG. 8, it can be determined if the patient is considered sufficiently developed (step 856). If not, a coil (or other communication device) such as described with respect to FIG. 7 can be implanted (step 858). The coil can be connected to the signal processor via the detachable connector (step 860), and the cochlear implant can operate in conjunction with external components (step 862), such as microphones and external power supplies and coils.

However, if a patient is, or has become, sufficiently developed (step 856), additional components can be implanted into the patient. For example, the method can include implanting a middle ear sensor (step 864) and connecting the middle ear sensor to the signal processor via a detachable connector (step 866). Additionally, the method can include implanting a battery and/or communication module (step 868) and connecting the battery and/or communication module to the signal processor via a detachable connector (step 870). If the patient had become sufficiently developed after having worn a partially external device such as that described with respect to FIG. 7 and steps 858-862, the method can include removing various components that had been previously implanted. For example, a coil, such as implanted in step 858, can be disconnected and removed during the procedure of implanting the middle ear sensor (step 864).

The process of FIG. 8 can be embodied in a method of fitting a patient with an implantable hearing system. Such a method can include implanting a first system (e.g., the system of FIG. 7) into a patient at a first age. This can include, for example, performing steps 850-562 in FIG. 8. The method can further include, when the patient reaches a second age, the second age being greater than the first, removing some components of the first system (e.g., a coil) and implanting the not-yet implanted components of second system (e.g., the system of FIG. 1), for example, via steps 864-870 of FIG. 8.

Transitioning from the system of FIG. 7 to the system of FIG. 1, for example, via the process of FIG. 8, can have several advantages. From a patient preference standpoint, some patients may prefer a system that is totally implanted and requires no wearable external components. Additionally, an implanted battery and/or communication module in communication with the signal processor via lead 190 (and detachable connector 191) can much more efficiently relay power and/or data to the signal processor when compared to an external device such as a coil.

Such modular systems provide distinct advantages over previous implantable or partially implantable cochlear implant systems. Generally, previous systems include several components included into a single housing implanted into the patient. For example, functionality of a signal processor, electrical stimulator, and sensor can be enclosed in a single, complex component. If any such aspects of the component fail, which becomes more likely as the complexity increases, the entire module must be replaced. By contrast, in a modular system, such as shown in FIG. 1, individual components can be replaced while leaving others in place. Additionally, such systems including, for example, coil-to-coil power and/or data communication through the patient's skin also generally communicate less efficiently than an internal connection such as via the lead 190. Modular systems such as shown in FIGS. 1 and 7 also allow for a smooth transition from a partially implantable system for a patient who is not yet fully developed and a fully implantable system once the patient has become fully developed.

While often described herein as using an electrical stimulator to stimulate the patient's cochlear tissue via a cochlear electrode, in some examples, the system can additionally or alternatively include an acoustic stimulator. An acoustic stimulator can include, for example, a transducer (e.g., a piezoelectric transducer) configured to provide mechanical stimulation to the patient's ear structure. In an exemplary embodiment, the acoustic stimulator can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Figure 9:
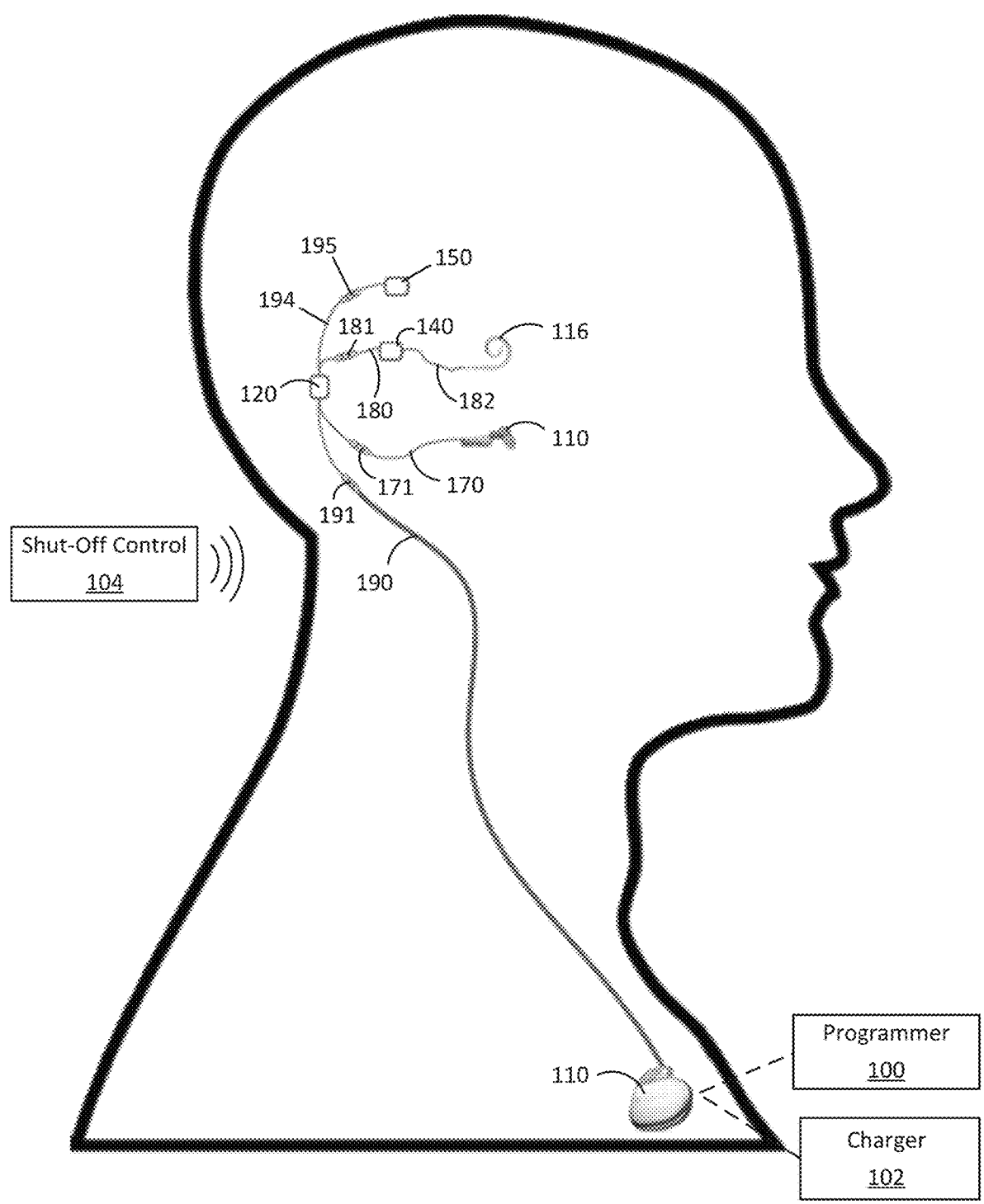
FIG. 9 is a schematic diagram illustrating an exemplary implantable system including an acoustic stimulator.

FIG. 9 is a schematic diagram illustrating an exemplary implantable system including an acoustic stimulator. The acoustic stimulator can be implanted proximate the patient's ossicular chain and can be in communication with a signal processor via lead 194 and detachable connector 195. The signal processor can behave as described elsewhere herein and can be configured to cause acoustic stimulation of the ossicular chain via the acoustic stimulator in in response to input signals from the middle ear sensor according to a transfer function of the signal processor.

The acoustic stimulator of FIG. 9 can be used similarly to the electrical stimulator as described elsewhere herein. For instance, an acoustic stimulator can be mechanically coupled to a patient's ossicular chain upon implanting the system and coupled to the signal processor via lead 194 and detachable connector 195. Similarly to systems described elsewhere herein with respect to the electrical stimulator, if the signal processor requires replacement or repair, the signal processor can be disconnected from the acoustic stimulator (via detachable connector 195) so that the signal processor can be removed without disturbing the acoustic stimulator.

In general, systems incorporating an acoustic sensor such as shown in FIG. 9 can operate in the same way as systems described elsewhere herein employing an electrical stimulator and cochlear electrode only substituting electrical stimulation for acoustic stimulation. The same modularity benefits, including system maintenance and upgrades as well as the ability to convert to a fully implantable system when a patient becomes sufficiently developed, can be similarly realized using acoustic stimulation systems. For example, the process illustrated in FIG. 8 can be performed in an acoustic stimulation system simply by substituting the electrical stimulator and cochlear electrode for an acoustic stimulator.

Some systems can include a hybrid system comprising both an electrical stimulator and an acoustic stimulator in communication with the signal processor. In some such examples, the signal processor can be configured to stimulate electrically and/or acoustically according to the transfer function of the signal processor. In some examples, the type of stimulation used can depend on the input signal received by the signal processor. For instance, in an exemplary embodiment, the frequency content of the input signal to the signal processor can dictate the type of stimulation. In some cases, frequencies below a threshold frequency could be represented using one of electrical and acoustic stimulation while frequencies above the threshold frequency could be represented using the other of electrical and acoustic stimulation. Such a threshold frequency could be adjustable based on the hearing profile of the patient. Using a limited range of frequencies can reduce the number of frequency domains, and thus the number of contact electrodes, on the cochlear electrode. In other examples, rather than a single threshold frequency defining which frequencies are stimulated electrically and acoustically, various frequencies can be stimulated both electrically and acoustically. In some such examples, the relative amount of electrical and acoustic stimulation can be frequency-dependent. As described elsewhere herein, the signal processor transfer function can be updated to meet the needs of the patient, including the electrical and acoustic stimulation profiles.

With further reference to FIGS. 1 and 9, in some examples, a system can include a shut-off controller 104, which can be configured to wirelessly stop an electrical stimulator 130 from stimulating the patient's cochlear tissue and/or an acoustic stimulator 150 from stimulating the patient's ossicular chain. For example, if the system is malfunctioning or an uncomfortably loud input sound causes an undesirable level of stimulation, the user may use the shut-off controller 104 to cease stimulation from the stimulator 130. The shut-off controller 104 can be embodied in a variety of ways. For example, in some embodiments, the shut-off controller 104 can be integrated into other external components, such as the programmer 100. In some such examples, the programmer 100 includes a user interface by which a user can select an emergency shut-off feature to cease stimulation. Additionally or alternatively, the shut-off controller 104 can be embodied as a separate component. This can be useful in situations in which the patient may not have immediate access to the programmer 100. For example, the shut-off controller 104 can be implemented as a wearable component that the patient can wear at all or most times, such as a ring, bracelet, necklace, or the like.

The shut-off controller 104 can communicate with the system in order to stop stimulation in a variety of ways. In some examples, the shut-off controller 104 comprises a magnet that is detectable by a sensor (e.g., a Hall-Effect sensor) implanted in the patient, such as in the processor and/or the implantable battery and/or communication module 140. In some such embodiments, when the magnet is brought sufficiently close to the sensor, the system can stop stimulation of the cochlear tissue or ossicular chain.

After the shut-off controller 104 is used to disable stimulation, stimulation can be re-enabled in one or more of a variety of ways. For example, in some embodiments, stimulation is re-enabled after a predetermined amount of time after it had been disabled. In other examples, the shut-off controller 104 can be used to re-enable stimulation. In some such examples, the patient brings the shut-off controller 104 within a first distance of a sensor (e.g., a magnetic sensor) to disable stimulation, and then removes the shut-off controller 104. Subsequently, once the patient brings the shut-off controller 104 within a second distance of the sensor, stimulation can be re-enabled. In various embodiments, the first distance can be less than the second distance, equal to the second distance, or greater than the second distance. In still further embodiments, another device such as a separate turn-on controller (not shown) or the programmer 100 can be used to re-enable stimulation. Any combination of such re-enabling of stimulation can be used, such as alternatively using either the programmer 100 or the shut-off controller 104 to enable stimulation or combining a minimum "off" time before any other methods can be used to re-enable stimulation.

In some embodiments, rather than entirely disable stimulation, other actions can be taken, such as reducing the magnitude of stimulation. For example, in some embodiments, the shut-off sensor can be used to reduce the signal output by a predetermined amount (e.g., absolute amount, percentage, etc.). In other examples, the shut-off sensor can affect the transfer function of the signal processor to reduce the magnitude of stimulation in a customized way, such as according to frequency or other parameter of an input signal (e.g., from the middle ear sensor).

With reference back to FIG. 1, as described elsewhere herein, the implantable battery and/or communication module can be used to provide power and/or data (e.g., processing instructions) to other system components via lead 190. Different challenges exist for communicating electrical signals through a patient's body. For example, safety standards can limit the amount of current that can safely flow through a patient's body (particularly DC current). Additionally, the patient's body can act as an undesired signal path from component to component (e.g., via contact with the housing or "can" of each component). Various systems and methods can be employed to improve the communication ability between system components.

Figure 10A:
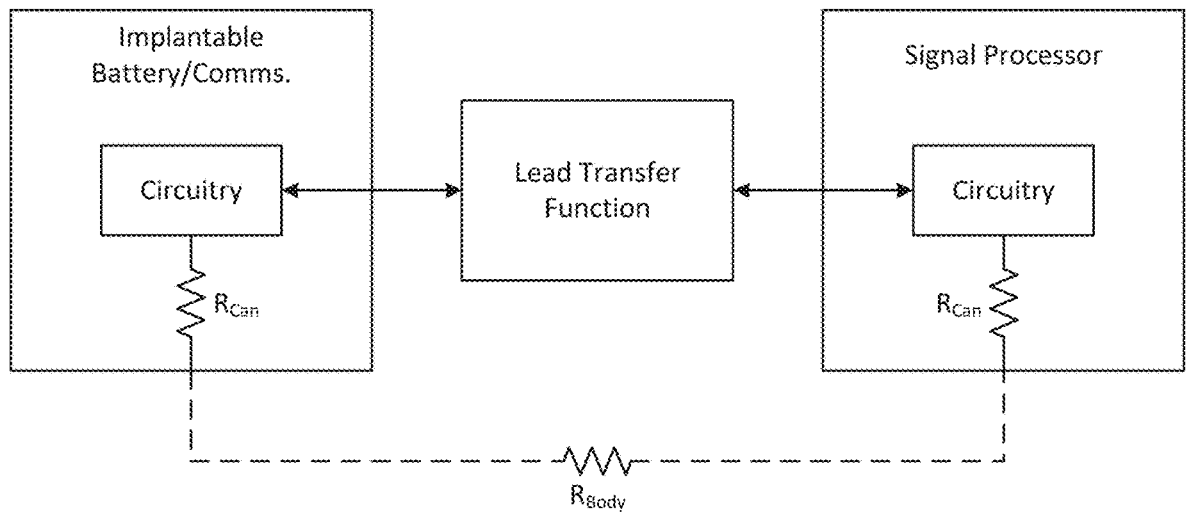
FIG. 10A is a high level electrical schematic showing communication between the implantable battery and/or communication module and the signal processor.

FIG. 10A is a high level electrical schematic showing communication between the implantable battery and/or communication module and the signal processor. In the illustrated embodiment, the implantable battery and/or communication module includes circuitry in communication with circuitry in the signal processor. Communication between the circuitry in the implantable battery and/or communication module and the signal processor can be facilitated by a lead (190), represented by the lead transfer function. The lead transfer function can include, for example, parasitic resistances and capacitances between the leads connecting the implantable battery and/or communication module and the signal processor and the patient's body and/or between two or more conductors that make up the lead (e.g., 191). Signals communicated from the circuitry of the implantable battery and/or communication module to the circuitry in the signal processor can include electrical power provided to operate and/or stimulate system components (e.g., the middle ear sensor, signal processor, electrical and/or acoustic stimulator, and/or cochlear electrode) and/or data (e.g., processing data regarding the transfer function of the signal processor).

As discussed elsewhere herein, the body of the patient provides an electrical path between system components, such as the "can" of the implantable battery and/or communication module and the "can" of the signal processor. This path is represented in FIG. 10A by the flow path through $R_{Body}$. Thus, the patient's body can provide undesirable signal paths which can negatively impact communication between components. To address this, in some embodiments, operating circuitry in each component can be substantially isolated from the component "can" and thus the patient's body. For example, as shown, resistance $R_{Can}$ is positioned between the circuitry and the "can" of both the implantable battery and/or communication module and the signal processor.

While being shown as $R_{Can}$ in each of the implantable battery and/or communication module and the signal processor, it will be appreciated that the actual value of the resistance between the circuitry and respective "can" of different elements is not necessarily equal. Additionally, $R_{Can}$ need not include purely a resistance, but can include other components, such as one or more capacitors, inductors, and the like. That is, $R_{Can}$ can represent an insulating circuit including any variety of components that act to increase the impedance between circuitry within a component and the "can" of the component. Thus, $R_{Can}$ can represent an impedance between the operating circuitry of a component and the respective "can" and the patient's tissue. Isolating the circuitry from the "can" and the patient's body acts to similarly isolate the circuitry from the "can" of other components, allowing each component to operate with reference to a substantially isolated component ground. This can eliminate undesired communication and interference between system components and/or between system components and the patient's body.

Figure 10B:
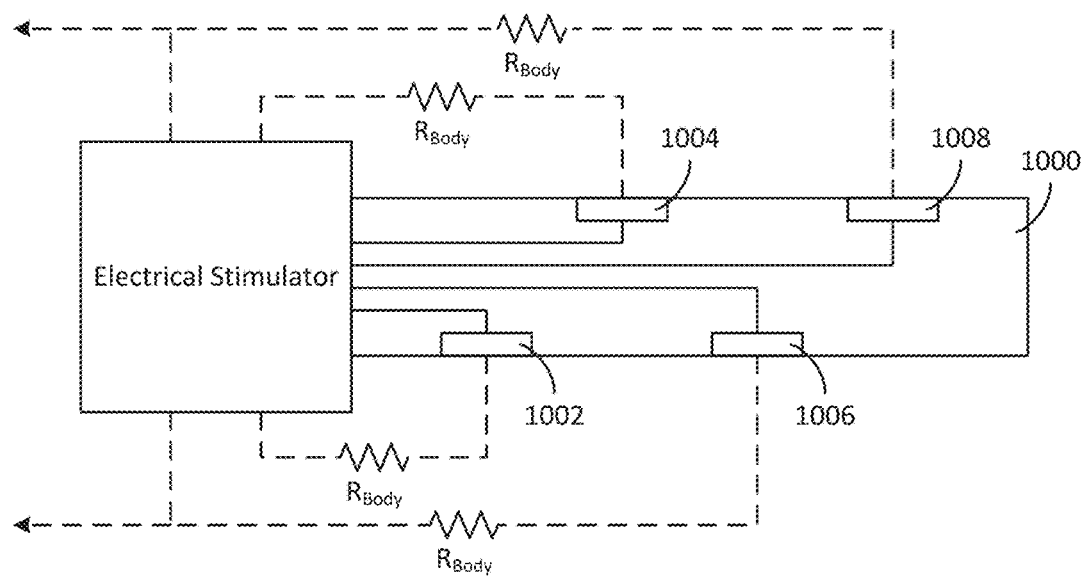
FIG. 10B illustrates an exemplary schematic diagram illustrating a cochlear electrode having a plurality of contact electrodes and fixedly or detachably connected to an electrical stimulator.

For example, as described elsewhere herein, in some examples, an electrical stimulator can provide an electrical stimulus to one or more contact electrodes on a cochlear electrode implanted in a patient's cochlear tissue. FIG. 10B illustrates an exemplary schematic diagram illustrating a cochlear electrode having a plurality of contact electrodes and fixedly or detachably connected to an electrical stimulator. As shown, the cochlear electrode 1000 has four contact electrodes 1002, 1004, 1006, and 1008, though it will be appreciated that any number of contact electrodes is possible. As described elsewhere herein, the electrical stimulator can provide electrical signals to one or more such contact electrodes in response to an output from the signal processor according to the transfer function thereof and a received input signal.

Because each contact electrode 1002-1008 is in contact with the patient's cochlear tissue, each is separated from the "can" of the electrical stimulator (as well as the "cans" of other system components) via the impedance of the patient's tissue, shown as $R_{Body}$. Thus, if the circuitry within various system components did not have sufficiently high impedance (e.g., $R_{Can}$) to the component "can", electrical signals may stimulate undesired regions of the patient's cochlear tissue. For instance, stimulation intended for a particular contact electrode (e.g., 1002) may lead to undesired stimulation of other contact electrodes (e.g., 1004, 1006, 1008), reducing the overall efficacy of the system. Minimizing the conductive paths between system components (e.g., to the contact electrodes of a cochlear electrode) due to the patient's body, such as by incorporating impedances between component circuitry and the corresponding "can" via $R_{Can}$, can therefore improve the ability to apply an electrical stimulus to only a desired portion of the patient's body.

It will be appreciated that the term $R_{Body}$ is used herein to generally represent the resistance and/or impedance of the patient's tissue between various components and does not refer to a specific value. Moreover, each depiction or $R_{Body}$ in the figures does not necessarily represent the same value of resistance and/or impedance as the others.

Figure 11A:
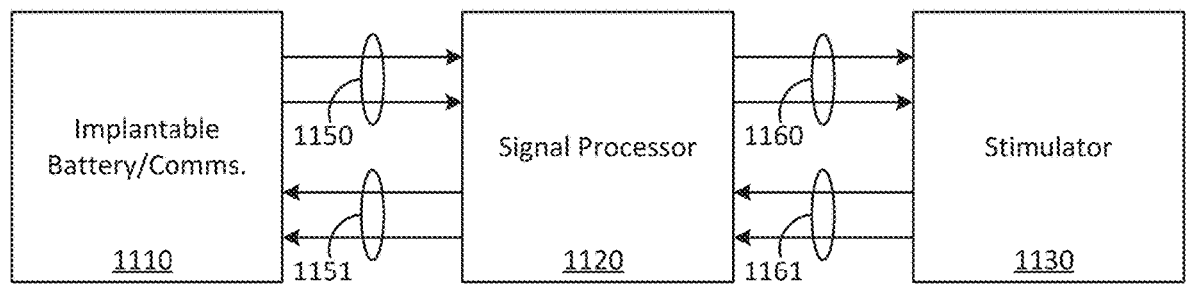
FIG. 11A shows a high level schematic diagram illustrating an exemplary communication configuration between an implantable battery and/or communication module, a signal processor, and a stimulator in an exemplary cochlear implant system.

FIG. 11A shows a high level schematic diagram illustrating an exemplary communication configuration between an implantable battery and/or communication module, a signal processor, and a stimulator. In the example of FIG. 11A, the implantable battery and/or communication module 1110 is in two-way communication with the signal processor 1120. For instance, the implantable battery and/or communication module 1110 can communicate power and/or data signals 1150 to the signal processor 1120. In some examples, the power and data signals 1150 can be included in a single signal generated in the implantable battery and/or communication module 1110 and transmitted to the signal processor 1120. Such signals can include, for example, a digital signal transmitted with a particular clock rate, which in some embodiments, can be adjustable, for example, via the implantable battery and/or communication module 1110.

In some embodiments, the signal processor 1120 can communicate information to the implantable battery and/or communication module 1110 (e.g., 1151), for example, feedback information and/or requests for more power, etc. The implantable battery and/or communication module 1110 can, in response, adjust its output to the signal processor 1120 (e.g., an amplitude, duty cycle, clock rate, etc.) in order to accommodate for the received feedback (e.g., to provide more power, etc.). Thus, in some such examples, the implantable battery and/or communication module 1110 can communicate power and data (e.g., 1150) to the signal processor 1120, and the signal processor 1120 can communicate various data back to the implantable battery and/or communication module 1110 (e.g., 1151).

In some embodiments, similar communication can be implemented between the signal processor 1120 and the stimulator 1130, wherein the signal processor 1120 provides power and data to the stimulator 1130 (e.g., 1160) and receives data in return from the stimulator 1130 (e.g., 1161). For example, the signal processor 1120 can be configured to output signals (e.g., power and/or data) to the stimulator 1130 (e.g., based on received inputs from a middle ear sensor or other device) via a similar communication protocol as implemented between the implantable battery and/or communication module 1110 and the signal processor 1120. Similarly, in some embodiments, the stimulator can be configured to provide feedback signals to the signal processor, for example, representative of an executed stimulation process. Additionally or alternatively, the stimulator may provide diagnostic information, such as electrode impedance and neural response telemetry or other biomarker signals.

Figure 11B:
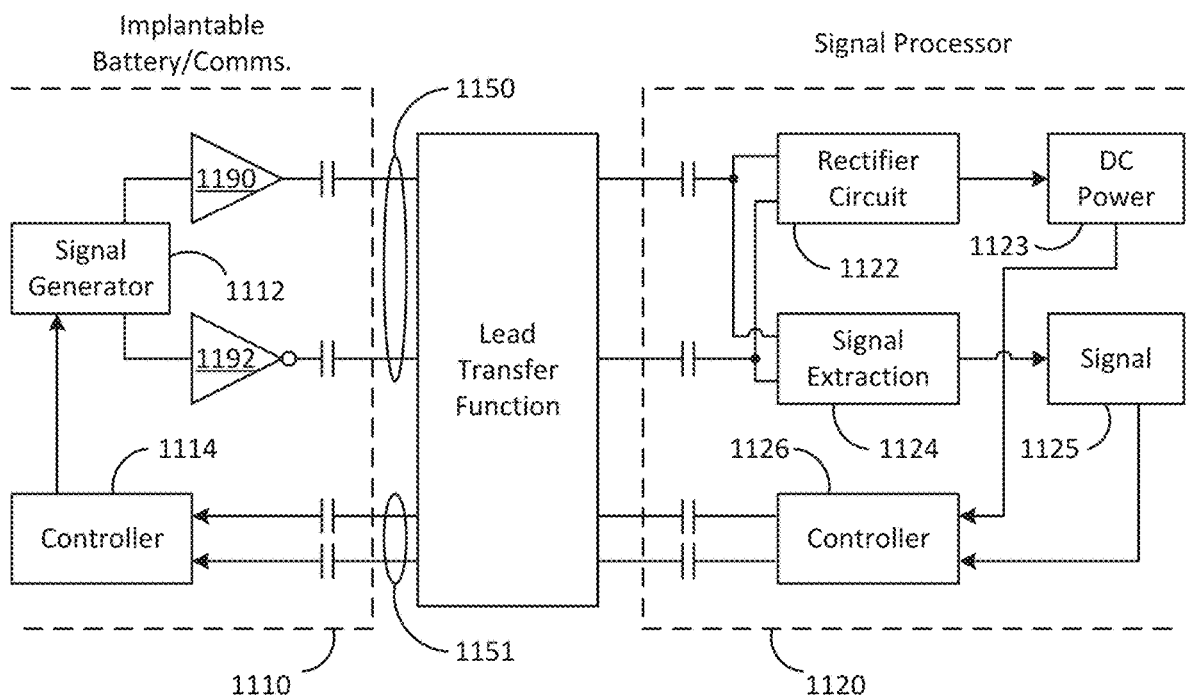
FIG. 11B is a schematic diagram illustrating exemplary electrical communication between an implantable battery and/or communication module and a signal processor in a cochlear implant system according to some embodiments.

FIG. 11B is a schematic diagram illustrating exemplary electrical communication between an implantable battery and/or communication module and a signal processor in a cochlear implant system according to some embodiments. In the illustrated embodiment, the implantable battery and/or communication module 1110 includes a signal generator 1112 configured to output a signal through a lead (e.g., 190) to the signal processor 1120. As described with respect to FIG. 11A, in some examples, the signal generator 1112 is configured to generate both data and power signals (e.g., 1150) for communication to the signal processor 1120. In some embodiments, the signal generator 1112 generates a digital signal for communication to the signal processor 1120. The digital signal from the signal generator 1112 can be communicated to the signal processor 1120 at a particular clock rate. In some examples, the signals are generated at approximately 30 kHz. In various examples, data and power frequencies can range from approximately 100 Hz to approximately 10 MHz, and in some examples, may be adjustable, for example, by a user.

In the illustrated embodiment, the implantable battery and/or communication module 1110 includes a controller in communication with the signal generator 1112. In some examples, the controller is capable of adjusting communication parameters such as the clock rate of the signal generator 1112. In an exemplary embodiment, the controller and/or the signal generator 1112 can communicate with, for example, a patient's external programmer (e.g., as shown in FIG. 1). The controller and/or signal generator 1112 can be configured to communicate data to the signal processor 1120 (e.g., 1151), such as updated firmware, signal processor 1120 transfer functions, or the like.

As shown, the signal generator 1112 outputs the generated signal to an amplifier 1190 and an inverting amplifier 1192. In some examples, both amplifiers are unity gain amplifiers. In some examples comprising digital signals, the inverting amplifier 1192 can comprise a digital NOT gate. The output from the amplifier 1190 and the inverting amplifier 1192 are generally opposite one another and are directed to the signal processor 1120. In some embodiments, the opposite nature of the signals output to the signal processor 1120 from amplifiers 1190 and 1192 results in a charge-neutral communication between the implantable battery and/or communication module 1110 and the signal processor 1120, such that no net charge flows through the wearer.

In the illustrated example of FIG. 11B, the receiving circuitry in the signal processor 1120 comprises a rectifier circuit 1122 that receives signals (e.g., 1150) from the amplifier 1190 and the inverting amplifier 1192. Since the output of one of the amplifiers 1190 and 1192 will be high, the rectifier circuit 1122 can be configured to receive the opposite signals from the amplifiers 1190 and 1192 and generate therefrom a substantially DC power output 1123. In various embodiments, the DC power 1123 can be used to power a variety of components, such as the signal processor 1120 itself, the middle ear sensor, the electrical and/or acoustic stimulator, or the like. The rectifier circuit 1122 can include any known appropriate circuitry components for rectifying one or more input signals, such as a diode rectification circuit or a transistor circuit, for example.

As described elsewhere herein, the implantable battery and/or communication module 1110 can communicate data to the signal processor 1120. In some embodiments, the controller and/or the signal generator 1112 is configured to encode the data for transmission via the output amplifiers 1190 and 1192. The signal processor 1120 can include a signal extraction module 1124 configured to extract the data signal 1125 from the signal(s) (e.g., 1150) communicated to the signal processor 1120 to produce a signal for use by the signal processor 1120. In some examples, the signal extraction module 1124 is capable of decoding the signal that was encoded by the implantable battery and/or communication module 1110. Additionally or alternatively, the signal extraction module 1124 can extract a signal 1125 resulting from the lead transfer function. In various examples, the extracted signal 1125 can include, for example, an updated transfer function for the signal processor 1120, a desired stimulation command, or other signals that affect operation of the signal processor 1120.

In the illustrated example, the signal processor 1120 includes a controller 1126 that is capable of monitoring the DC power 1123 and the signal 1125 received from the implantable battery and/or communication module 1110. The controller 1126 can be configured to analyze the received DC power 1123 and the signal 1125 and determine whether or not the power and/or signal is sufficient. For example, the controller 1126 may determine that the signal processor 1120 is receiving insufficient DC power for stimulating a cochlear electrode according to the signal processor 1120 transfer function, or that data from the implantable battery and/or communication module 1110 is not communicated at a desired rate. Thus, in some examples, the controller 1126 of the signal processor 1120 can communicate with the controller 1114 of the implantable battery and/or communication module 1110 and provide feedback regarding the received communication. Based on the received feedback from the controller 1126 of the signal processor 1120, the controller 1114 of the implantable battery and/or communication module 1110 can adjust various properties of the signal output by the implantable battery and/or communication module 1110. For example, the controller of the implantable battery and/or communication module 1110 can adjust the clock rate of the communication from the signal generator 1112 to the signal processor 1120.

In some systems, the transmission efficiency between the implantable battery and/or communication module 1110 and the signal processor 1120 is dependent on the clock rate of transmission. Accordingly, in some examples, the implantable battery and/or communication module 1110 begins by transmitting at an optimized clock rate until a change in clock rate is requested via the signal processor 1120, for example, to enhance data transmission (e.g., rate, resolution, etc.). In other instances, if more power is required (e.g., the controller of the signal processor 1120 determines the DC power is insufficient), the clock rate can be adjusted to improve transmission efficiency, and thus the magnitude of the signal received at the signal processor 1120. It will be appreciated that in addition or alternatively to adjusting a clock rate, adjusting an amount of power transmitted to the signal processor 1120 can include adjusting the magnitude of the signal output from the signal generator 1112. In some embodiments, for example, with respect to FIGS. 11A-B, power and data can be communicated, for example, from implantable battery and/or communication module 1110 to the signal processor 1120 at a rate of approximately 30 kHz, and can be adjusted from there as necessary and/or as requested, for example, by the signal processor 1120.

Figure 12A:
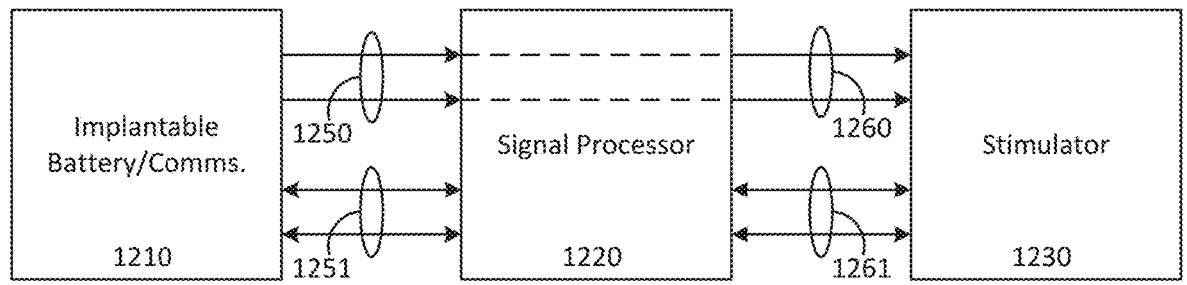
FIG. 12A is an alternative high-level schematic diagram illustrating an exemplary communication configuration between an implantable battery and/or communication module, a signal processor, and a stimulator.

FIG. 12A is an alternative high-level schematic diagram illustrating an exemplary communication configuration between an implantable battery and/or communication module, a signal processor, and a stimulator. In the example of FIG. 12A, the implantable battery and/or communication module 1210 provides signals (e.g., 1250) to the signal processor 1220 via a first communication link and is further in two-way communication for providing additional signals (e.g., 1251) with the signal processor 1220. In the example of FIG. 12A, the implantable battery and/or communication module 1210 can provide power signals (e.g., 1250) to the signal processor 1220 via a communication link and otherwise be in two-way data communication (1251) with the signal processor 1220 via a second communication link. In some such examples, the power (1250) and data (1251) signals can each include digital signals. However, in some embodiments, the power and data signals are transmitted at different clock rates. In some examples, the clock rate of the data signals is at least one order of magnitude greater than the clock rate of the power signals. For example, in an exemplary embodiment, the power signal is communicated at a clock rate of approximately 30 kHz, while the data communication occurs at a clock rate of approximately 1 MHz. Similarly to the embodiment described in FIG. 11A, in some examples, the clock rate can be adjustable, for example, via the implantable battery and/or communication module 1210.

As described with respect to FIG. 11A, in some embodiments, the signal processor 1220 can communicate information to the implantable battery and/or communication module 1210, for example, feedback information and/or requests for more power, etc. (e.g., data signals 1251). The implantable battery and/or communication module 1210 can, in response, adjust the power and/or data output to the signal processor 1220 (e.g., an amplitude, duty cycle, clock rate, etc.) in order to accommodate for the received feedback (e.g., to provide more power, etc.).

In some embodiments, similar communication can be implemented between the signal processor 1220 and the stimulator 1230, wherein the signal processor 1220 provides power and data to the stimulator 1230 and receives data in return from the stimulator 1230. For example, the signal processor 1220 can be configured to output signals power signals (e.g., 1260) and data signals (e.g., 1261) to the stimulator 1230 (e.g., based on received inputs from a middle ear sensor or other device). Such communication can be implemented via a similar communication protocol as implemented between the implantable battery and/or communication module 1210 and the signal processor 1220. In some examples, the power signals provided to the stimulator 1230 (e.g., 1260) are the same signals (e.g., 1250) received by the signal processor 1220 from the implantable battery and/or communication module 1210. Additionally, in some embodiments, the stimulator 1230 can be configured to provide feedback signals to the signal processor 1220 (e.g., 1261), for example, representative of an executed stimulation process.

Figure 12B:
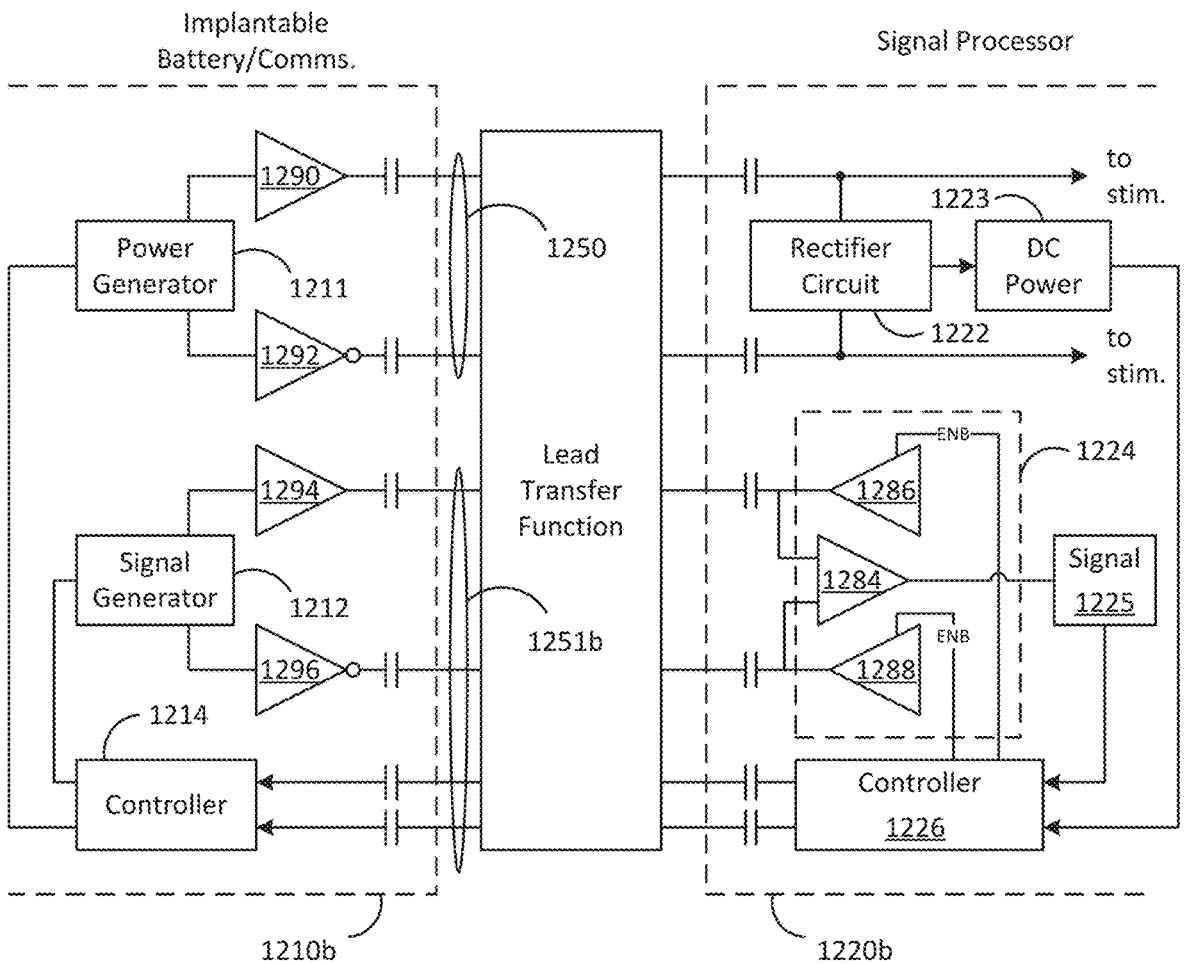
FIG. 12B is an alternative schematic diagram illustrating exemplary electrical communication between an implantable battery and/or communication module and a signal processor in a cochlear implant system similar to that shown in FIG. 12A.

FIG. 12B is an alternative schematic diagram illustrating exemplary electrical communication between an implantable battery and/or communication module 1210b and a signal processor 1220b in a cochlear implant system similar to that shown in FIG. 12A. In the illustrated embodiment of FIG. 12B, the implantable battery and/or communication module 1210b includes a power signal generator 1211 and a separate signal generator 1212. The power signal generator 1211 and signal generator 1212 are each configured to output a signal through a lead (e.g., 190) to the signal processor 1220b. In some embodiments, the power signal generator 1211 and the signal generator 1212 each generates digital signal for communication to the signal processor 1220b. In some such embodiments, the digital signal (e.g., 1250) from the power signal generator 1211 can be communicated to the signal processor 1220b at a power clock rate, while the digital signal (e.g., 1251b) from the signal generator 1212 can be communicated to the signal processor 1220b at a data clock rate that is different from the power clock rate. For instance, in some configurations, power and data can be communicated most effectively and/or efficiently at different clock rates. In an exemplary embodiment, the power clock rate is approximately 30 kHz while the data clock rate is approximately 1 MHz. Utilizing different and separately communicated power and data signals having different clock rates can increase the transfer efficiency of power and/or data from the implantable battery and/or communication module 1210b to the signal processor 1220b.

In the illustrated embodiment, the implantable battery and/or communication module 1210b includes a controller 1214 in communication with the power signal generator 1211 and the signal generator 1212. In some examples, the controller 1214 is capable of adjusting communication parameters such as the clock rate or content of the signal generator 1212 and/or the power signal generator 1211. In an exemplary embodiment, the controller 1214 and/or the signal generator 1212 or power signal generator 1211 can communicate with, for example, a patient's external programmer (e.g., as shown in FIG. 1). The controller 1214 and/or signal generator 1212 can be configured to communicate data to the signal processor 1220b, such as updated firmware, signal processor 1220b transfer functions, or the like. Additionally or alternatively, the controller 1214 can be configured to transmit signals such as audio or other signals streamed or otherwise received from one or more external devices as described elsewhere herein.

As shown, and similar to the example shown in FIG. 11B, the power signal generator 1211 outputs the generated signal to an amplifier 1290 and an inverting amplifier 1292. In some examples, both amplifiers are unity gain amplifiers. In some examples comprising digital signals, the inverting amplifier 1292 can comprise a digital NOT gate. The output from the amplifier 1290 and the inverting amplifier 1292 are generally opposite one another and are directed to the signal processor 1220b. In the illustrated example, the receiving circuitry in the signal processor 1220b comprises a rectifier circuit 1222 that receives signals from the amplifier 1290 and the inverting amplifier 1292. Since the output of one of the amplifiers 1290 and 1292 will be high, the rectifier circuit 1222 can be configured to receive the opposite signals from the amplifiers 1290 and 1292 and generate therefrom a substantially DC power output 1223.

In various embodiments, the DC power 1223 can be used to power a variety of components, such as the signal processor 1220b itself, the middle ear sensor, the electrical and/or acoustic stimulator 1230, or the like. The rectifier circuit 1222 can include any known appropriate circuitry components for rectifying one or more input signals, such as a diode rectification circuit or a transistor circuit, for example. In some embodiments, signals from the power signal generator 1211 are generated at a clock rate that is optimal for transmitting power through the lead (e.g., approximately 30 kHz). In the illustrated example of FIG. 12B, the rectifier circuit 1222 can be arranged in parallel with power lines that are configured to communicate power signals to other components within the system, such as the stimulator 1230, for example. For instance, in some embodiments, the same power signal (e.g., 1250) generated from the power signal generator 1211 and output via amplifiers 1290 and 1292 can be similarly applied to the stimulator 1230. In some such examples, the stimulator 1230 includes a rectifier circuit 1222 similar to the signal processor 1220b for extracting DC power from the power signal and the inverted power signal provided by amplifiers 1290 and 1292, respectively. In alternative embodiments, the signal processor 1220b can similarly provide signals from a separate power signal generator 1211 to provide power signals (e.g., at approximately 30 kHz) to the stimulator 1230 similar to how power is provided from the implantable battery and/or communication module 1210b to the signal processor 1220b in FIG. 12B.

In the example of FIG. 12B, the signal generator 1212 outputs a data signal (e.g., 1251b) to an amplifier 1294 and an inverting amplifier 1296. In some examples, both amplifiers are unity gain amplifiers. In some examples comprising digital signals, the inverting amplifier 1296 can comprise a digital NOT gate. The output from the amplifier 1294 and the inverting amplifier 1296 are generally opposite one another and are directed to the signal processor 1220b.

As described elsewhere herein, in some embodiments, the controller 1214 and/or the signal generator 1212 is configured to encode data for transmission via the output amplifiers 1294 and 1296. The signal processor 1220b can include a signal extraction module 1224 configured to extract the data from the signal(s) 1225 communicated to the signal processor 1220b to produce a signal 1225 for use by the signal processor 1220b. In some examples, the signal extraction module 1224 is capable of decoding the signal that was encoded by the implantable battery and/or communication module 1210b. Additionally or alternatively, the signal extraction module 1224 can extract a resulting signal 1225 resulting from the lead transfer function. In various examples, the extracted signal can include, for example, an updated transfer function for the signal processor 1220b, a desired stimulation command, or other signals that affect operation of the signal processor 1220b.

In the example of FIG. 12B, the signal extraction module 1224 includes a pair of tri-state buffers 1286 and 1288 in communication with signals output from the signal generator 1212. The tri-state buffers 1286 and 1288 are shown as having "enable" (ENB) signals provided by controller 1226 in order to control operation of the tri-state buffers 1286 and 1288 for extracting the signal from the signal generator 1212. Signals from the signal generator 1212 and buffered by tri-state buffers 1286 and 1288 are received by amplifier 1284, which can be configured to produce a signal 1225 representative of the signal generated by the signal generator 1212.

In some examples, communication of signals generated at the signal generator 1212 can be communicated to the signal processor 1220b at a clock rate that is different from the clock rate of the signals generated by the power signal generator 1211. For instance, in some embodiments, power signals from the power signal generator 1211 are transmitted at approximately 30 kHz, which can be an efficient frequency for transmitting power. However, in some examples, the signals from the signal generator 1212 are transmitted at a higher frequency than the signal from the power signal generator 1211, for example, at approximately 1 MHz. Such high frequency data transmission can be useful for faster data transfer than would be available at lower frequencies (e.g., the frequencies for transmitting the signal from the power signal generator 1211). Thus, in some embodiments, power and data can be communicated from the implantable battery and/or communication module 1210b to the signal processor 1220b via different communication channels at different frequencies.

Similar to the embodiment shown in FIG. 11B, in the illustrated example of FIG. 12B, the signal processor 1220b includes a controller 1226 that is in communication with the implantable battery and/or communication module 1210b. In some such embodiments, the controller 1226 in the signal processor 1220b is capable of monitoring the DC power 1223 and/or the signal 1225 received from the implantable battery and/or communication module 1210b. The controller 1126 can be configured to analyze the received DC power 1223 and the signal 1225 and determine whether or not the power and/or signal is sufficient. For example, the controller 1226 may determine that the signal processor 1220b is receiving insufficient DC power for stimulating a cochlear electrode according to the signal processor 1220b transfer function, or that data from the implantable battery and/or communication module 1210b is not communicated at a desired rate. Thus, in some examples, the controller 1226 of the signal processor 1220b can communicate with the controller 1214 of the implantable battery and/or communication module 1210b and provide feedback regarding the received communication. Based on the received feedback from the controller 1226 of the signal processor 1220b, the controller 1214 of the implantable battery and/or communication module 1210b can adjust various properties of the signals output by the power signal generator 1211 and/or the signal generator 1212.

In the illustrated example of FIG. 12B, bidirectional communication signals 1251b between the implantable battery and/or communication module 1210b and signal processor 1220b comprises signals from the amplifiers 1294 and 1296 in one direction, and communication from controller 1226 to controller 1214 in the other direction. It will be appreciated that a variety of communication protocols and techniques can be used in establishing bidirectional communication signals 1251b between the implantable battery and/or communication module 1210b and signal processor 1220b.

For example, in some embodiments, the implantable battery and/or communication module 1210b need not include amplifiers 1294 and 1296, and instead transmits a signal and not its inverse to the signal processor 1220b. In other examples, the signal processor includes amplifiers similar to 1294 and 1296, and outputs a signal and its inverse back to the implantable battery and/or communication module 1210b. Additionally or alternatively, in some embodiments, the signal generator 1212 can be integral with the controller 1214 and/or the signal extraction module 1224 can be integral with controller 1226, wherein controllers 1214 and 1226 can be in bidirectional communication via signal generator 1212 and/or the signal extraction module 1224. In general, the implantable battery and/or communication module 1210b and the signal processor 1220b can be in bidirectional communication for communicating data signals separate from the power signals provided by power signal generator 1211.

As described, separate communication channels for power (e.g., 1250) and data (e.g., 1251b) can be used for providing both power and data from the implantable battery and/or communication module 1210b and the signal processor 1220b. This can allow for separate data and power clocking rates in order to improve the power transmission efficiency as well as the data transmission efficiency and/or rate. Moreover, in some examples, if the bidirectional communication (e.g., 1251b) between the implantable battery and/or communication module 1210b and the signal processor 1220b fails (e.g., due to component failure, connection failure, etc.), data for communication from the implantable battery and/or communication module 1210b can be encoded in the power signals (e.g., 1250) from the power signal generator 1211 and transmitted to the signal processor

1220b. Thus, similar to the embodiment described with respect to FIG. 11B, both power and data can be transmitted via the same signal.

In some examples, the signal extraction module 1224 can be configured to receive data received from the power signal generator 1211, for example, via an actuatable switch that can be actuated upon detected failure of communication 1251b. In other examples, the signal extraction module 1224 and/or the controller 1226 can generally monitor data from the power signal generator 1211 and identify when signals received from the power signal generator 1211 include data signals encoded into the received power signal in order to determine when to consider the power signals to include data.

Accordingly, in some embodiments, the configuration of FIG. 12B can be implemented to establish efficient, bidirectional communication between the implantable battery and/or communication module 1210b and the signal processor 1220b. Failure in bidirectional communication 1251b can be identified manually and/or automatically. Upon detection of failure in the bidirectional communication 1251b, the controller 1214 can encode data into the power signal output from the power signal generator 1211, and power and data can be combined into a single signal such as described with respect to FIG. 11B.

Figure 12C:
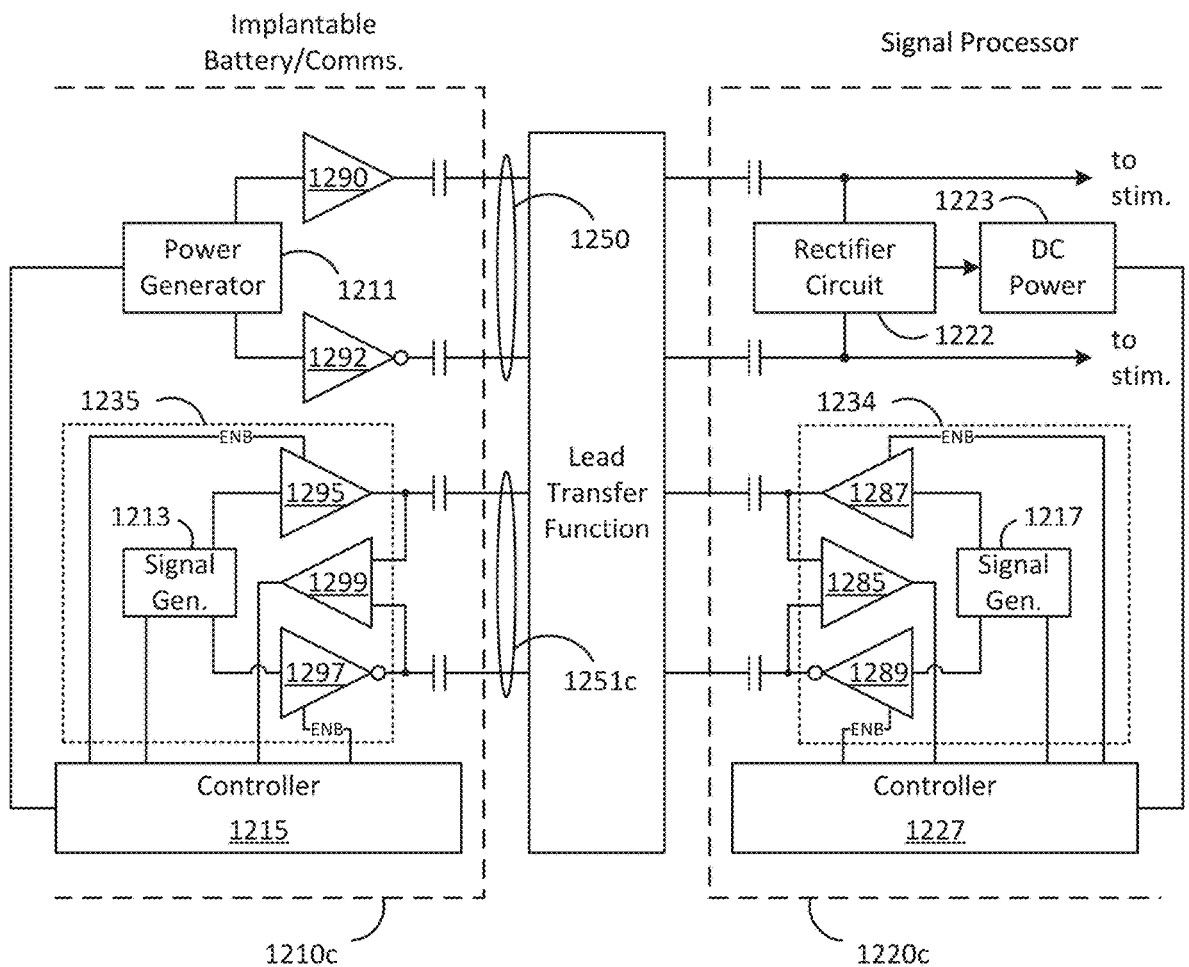
FIG. 12C is another alternative schematic diagram illustrating exemplary electrical communication between an implantable battery and/or communication module and a signal processor in a cochlear implant system similar to that shown in FIG. 12A.

FIG. 12C is another alternative schematic diagram illustrating exemplary electrical communication between an implantable battery and/or communication module 1210c and a signal processor 1220c in a cochlear implant system similar to that shown in FIG. 12A. Similar to the embodiment of FIG. 12B, in the illustrated embodiment of FIG. 12C, the implantable battery and/or communication module 1210c includes a power signal generator 1211 configured to output a signal through a lead (e.g., 190) to the signal processor 1220c. In some embodiments, the power signal generator 1211 generates a digital signal (e.g., 1250) for communication to the signal processor 1220c, for example, at a power clock rate. The power signal generator 1211 and corresponding amplifiers 1290, 1292, as well as rectifier circuit 1222, can operate similar to described with respect to FIG. 12B in order to extract DC power 1223 and, in some examples, output power signals to further system components, such as stimulator 1230.

In the illustrated embodiment, the implantable battery and/or communication module 1210c includes a signal generator 1213, which can be capable of providing data signals to the signal processor. In some embodiments, the signal generator 1213 generates a digital signal for communication to the signal processor 1220c. In some such embodiments, the digital signal (e.g., 1251c) from the signal generator 1213 can be communicated to the signal processor 1220b at a data clock rate that is different from the power clock rate. For instance, as described elsewhere herein, in some configurations, power and data can be communicated most effectively and/or efficiently at different clock rates. In an exemplary embodiment, the power clock rate is approximately 30 kHz while the data clock rate is approximately 1 MHz. Utilizing different and separately communicated power and data signals having different clock rates can increase the transfer efficiency of power and/or data from the implantable battery and/or communication module 1210c to the signal processor 1220c.

The embodiment of FIG. 12C includes a controller 1215 in communication with the power signal generator 1211 and the signal generator 1213. In some examples, the controller 1215 is capable of adjusting communication parameters such as the clock rate or content of the signal generator 1213 and/or the power signal generator 1211. In an exemplary embodiment, the controller 1215 and/or the signal generator 1213 or power signal generator 1211 can communicate with, for example, a patient's external programmer (e.g., as shown in FIG. 1). The controller 1215 and/or signal generator 1213 can be configured to communicate data to the signal processor 1220c, such as updated firmware, signal processor 1220c transfer functions, or the like.

Similar to the example in FIG. 12B, in the example of FIG. 12C, the signal generator 1213 outputs a data signal (e.g., 1251) to an amplifier 1295 and an inverting amplifier 1297. In some examples, both amplifiers are unity gain amplifiers. In some examples, amplifiers 1295, 1297 comprise tri-state buffers. In some examples comprising digital signals, the inverting amplifier 1297 can comprise a digital NOT gate. The output from the amplifier 1295 and the inverting amplifier 1297 are generally opposite one another and are directed to the signal processor 1220c.

As described elsewhere herein, in some embodiments, the controller 1215 and/or the signal generator 1213 is configured to encode data for transmission via the amplifiers 1295 and 1297. The signal processor 1220c can include a signal extraction module 1234 configured to extract the data from the signal(s) communicated to the signal processor 1220c to produce a signal for use by the signal processor 1220c. In some examples, the signal extraction module 1234 is capable of decoding the signal that was encoded by the implantable battery and/or communication module 1210c. Additionally or alternatively, the signal extraction module 1234 can extract a signal resulting from the lead transfer function. In various examples, the extracted signal can include, for example, an updated transfer function for the signal processor 1220c, a desired stimulation command, or other signals that affect operation of the signal processor 1220c.

In the example of FIG. 12C, similar to signal extraction module 1224 in FIG. 12B, the signal extraction module 1234 includes a pair of tri-state buffers 1287 and 1289 in communication with signals output from the signal generator 1213. The tri-state buffers 1287 and 1289 are shown as having "enable" (ENB) signals provided by controller 1227 in order to control operation of the tri-state buffers 1287 and 1289 for extracting the signal from the signal generator 1213. Signals from the signal generator 1213 and buffered by tri-state buffers 1287 and 1289 are received by amplifier 1285, which can be configured to produce a signal representative of the signal generated by the signal generator 1213.

As described elsewhere herein, in some examples, communication of signals generated at the signal generator 1213 can be communicated to the signal processor 1220c at a clock rate that is different from the clock rate of the signals generated by the power signal generator 1211. For instance, in some embodiments, power signals from the power signal generator 1211 are transmitted at approximately 30 kHz, which can be an efficient frequency for transmitting power. However, in some examples, the signals from the signal generator 1213 are transmitted at a higher frequency than the signal from the power signal generator 1211, for example, at approximately 1 MHz. Such high frequency data transmission can be useful for faster data transfer than would be available at lower frequencies (e.g., the frequencies for transmitting the signal from the power signal generator 1211). Thus, in some embodiments, power and data can be communicated from the implantable battery and/or communication module 1210c to the signal processor 1220c via different communication channels at different frequencies.

In the illustrated example of FIG. 12C, the signal processor 1220c includes a signal generator 1217 and controller 1227 that is in communication with the signal generator 1217. Similar to the operation of signal generator 1213 and amplifiers 1295 and 1299, the signal generator can be configured to produce output signals to buffers 1287 and 1289, which can be configured to output signals to the implantable battery and/or communication module 1210c.

In some embodiments, the controller 1227 in the signal processor 1220c is capable of monitoring the DC power 1223 and/or the signal received from the implantable battery and/or communication module 1210c. The controller 1126 can be configured to analyze the received DC power 1223 and the signal and determine whether or not the power and/or signal is sufficient. For example, the controller 1227 may determine that the signal processor 1220c is receiving insufficient DC power for stimulating a cochlear electrode according to the signal processor 1220c transfer function, or that data from the implantable battery and/or communication module 1210c is not communicated at a desired rate. Thus, in some examples, the controller 1227 of the signal processor 1220c cause the signal generator 1217 to generate communication signals to send to implantable battery and/or communication module 1210c. Such signals can be used to provide feedback regarding signals received by the signal processor 1220c, such as the DC power 1223.

In the example of FIG. 12C, amplifiers 1295 and 1297 are shown as including tri-state amplifiers (e.g., tri-state buffers) controllable by the controller 1227. Similar to the configuration in the signal processor 1220c, the implantable battery and/or communication module 1210c includes a signal extraction module 1235 configured to extract data from the signal(s) communicated to the implantable battery and/or communication module 1210c from signal generator 1217 of the signal processor 1220c. The signal extraction module 1235 includes amplifiers 1295 and 1297 (e.g., tri-state buffers) in communication with signals output from the signal generator 1217. Signals from the signal generator 1217 and received at amplifiers 1295 and 1297 are received by amplifier 1299, which can be configured to produce a signal representative of the signal generated by the signal generator 1217 to controller 1215 of the implantable battery and/or communication module 1210. Thus, in some embodiments, the controller 1227 of the signal processor 1220c is configured to communicate data back to the implantable battery and/or communication module 1210a via buffers 1287 and 1289.

As described with respect to other embodiments, based on the received feedback from the controller 1227 of the signal processor 1220c, the controller 1215 of the implantable battery and/or communication module 1210c can adjust various properties of the signals output by the power signal generator 1211 and/or the signal generator 1213.

Thus, in the illustrated example of FIG. 12C, bidirectional communication signal 1251 between the implantable battery and/or communication module 1210c and signal processor 1220c includes communication between different signal extraction modules 1235 and 1234. As shown, both the implantable battery and/or communication module 1210c and the signal processor 1220c include a controller (1215, 1227) that communicates with a signal generator (1213, 1217) for producing output signals. The signal generator (1213, 1217) outputs signals via tri-state amplifiers, including one inverting amplifier (1297, 1289) for communication across bidirectional communication 1251c for receipt by the other signal extraction module (1234, 1235).

Thus, in some embodiments, bidirectional communication 1251c between the implantable battery and/or communication module 1210c and the signal processor 1220c can be enabled by each of the implantable battery and/or communication module and the signal processor receiving and transmitting data via approximately the same communication structure as the other. In some such examples, the implantable battery and/or communication module 1210c and the signal processor 1220c include data extraction modules 1235 and 1234, respectively, configured both to output signals from a signal generator (e.g., via signal generator 1213 or signal generator 1217) and receive and extract signals (e.g., via amplifier 1285 and amplifier 1299).

In the example of FIG. 12C, amplifiers 1295 and 1297 comprise tri-state amplifiers that selectively (e.g., via "enable" control from controller 1215) output the signal from signal generator 1213, and amplifier 1297 is shown as an inverting amplifier. As described, in some examples, amplifiers 1295 and 1297 comprise tri-state buffers. Similarly, of tri-state buffers 1287 and 1289 that selectively (e.g., via "enable" control from controller 1227) output the signal from signal generator 1217, buffer 1289 is shown as an inverting amplifier. As described elsewhere herein, communicating a signal and its inverse (e.g., via 1295 and 1297) allows communication with no net charge flow between the implantable battery and/or communication module 1210c and the signal processor 1220c. Thus, bidirectional communication between the implantable battery and/or communication module 1210c and the signal processor 1220c can be performed without a net charge flow between the components.

As described elsewhere herein, power from power generator 1211 and data from signal generator 1213 (and/or signal generator 1217) can be communicated at different clocking rates to optimize power and data transfer. In some examples, if data communication (e.g., via bidirectional communication 1251c) fails, the controller 1215 can be configured to control power generator 1211 to provide both power and data signals via amplifiers 1290 and 1292, for example, as described with respect to FIG. 11B.

Accordingly, in some embodiments, the configuration of FIG. 12C can be implemented to establish efficient, bidirectional communication between the implantable battery and/or communication module 1210 and the signal processor 1220. Failure in bidirectional communication 1251 can be identified manually and/or automatically. Upon detection of failure in the bidirectional communication 1251, the controller 1215 can encode data into the power signal output from the power signal generator 1211, and power and data can be combined into a single signal such as described with respect to FIG. 11B.

As discussed elsewhere herein, different safety standards can exist regarding electrical communication within the patient's body. For example, safety standards can limit the amount of current that can safely flow through a patient's body (particularly DC current). As shown in FIGS. 11B, 12B, and 12C, each of the illustrated communication paths between the implantable battery and/or communication module and the signal processor are coupled to output capacitors. The capacitors positioned at the inputs and outputs of the implantable battery and/or communication module and the signal processor can substantially block DC current from flowing therebetween while permitting communication of AC signals.

As described elsewhere herein, in some embodiments, the data communicated between the implantable battery and/or communication module and the signal processor (e.g., from the signal generator) is encoded. In some such examples, the encoding can be performed according to a particular data encoding method, such as an 8*b*/10*b* encoding scheme, to achieve DC balance in the communicated signal. For example, in some embodiments, data is encoded such that the numbers of high and low bits communicated between components at each clock signal meet certain criteria to prevent a charge of a single polarity from building up on any of the capacitors. Such encoding can minimize the total charge that flows between the implantable battery and/or communication module and the signal processor during communication.

While described and illustrated as representing communication between the implantable battery and/or communication module and the signal processor, it will be appreciated that communication configurations such as shown in FIGS. 10, 11A, 11B, 12A, 12B, and 12C can be implemented between any pair of devices generally in communication with one another. For example, isolating circuitry (e.g., Roan) can be included in any of the system components (e.g., middle ear sensor, acoustic stimulator, electrical stimulator, etc.) to effectively isolate the ground signals from each component from its respective can. Similarly, the exemplary capacitive AC coupling with DC blocking capacitors and DC balancing encoding as described elsewhere herein can be incorporated as the communication interface between any two communicating components.

As described, data can be communicated from the implantable battery and/or communication module to the signal processor for a variety of reasons. In some examples, data is that communicated to the implantable battery and/or communication module from an external component, such as a programmer as shown in FIG. 1. In an exemplary process, a programmer, such as a clinician's computer, can be used to communicate with a patient's fully implanted system via a communication configuration such as shown in FIG. 11B, 12B, or 12C. For example, a programmer can communicate wirelessly (e.g., via Bluetooth or other appropriate communication technique) with the patient's implantable battery and/or communication module. Signals from the programmer can be sent from the implantable battery and/or communication module to the signal processor via the communication configurations of FIG. 11B, 12B, or 12C.

During such processes, a clinician can communicate with the signal processor, and, in some cases, with other components via the signal processor. For example, the clinician can cause the signal processor to actuate an electrical and/or an acoustic stimulator in various ways, such as using various electrical stimulation parameters, combinations of active contact electrodes, various acoustic stimulation parameters, and various combinations thereof. Varying the stimulation parameters in real time can allow the clinician and patient to determine effectiveness of different stimulation techniques for the individual patient. Similarly, the clinician can communicate with the signal processor to update transfer function. For example, the clinician can repeatedly update the transfer function signal processor while testing the efficacy of each one on the individual patient. In some examples, combinations of stimulation parameters and signal processor transfer functions can be tested for customized system behavior for the individual patient.

In some embodiments, various internal properties of the system may be tested. For instance, various impedance values, such as a sensor impedance or a stimulator impedance can be tested such as described in U.S. Patent Publication No. 2015/0256945, entitled TRANSDUCER IMPEDANCE MEASUREMENT FOR HEARING AID, which is assigned to the assignee of the instant application, the relevant portions of which are incorporated by reference herein.

Figure 12D:
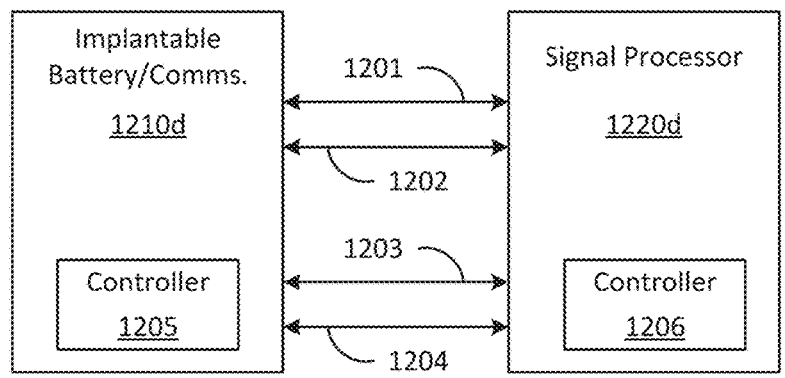
FIG. 12D is high-level schematic diagram illustrating exemplary electrical communication between an implantable battery and/or communication module and a signal processor in a cochlear implant system similar to that shown in FIG. 12A.

Additionally or alternatively, various characteristics of individual leads can be analyzed. FIG. 12D is high-level schematic diagram illustrating exemplary electrical communication between an implantable battery and/or communication module and a signal processor in a cochlear implant system similar to that shown in FIG. 12A. In the simplified example of FIG. 12D, conductors 1201, 1202, 1203, and 1204 extend between implantable battery and/or communication module 1210*d* and signal processor 1220*d*. In some examples, such conductors are included in a lead (e.g., lead 190) extending between the implantable battery and/or communication module 1210*d* and signal processor 1220*d*. In the example of FIG. 12D, implantable battery and/or communication module 1210*d* includes controller 1205 and signal processor 1220*d* includes controller 1206. Other internal components of the implantable battery and/or communication module 1210*d* and signal processor 1220*d* are not shown, though various configurations are possible, such as shown in FIG. 11B, 12B, or 12C.

In some embodiments, one or both of controllers 1205, 1206 can be configured to apply a test signal to one or more of conductors 1201, 1202, 1203, 1204 in order to test one or more properties of such conductors. In an exemplary test process, a controller (e.g., 1205) can drive a signal (e.g., a sine wave or other shaped wave) across a conductor (e.g., 1201) and measure the sent current and the voltage at which the current is sent. From this information, the controller can determine conductor impedance, including integrity of the conductor (e.g., whether or not the conductor is broken). Similarly, a controller can be configured to ground a second conductor (e.g., 1202) while driving the test signal across a test conductor (e.g., 1201) in order to measure one or more electrical parameters between the two conductors (e.g., capacitance, impedance, etc.).

During exemplary operation, a controller can be configured to apply a test signal to a first conductor (e.g., 1201) and ground a second conductor (e.g., 1202). The controller can be configured to apply a test signal at a plurality of frequencies (e.g., perform a frequency sweep) and measure impedance vs. frequency between the first conductor and the second, grounded conductor. In various examples, a controller can be configured to perform such tests using any two conductors 1201, 1202, 1203, 1204, to test for baseline values (e.g., when the system is in a known working condition) or to test for expected values (e.g., to compare to an established baseline). In different embodiments, the controller in the implantable battery and/or communication module 1210*d* (controller 1205) and/or the controller in the signal processor 1220*d* (controller 1206) can perform the grounding of one or more conductors and/or apply the test signal to one or more conductors.

In some embodiments, such test processes can be performed automatically, for example, according to a programmed schedule. Additionally or alternatively, such test processes can be initiated manually, for example, by a wearer or a clinician, via an external device such as via a programmer (e.g., 100) or charger (e.g., 102). The results of such processes can be stored in an internal memory for later access and analysis, and/or can output to an external device for viewing. In some examples, results and/or a warning can be output to an external device automatically in the event that one or more results deviates sufficiently from a baseline value. In various examples, sufficient variation from the baseline for triggering an output can be based on a percent variation from the baseline (e.g., greater than 1% deviation from be baseline, greater than 5% deviation, greater than 10% deviation, etc.). Additionally or alternatively, sufficient variation an include varying a certain number of standard deviations from the baseline (e.g., greater than one standard deviation, two standard deviations, etc.). In various embodiments, the amount of variation that triggers outputting the results and/or a warning is adjustable. Additionally or alternatively, such an amount can vary between different measurements.

In some embodiments, one or more actions may be performed in response to the results of such an analysis. For instance, in an exemplary embodiment described with respect to FIG. 12B, if a test reveals an unexpected impedance on one of the signal conductors (e.g., from amplifier 1294 or inverting amplifier 1296), such as an open circuit, the controller 1214 may be configured to change operation of the system. For instance, controller 1214 can be configured to adjust the output from power generator 1211 in order to provide both power and data signals from the power generator 1211, such as described with respect to the configuration in FIG. 11B. In some examples, the controller 1214 can be configured to transmit a signal to an external device signaling such a change in operation and/or alerting a wearer and/or clinician that one or more conductors may be damaged or otherwise not operational.

Figure 13A:
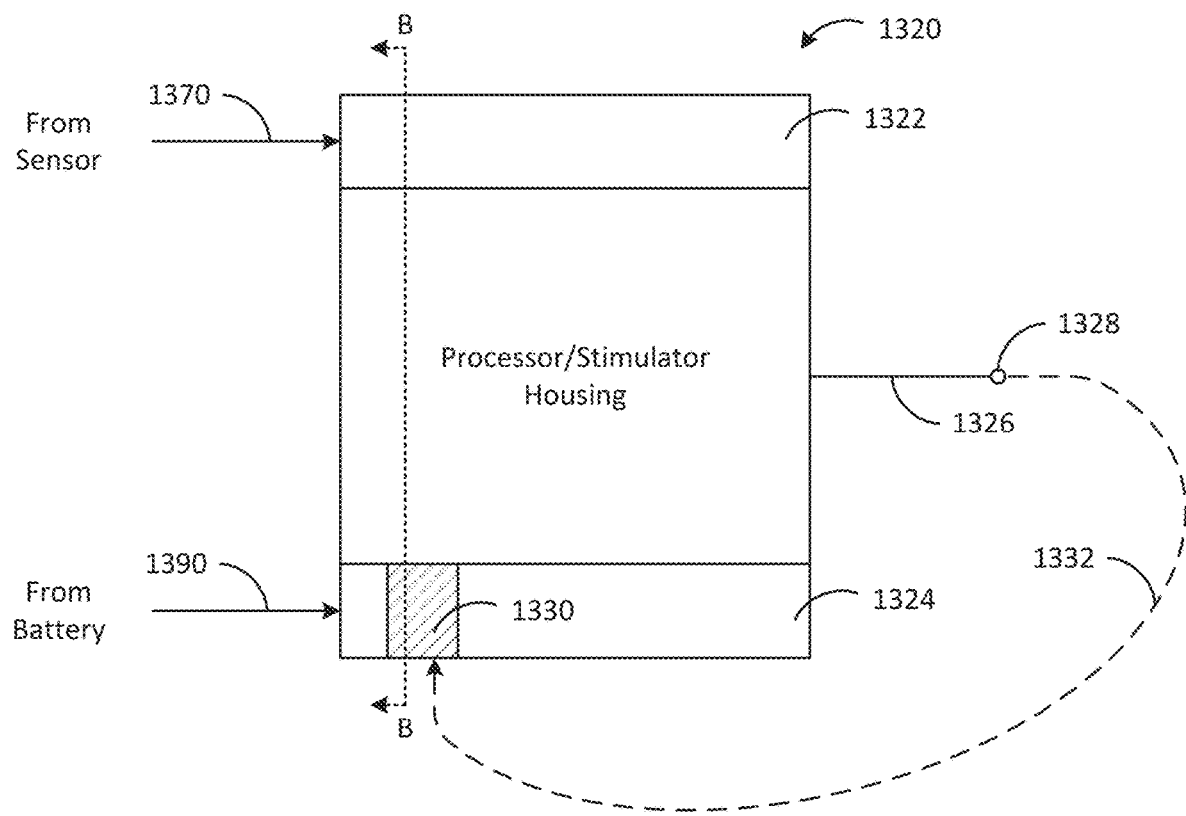
FIG. 13A shows an exemplary schematic illustration of processor and stimulator combined into a single housing.

While shown in several embodiments (e.g., FIGS. 1, 9, 11A, 12A) as being separate components connected by a lead (e.g., lead 180), in some examples, the processor (e.g., 120) and the stimulator (e.g., 130) can be integrated into a single component, for example, within a hermetically sealed housing. FIG. 13A shows an exemplary schematic illustration of processor and stimulator combined into a single housing. In the example of FIG. 13A, the processor/stimulator 1320 receives signal inputs from the sensor (e.g., a middle ear sensor) via lead 1370 and power from a battery (e.g., the implantable battery and/or communication module) via lead 1390. The processor/stimulator 1320 can include headers 1322, 1324 for receiving leads 1370, 1390, respectively.

The processor/stimulator 1320 can be configured to receive an input signal from the sensor, process the received input signal according to a transfer function, and output a stimulation signal via electrode 1326. Electrode 1326 can include one or more contact electrodes (e.g., 1328) in contact with a wearer's cochlear tissue to provide electrical stimulation thereto, for example, as described with respect to FIG. 10B.

The processor/stimulator 1320 of FIG. 13 includes a return electrode 1330 for providing a return path (e.g., 1332) for stimulation signals emitted from electrode 1326. The return electrode 1330 can be electrically coupled to a ground portion of circuitry within the processor/stimulator 1320 to complete a circuit comprising circuitry within the processor/stimulator 1320, the electrode 1326, the wearer's cochlear tissue, and ground. In some examples, the return electrode 1330 comprises an electrically conductive material in electrical communication with circuitry inside the processor/stimulator 1320, while the rest of the housing of the processor/stimulator 1320 is generally not electrically coupled to internal circuitry.

In some embodiments, the return electrode 1330 and the housing of the processor/stimulator 1320 comprise electrically conductive materials. For instance, in some examples, the housing comprises titanium while the return electrode 1330 comprises platinum or a platinum alloy. Header 1324 can generally include a non-conductive biocompatible material, such as a biocompatible polymer. The non-conductive header 1324 can provide isolation between the return electrode 1330 and the conductive housing of the processor/stimulator 1320.

While shown in FIG. 13A as being positioned in the power header 1324 of the processor/stimulator 1320, in general, the return electrode 1330 can be positioned anywhere on the exterior surface of the processor/stimulator 1320. In some examples, one or more redundant return electrodes can be included, for example, at or near the interface of the housing and the electrode 1326. In some examples, a return electrode can be positioned on a proximal end of the electrode 1326 itself. In some embodiments having a plurality of return electrodes (e.g., return electrode 1330 and a return electrode on the proximal end of electrode 1326), a switch can be used to select which return electrode is used. Additionally or alternatively, a plurality of return electrodes can be used simultaneously.

Figure 13B:
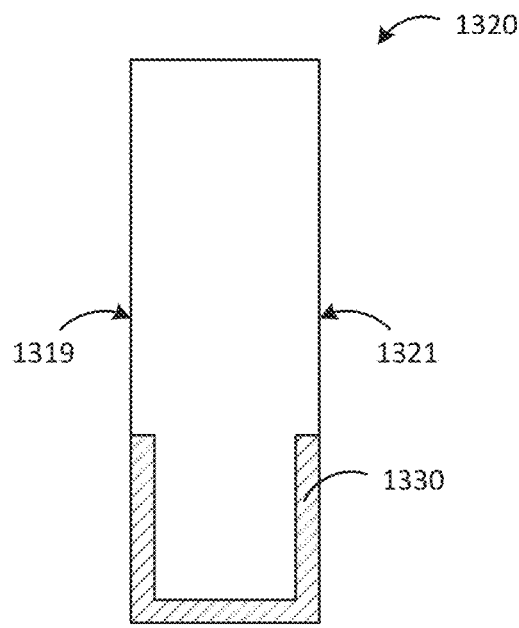
FIG. 13B shows a simplified cross-sectional view of the processor/stimulator shown in FIG. 13A taken along lines B-B.

FIG. 13B shows a simplified cross-sectional view of the processor/stimulator shown in FIG. 13A taken along lines B-B. As shown in FIG. 13B, processor/stimulator 1320 includes a housing having a first side 1319 and a second side 1321 and a return electrode 1330 embedded in the housing. Return electrode 1330 can comprise a conductive material suitable for contact with a wearer's tissue, such as platinum. In the illustrated example, the return electrode 1330 wraps around to both sides of the housing of the processor/stimulator 1320 so that the return electrode 1330 is coupled to the outer surface of the housing on the first side 1319 and the second side 1321.

This can facilitate implanting onto either side of a wearer's anatomy, since in some cases, only one side of the processor/stimulator electrically contacts conductive tissue of the wearer while the other side contacts, for instance, the skull of the wearer, and does not easily provide the return path (e.g., 1332). Thus, a single processor/stimulator design can be implanted in either side of a wearer's anatomy while providing an adequate return path via a return electrode 1330.

In various examples, the return electrode 1330 can extend around a perimeter edge of the processor/stimulator 1320, as shown in FIG. 13B. In other examples, the return electrode 1330 can include sections on either side of the housing and can be connected to one another internally within the housing rather than via a wrap-around contact. Additionally, while shown as being embedded in the housing of the processor/stimulator 1320, in some examples, return electrode 1330 can protrude outwardly from the housing. Return electrode 1330 can generally be any of a variety of shapes and sizes while including an electrical contact section on opposing sides of the housing to provide usability on either side of a wearer's anatomy. In other embodiments, return electrode can be positioned only one side of the housing for a customized right-side or left-side implementation.

As described elsewhere herein, in various embodiments, the processor generally receives an input signal, processes the signal, and generates a stimulation signal, which can be applied via an integrated stimulator (e.g., via a processor/stimulator such as in FIGS. 13A and 13B) or a separate stimulator in communication with the processor (e.g., as shown in FIGS. 1 and 9). In some such embodiments, the input signal received via the signal processor is generated by an implantable sensor, such as a middle ear sensor (e.g., as described with respect to FIGS. 4 and 5).

However, such sensors often measure or otherwise receive some stimulus that is converted into an output that is read and processed by the signal processor. For example, some middle ear sensors may produce a different output signal for a given stimulus depending on a variety of factors, such as variability in a wearer's inner-ear anatomy and motion. Thus, the output of a sensor for a given input may be not predictable while designing a system, especially across a range of frequencies.

FIG. 14A is a schematic diagram showing an exemplary signal processing configuration for normalizing a stimulus signal and adapting to variability in a sensor frequency response. FIG. 14B shows an exemplary gain vs. frequency response curve for signals at various stages in the processing configuration. "Gain" associated with a particular frequency, as used with respect to FIG. 14B, refers to a relationship (e.g., a ratio) between the magnitude of an input stimulus received by the sensor and processor and the magnitude of the resulting signal at various stages of processing. In the illustrated example, the processor/stimulator 1400 receives an input signal 1405 from the sensor.

As shown in FIG. 14B, the gain is very uneven over the distribution of frequencies shown in the plot. For instance, according to the illustrated example, a stimulus signal received at the sensor at 1 kHz will result in a much larger magnitude in signal 1405 compared to a stimulus signal of the same magnitude received at the sensor at 10 kHz. Such a discrepancy in frequency response can make signal processing difficult. Moreover, such frequency response in general may vary from person to person, or over the course of a wearer's lifetime due to physical movement of a sensor or anatomical changes.

The input signal 1405 undergoes analog processing 1410 to produce an analog processed signal 1415. As shown in FIG. 14B, the analog processing step 1410 improves the consistency of the gain across the range of frequencies, as the analog processed signal 1415 provides a flatter frequency response curve than does the input signal 1405. In some embodiments, the analog processing can include one or more filters and/or amplifiers generally configured to flatten out the frequency response curve as shown in FIG. 14B. In some examples, the analog processing components 1410 within the processor/stimulator 1400 can be substantially the same across various implantable systems in order to provide a first order correction of the frequency response. In other examples, an analog processing configuration 1410 can be customized to the wearer, for example, based on known anatomical features, measurements, analysis, or the like.

The analog processed signal 1415 undergoes a digital processing step 1420 to produce a digitally processed signal 1425. As shown in FIG. 14B, the digital processing step 1420 further improves the consistency of the gain across the range of frequencies, as the digitally processed signal 1425 provides a flatter frequency response curve than does the analog processed signal 1415. In some embodiments, the digital processing 1420 can be configured to substantially flatten the frequency response to correct remaining frequency response inconsistencies in the analog processed signal 1415. For instance, in some embodiments, after digital processing 1420, a stimulus signal of a given magnitude at a first frequency and a second frequency will result in a digitally processed signal 1425 having the same magnitude at the first and the second frequencies. Thus, the digitally processed signal 1425 corresponds to a normalized stimulus signal, reducing or eliminating the variability that comes with different wearer anatomies and wearer motion and/or changes over time. Having a normalized frequency response across large frequency ranges can simplify assessment of the efficacy of the implanted system, programming a signal processor transfer function, assessing system operation, and the like. In some examples, a flat frequency response can enable the system to present an electrical stimulus to the wearer at appropriate intensity levels, for example, with respect to received external acoustic stimuli, independent of the frequency content of the external acoustic stimuli.

In some embodiments, the digital processing 1420 can be customized via a calibration process after the system has been implanted. In an exemplary calibration process, a clinician or other user may provide a series of stimulus signals, for instance, at a plurality of frequencies and having like amplitudes, to be "picked up" by the sensor, which generates an input signal 1405 for each received signal. The clinician or other user may then sample the resulting analog processed signal 1415 and/or an initial digitally processed signal 1425 at the plurality of frequencies to determine the remaining non-uniformity in gain across the frequency sweep. The digital processing 1420 can be either established or updated to compensate for non-uniformities in order to establish a substantially flat frequency response curve in the digitally processed signal 1425. In some examples, a plurality of signals having different frequencies are provided in sequence and a magnitude response (e.g., gain) at each frequency is determined. After determining such a magnitude response, the digital processing stage 1420 can be updated based on the response vs. frequency relationship in order to flatten the frequency response curve.

In an alternate process, a white noise signal can be provided to be "picked up" by the sensor. A transform (e.g., a Fast Fourier Transform, or FFT) of the signal can be performed in order to extract the frequency content of the signal. The extracted frequency content can used to determine a magnitude response at each frequency and the digital processing 1420 can be updated to flatten the frequency response similar to described above.

In the illustrated example of FIG. 14A, the digitally processed signal 1425 (e.g., having a uniform gain across a frequency range with respect to input signals received from the sensor) is processed according to the signal processor transfer function 1430 to generate a stimulation signal 1435. Stimulation signal 1435 can be received by the stimulator 1440, which can apply an electrical signal 1445 to the electrode such as described elsewhere herein.

In some examples, the digital processing step 1420 to provide a uniform frequency response can be incorporated into the transfer function 1430 wherein the analog processed signal 1415 is digitally processed to both flatten the frequency response and to generate a stimulation signal (e.g., 1435) according to a programmed transfer function. Additionally or alternatively, as described elsewhere herein, in some examples, stimulator 1440 can be located external to the processor rather than being combined as a single processor/stimulator component 1400.

As described elsewhere herein, while many examples show a middle ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function.

Figure 15:
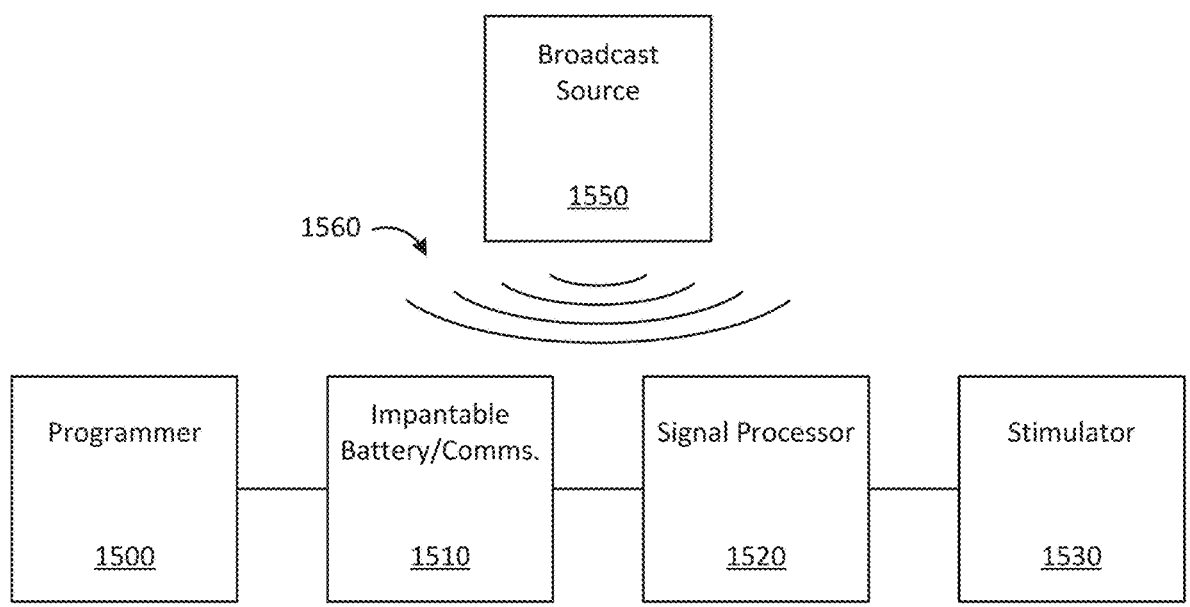
FIG. 15 is a process flow diagram illustrating an exemplary process for establishing a preferred transfer function for a patient.

Additionally or alternatively, one or more system components can be configured to receive broadcast signals for converting into stimulation signals. FIG. 15 is a schematic system diagram showing an implantable system configured to receive broadcast signals from a broadcast device. As shown in the example of FIG. 15, a broadcast source 1550 broadcasts a signal via communication link 1560. The communication link 1560 can include communication via a variety of communication protocols, such as Wi-Fi, Bluetooth, or other known data transmission protocols. Broadcast source 1550 can include any of a variety of components, such as a media source (e.g., television, radio, etc.), communication device (e.g., telephone, smartphone, etc.), a telecoil or other broadcast system (e.g., at a live performance), or any other source of audio signals that can be transmitted to an implanted system or to an external component of an implanted system (e.g., a system programmer, etc.).

An implantable system including a programmer 1500, an implantable battery and/or communication module 1510, a signal processor 1520, and a stimulator 1530 can generally receive the data from the broadcast source 1550 via communication link 1560. In various embodiments, any number of components in the implantable system can include a receiving device, such as a telecoil, configured to receive broadcast signals for eventual conversion into stimulation signals.

For instance, in some embodiments, programmer 1500 can include a telecoil relay configured to receive broadcast telecoil signals from a broadcast source 1550. The programmer can be configured to subsequently communicate a signal representative of the received broadcast signal to the implantable battery and/or communication module 1510 and/or the signal processor 1520, e.g., via a Bluetooth communication. If the communication is received from the programmer 1500 via the implantable battery and/or communication module 1510, the implantable battery and/or communication module 1510 can communicate the signal to the signal processor, for example, as described in any of FIG. 11A, 11B, 12A, or 12C.

In some such embodiments, the signal processor 1520 can be configured to receive such signals from the implantable battery and/or communication module 1510 and output stimulation signals to the stimulator 1530 based on the received signals and the signal processor transfer function. In other examples, the signal processor 1520 can include a telecoil relay or other device capable of receiving broadcast signals from the broadcast source 1550. In some such embodiments, the signal processor 1520 processes the received signals according to the signal processor transfer function and outputs stimulations signals to the stimulator 1530.

In some embodiments, the signal processor 1520 can be in communication with a plurality of input sources, such as, for example, a combination of an implanted microphone, a middle ear sensor, and a broadcast source 1550 (e.g., via the implantable battery and/or communication module 1510). In some such examples, the signal processor can be programmed with a plurality of transfer functions, each according to respective input sources. In such embodiments, the signal processor can identify which one or more input sources are providing input signals and process each such input signal according to the transfer function associated with its corresponding input source.

In some examples, a signal processor 1520 receiving a plurality of input signals from a corresponding plurality of input sources effectively combines the signals when producing a stimulation signal to the stimulator 1530. That is, in some embodiments, input sources are combined to form the stimulation signal from the signal processor 1520. In some such examples, a user may be able to mix the various received input signals in any way desired. For example, a user may choose to blend a variety of different input streams, such as an input from a middle ear sensor or other implanted device, a signal received from an external device (e.g., a telecoil relay, a Bluetooth connection such as to a smartphone, etc.), and the like. In an exemplary configuration, a user may elect to equally blend two input sources such that the stimulation signal is based 50% on a first input source and 50% on a second input source.

Additionally or alternatively, a user may elect to effectively "mute" one or more input sources so that the signal processor 1520 outputs stimulations signals based on input signals received from unmuted sources. Similarly, a user may be able to select a single source from which to process received input signals. For example, in some embodiments, a user may select to have signals received from broadcast source 1550 processed and converted into stimulation signals while having signals received from, for example, a middle ear sensor, disregarded.

In some examples, direct communication with the signal processor can be used to test the efficacy of a given signal processor transfer function and associated stimulation (e.g., acoustic or electrical) parameters. For example, the programmer can be used to disable input signals from a middle ear sensor or other input source and provide a customized signal to the signal processor to simulate a signal from the input source. The signal processor processes the received signal according to its transfer function and actuates the electrical stimulator and/or the acoustic stimulator accordingly. The processor can be used to test a variety of customized "sounds" to determine the efficacy of the signal processor transfer function for the given patient for each "sound."

Figure 16:
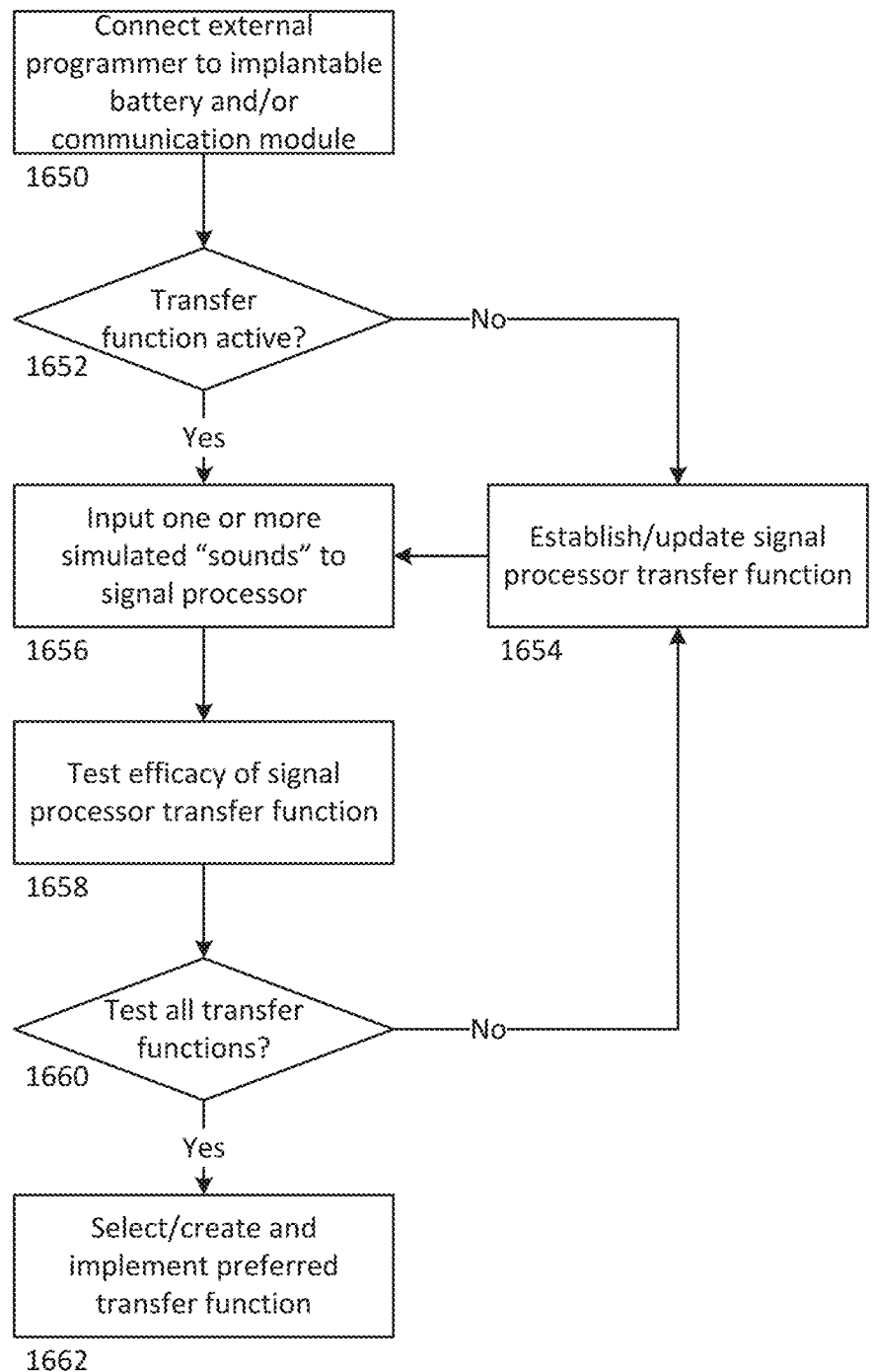
FIG. 16 is a process flow diagram illustrating an exemplary process for establishing a preferred transfer function for a patient.

FIG. 16 is a process flow diagram illustrating an exemplary process for establishing a preferred transfer function for a patient. The method can include connecting an external programmer to the implantable battery and/or communication module (step 1650). Connecting can include, for example, establishing a wireless connection (e.g., Bluetooth communication) between an external programmer and the implantable battery and/or communication module. The external programmer can include any variety of components capable of providing programming instructions to the implantable battery and/or communication module, such as a computer, smartphone, tablet, or the like.

Once communication is established, if there is no signal processor transfer function active (step 1652), a signal processor transfer function can be established (step 1654). If a transfer function is already active, or after one has been established (step 1654), the programmer can be used to input one or more simulated "sounds" to the signal processor. Such "sounds" can be received and treated by the signal processor as if they were received from an input source such as a middle ear sensor. The "sounds" can be, for example, computer-generated signals designed to simulate various input signals, such as a range of frequencies, phonetic sounds, or other distinguishable sound characteristics.

The process can further include testing the efficacy of the signal processor transfer function (step 1658). This can include, for example, determining how well the patient responds to each sound provided a given signal processor transfer function. In some examples, this can include rating the transfer function under test for each of the "sounds" and determining an aggregate score for the transfer function based on the score(s) associated with the one or more "sounds."

After testing the efficacy of the signal processor transfer function, if not all desired transfer functions have been tested (step 1660), the signal transfer function can be updated (step 1654). The one or more simulated "sounds" can be input to the signal processor (step 1656) and processed according to the updated transfer function, and the efficacy of the updated transfer function can be tested (step 1658). Once all desired transfer functions have been tested (step 1660), a signal processor transfer function for the user can be created or selected and implemented for the patient (step 1662). In some examples, a best transfer function of the tested transfer functions is selected based on a user preference, a highest score, or other metric. In other examples, composite results from the tested transfer functions can be combined to create a customized transfer function for the patient.

In other examples, rather than continually updating the signal processor transfer function, simulated "sounds" can be pre-processed outside of the signal processor, for example, on site with a clinician or audiologist. For instance, in an exemplary process, one or more simulated sounds can be pre-processed using processing software to establish simulated stimulation signals that would result from a particular input signal being processed via a particular transfer function. In some examples, such signals can be transferred to, for example, the signal processor for directly applying stimulation signals to the wearer.

Communication to the stimulator can be performed, for example, directly from various system components, such as a programmer. In other examples, such communication can be performed via the implantable battery and/or communication module and signal processor. For instance, in an exemplary embodiment, pre-processed signals can be communicated to the implantable battery and/or communication module via a wireless (e.g., Bluetooth) communication. The implantable battery and/or communication module can communicate the pre-processed signals to the signal processor, which can be configured with a unity transfer function. Thus, the signal processor merely passes the pre-processed signals on to the stimulator for performing stimulation.

Figure 17:
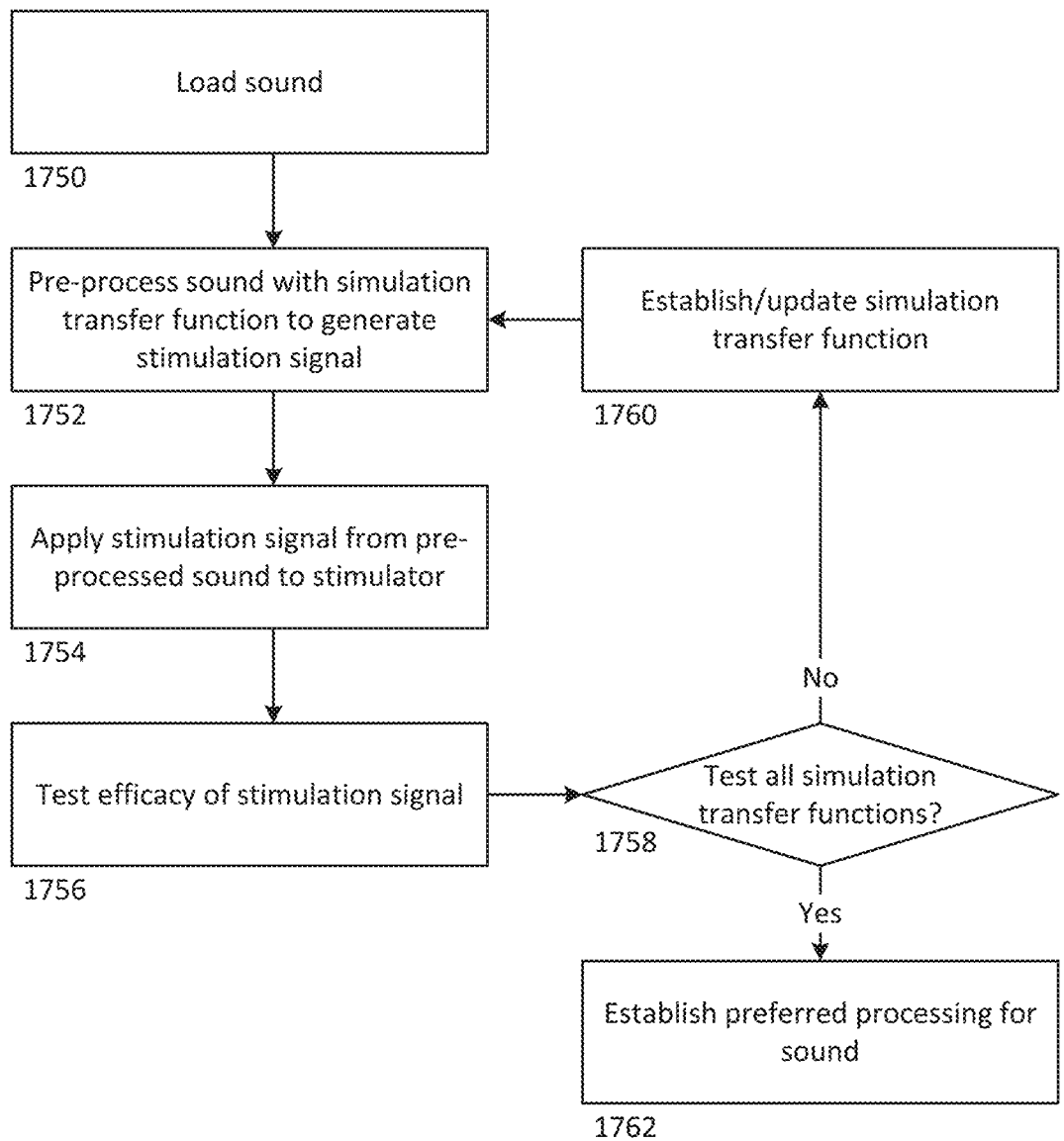
FIG. 17 is a process flow diagram showing an exemplary method of testing the efficacy of one or more sounds using one or more transfer functions via pre-processed signals.

FIG. 17 is a process flow diagram showing an exemplary method of testing the efficacy of one or more sounds using one or more transfer functions via pre-processed signals. In the method of FIG. 17, a sound can be loaded (step 1750), for example, into an application or processing software capable of processing the received sound. In some examples, the sound can be a simulated sound, such as a computer-generated signal representing a desired sound. In other examples, the sound can include a recording of an actual sound, such as a person's voice or other stimulus. The loaded sound can be pre-processed according to a transfer function to generate a stimulation signal (step 1752). The pre-processing can be performed, for example, on a stand-alone work station, a system programmer, or the like.

The method of FIG. 17 further comprises the step of applying the stimulation signal from the pre-processed sound to the stimulator of the implanted system (step 1754). As described elsewhere herein, such communication of the stimulation signal to the stimulator can be performed in a variety of ways, such as directly to the stimulator (e.g., from an external workstation, the user's programmer, etc.) or through the signal processor.

Upon applying the stimulation signal (step 1754), the method can further include the step of testing the efficacy of the stimulation signal (step 1756). This can include, for example, testing a user's comprehension of the initial sound from the received stimulation signal, receiving a rating score from the user, or any other appropriate way of resting the efficacy of the stimulation signal. Since the stimulation signal applied in step 1754 is based on the sound and the transfer function used for pre-processing, testing the efficacy of the stimulation signal is similar to testing the efficacy of the transfer function for the given sound.

After testing the efficacy of the stimulation signal, it can be determined whether all simulation transfer functions have been tested for the given sound (step 1758). If not, the method can include the step of establishing or updating a simulated transfer function (step 1760), and repeating the steps of pre-processing the sound to establish a stimulation signal (step 1752), applying the stimulation signal (step 1754), and testing the efficacy of the stimulation signal (step 1756) all according to the updated transfer function. Thus, a given sound can be processed according to a plurality of transfer functions, and a plurality of corresponding stimulation signals can be tested with respect to a given user. If all simulation transfer functions have been tested at step 1758, the process can include establishing a preferred processing for the sound (step 1762).

In some examples, the process of FIG. 17 can be performed in real time. For instance, in some embodiments, a device in communication with the stimulator in an implanted system (e.g., directly via wireless communication with the stimulator or indirectly via signal processor) can cycle through various simulated transfer functions while pre-processing sound signals prior to communicating them to the user's system. In some such examples, after establishing a preferred processing technique (e.g., simulated transfer function) for a given sound (e.g., in step 1762), the user's signal processor transfer function can be updated to reflect the preferred transfer function for the given sound.

Additionally or alternatively, the process of FIG. 17 can be repeated for a plurality of different sounds. In some embodiments, a plurality of sounds can be pre-processed according to a plurality of different simulated transfer functions, and the resulting generated stimulation signals can be stored in a database. A testing device, such as a workstation, programmer, etc., can be used to carry out the method of FIG. 17 while using the database of stimulations signals to test the efficacy of various transfer functions with respect to various sounds for a user.

In some examples, such a database can be used to fit a user with a particular implant system. For example, stimulation signals generated by pre-processing a plurality of sounds can be communicated to the implanted stimulator of a user having an implanted stimulator and cochlear electrode in order to test the efficacy of the transfer function simulated in the pre-processing. In various examples, a plurality generated stimulation signals associated with a given sound can be applied to the stimulator until a preferred simulated transfer function is established. In other examples, generated stimulation signals representative of a plurality of sounds can be established for each of a plurality of transfer functions, such that each transfer function can be tested on a user for a plurality of sounds prior to testing another transfer function.

FIG. 18 is a schematic representation of an exemplary database of pre-processed sound signals. As shown, the database is represented as a table having n rows corresponding to different sounds (sound 1, sound 2, . . . , sound n) and m columns corresponding to different simulated transfer functions (simulated transfer function 1, simulated transfer function 2, . . . , simulated transfer function m). As shown, at the intersection of each row (i) and each column (j), pre-processing a sound i with a simulated transfer function j results in stimulation signal (i,j). In some embodiments, a table such of stimulation signals generated from pre-processed sounds such as shown in FIG. 18 can be stored in a database of pre-processed sound signals for device fitting for a user.

As described elsewhere herein, in various fitting processes, a sound may be selected from database (e.g., sound 1), and a plurality of different stimulation signals (e.g., stimulation signal (1,1), stimulation signal (1,2), . . . , stimulation signal (1,m)) can be communicated to an implanted stimulator. Such stimulation signals generally correspond to the result of the sound (e.g., sound 1) being pre-processed according to various simulated transfer functions (1-m). As described with respect to FIG. 17, a preferred stimulation signal (and thus, a preferred corresponding simulated transfer function) can be established for the given sound (e.g., sound 1). A similar process can be repeated for each sound in the database. In various examples, one or more signal processor transfer functions can be communicated to the signal processor based on the determined preferred simulated transfer function(s). For instance, in some example, the simulated transfer function that was preferred among the most sounds may be implemented as the signal processor transfer function. In other embodiments, the signal processor includes a plurality of transfer functions, and can apply different transfer functions to different detected sounds depending on the preferred transfer function for each sound.

In other exemplary fitting processes, a plurality of stimulation signals (e.g., stimulation signal (1,1), stimulation signal (2,1), . . . , stimulation signal (n,1)) corresponding to a single simulated transfer function (e.g., simulated transfer function 1) can be applied to a stimulator. Such stimulation signals correspond to a plurality of sounds that are pre-processed according to the single simulated transfer function. This can be used to test the efficacy of the selected transfer function. The process can be repeated for a plurality of simulated transfer functions (e.g., 2-m) in order to determine a best transfer function across a variety of sounds (e.g., sounds 1-n).

In general, a database of stimulation signals generated by pre-processing sound signals via various transfer functions such as shown in FIG. 18 can be useful for expediting the testing of such transfer functions for a particular user. Pre-processing such sounds allows for the processing to be done, for example, in a lab or on a workstation prior to any fitting process and allows for efficient application of stimulation signals corresponding to different transfer functions to a user's stimulator without requiring updates of the signal processor. Additionally, such pre-processing can allow for more advanced or computationally demanding processing techniques to be tested for efficacy even if such processing techniques may not yet be effectively implemented by an implanted signal processor (e.g., due to various hardware limitations). Testing the efficacy of such processing techniques can motivate evolution of processing methodologies and hardware capability, for example, in an effort to employ more complex processing techniques in the future.

Various features and functions of implantable systems have been described herein. As described, in various embodiments, system operation(s) can be adjusted based on communication with the implanted system from components located outside of the body while the system remains implanted. In some embodiments, the system may include any number of external components capable of interfacing with the system in a variety of ways.

Figure 19:
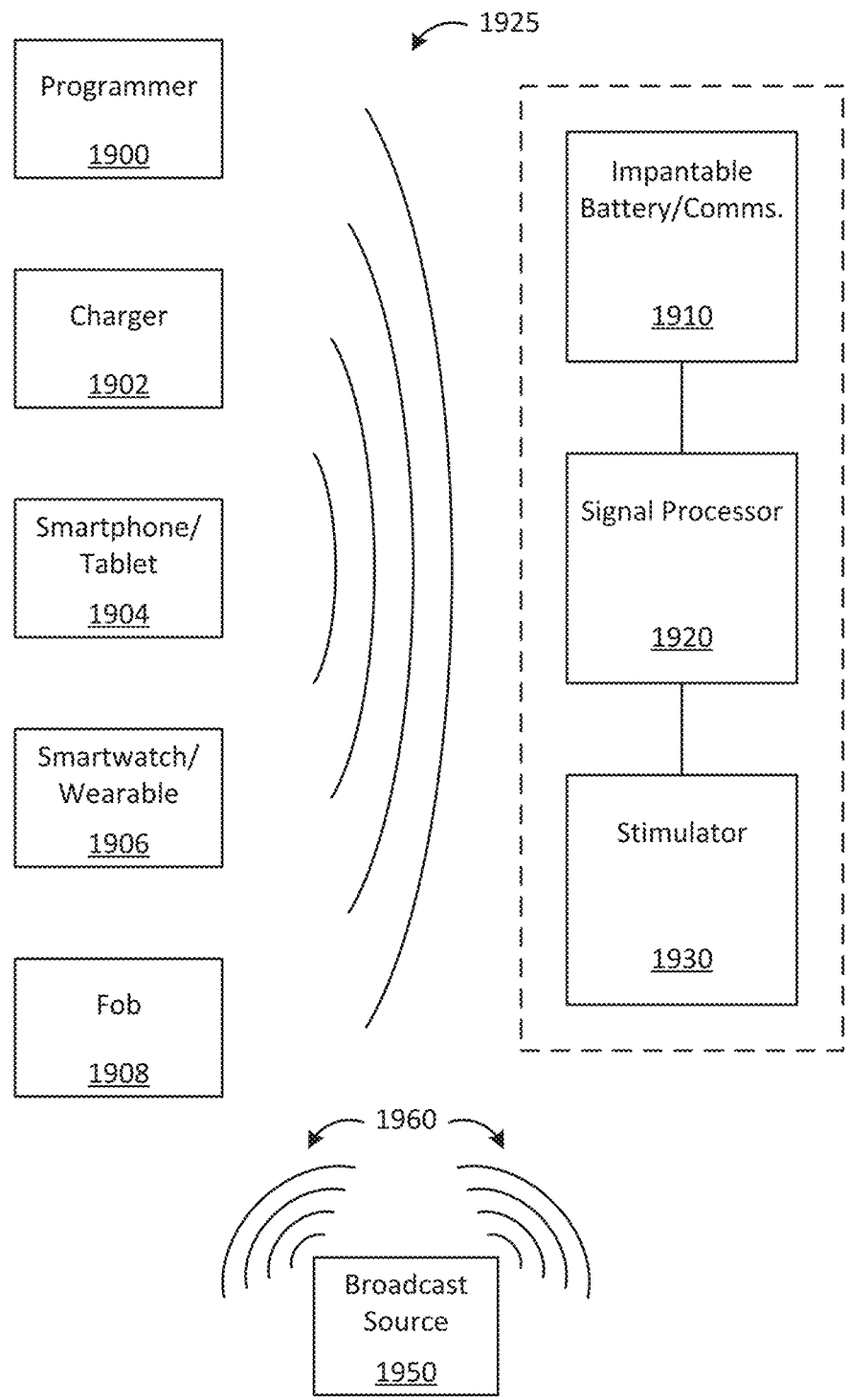
FIG. 19 is a schematic diagram illustrating possible communication between a variety of system components according to some embodiments of a fully-implantable system.

FIG. 19 is a schematic diagram illustrating possible communication between a variety of system components according to some embodiments of a fully implantable system. In the illustrated embodiment, implanted components (outlined in broken line) of a system include an implantable battery and/or communication module 1910, a signal processor 1920, and a stimulator 1930. Such implanted components can operate according to various examples as described herein in order to effectively stimulate a user (e.g., via electrical and/or acoustic stimulation) in response to received input signals.

The schematic illustration of FIG. 19 includes a plurality of external devices capable of wirelessly interfacing with one or more of the implanted components, for example, via communication link 1925. Such devices can include a programmer 1900, a charger 1902, a smartphone/tablet 1904, a smartwatch or other wearable technology 1906, and a fob 1908. In some examples, such components can communicate with one or more implantable components via one or more communication protocols via wireless communication link 1925, such as Bluetooth, Zigbee, or other appropriate protocols. In various embodiments, different external devices are capable of performing one or more functions associated with system operation. In some such embodiments, each external device is capable of performing the same functions as the others. In other examples, some external devices are capable of performing more functions than others.

For example, a programmer 1900 can be capable of interfacing wirelessly with one or more implantable components in order to control a variety of operating parameters of the implanted system. For example, in some embodiments, programmer 1900 can be configured to adjust a signal processor transfer function or select an operating profile (e.g., associated with a particular signal processor transfer function according to a particular user, environment, etc.). In some examples, the programmer 1900 can be used to establish user profiles, such as preferred signal processor transfer functions, as described elsewhere herein. The programmer 1900 can additionally or alternatively be used to turn the system on or off, adjust the volume of the system, receive and stream input data to the system (e.g., the implantable battery and/or communication module 1910). In some embodiments, the programmer 1900 includes a display for displaying various information to the user. For example, the display can be used to indicate a mode of operation (e.g., a loaded user profile), a remaining power level, or the like. In some such embodiments, the display can function as a user interface by which a user can adjust one or more parameters, such as volume, profile, input source, input mix, and the like.

In some embodiments, a charger 1902 can be used to charge one or more internal batteries or other power supplies within the system, such as in the implantable battery and/or communication module 1910. In some examples, the charger 1902 can include the same functionality as the programmer 1900, including, for instance, a display and/or user interface. In some such embodiments, the programmer 1900 and the charger 1902 can be integrated into a single device.

In some embodiments, various external devices such as a smartphone or tablet 1904 can include an application ("app") that can be used to interface with the implanted system. For example, in some embodiments, a user may communicate (e.g., via link 1925) with the system via the smartphone or tablet 1904 in order to adjust certain operating factors of the system using a predefined app to provide an interface (e.g., a visual interface via a display integrated into the external device). The app can assist the user in adjusting various parameters, such as volume, operating profile, on/off, or the like. In some examples, the smartphone/tablet 1904 can be used to stream input signals to the implanted system, such as media or communication playing on the smartphone/tablet 1904.

In some systems, a smartwatch or other wearable technology 1906 can interact with the system in a similar way as the smartphone/tablet 1904. For example, the smartwatch or other wearable technology 1906 can include an app similar to that operable on the smartphone/tablet to control operation of various aspects of the implanted system, such as volume control, on/off control, etc.

In some embodiments, the fob 1908 can be used to perform basic function with respect to the implanted system. For instance, in some embodiments, a fob 1908 can be used to load/implement a particular operating profile associated with the fob 1908. Additionally or alternatively, the fob 1908 can function similar to the shut-off controller 104 of FIG. 1 and can be used to quickly disable and/or mute the system. As described elsewhere herein, in some examples, the same device used to disable and/or mute the system (e.g., fob 1908) can be used to enable and/or unmute the system.

The schematic diagram of FIG. 19 further includes a broadcast source 1950 configured to broadcast signals 1960 that are receivable via one or more external devices and/or one or more implanted system components. Similar to the broadcast source 1550 in FIG. 15, broadcast source 1950 can be configured to emit signals that can be turned into stimulation signals for application by stimulator 1930. Broadcast signals 1960 can include, for example, telecoil signals, Bluetooth signals, or the like. In various embodiments, one or more external devices, such as a programmer 1900, charger 1902, smartphone/tablet 1904, smartwatch/wearable device 1906, and/or fob 1908 can include a component (e.g., a telecoil relay) capable of receiving broadcast signal 1960. The external device(s) can be further configured to communicate a signal to one or more implanted components representative of the received broadcast signal 1960 for applying stimulation to the patient based on the broadcast signal 1960.

Additionally or alternatively, in some embodiments, one or more implanted system components, such as an implantable battery and/or communication module 1910, a signal processor 1920, and/or a stimulator 1930 can be configured to receive broadcast signals 1960. Such component(s) can be used to generate stimulation signals for applying to a user via stimulator 1930 according to the received broadcast signals 1960.

As described, in some embodiments, various devices can communicate with components in an implanted system via wireless communication protocols such as Bluetooth. Various data and signals can be communicated wirelessly, including control signals and streaming audio. However, in some cases, such wireless communication should be made secure so that a system only communicates with those devices desired by the wearer. This can prevent unwanted signals from being broadcast to an implanted device and/or unauthorized access to one or more adjustable device settings.

In some embodiments, one or more implanted system components comprises a near field communication component configured to facilitate communication between the system and an external device only when brought into very close proximity to the near field communication component.

In some such examples, once near-field communication is established, the pairing for longer-range wireless communication (e.g., Bluetooth) can be established. For instance, in an exemplary embodiment, a charger and an implantable battery and/or communication module can each include near field communication components for establishing a secure, near field communication and subsequently pairing to each other for additional wireless communication.

Figure 20:
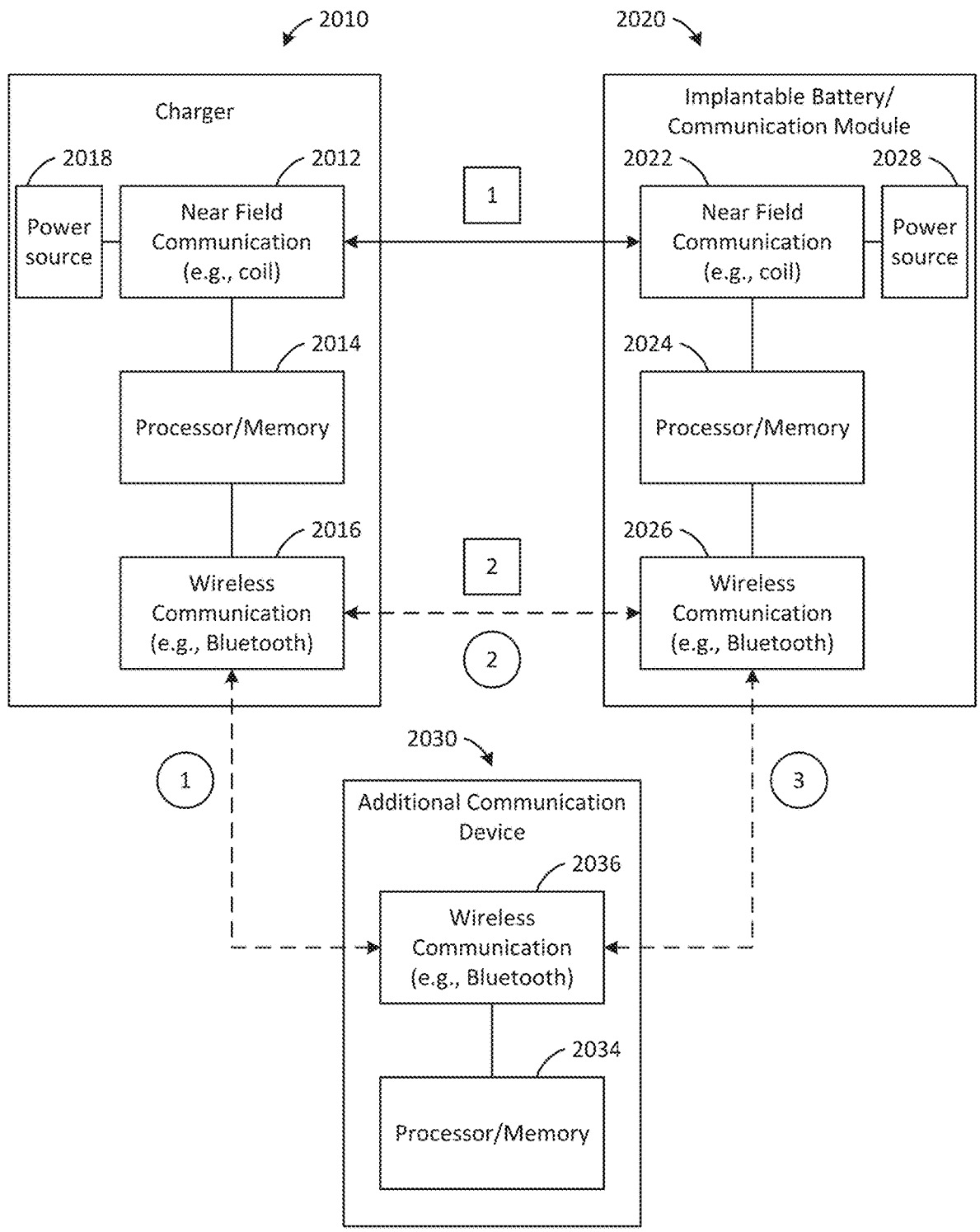
FIG. 20 is a schematic diagram showing establishing a secure wireless connection between various components in an implantable system.

FIG. 20 is a schematic diagram showing establishing a secure wireless connection between various components in an implantable system. In the illustrated example, a charger 2010 is configured to communicate with implantable battery and/or communication module 2020. Charger 2010 includes a wireless communication component 2016, such as a Bluetooth link, that can facilitate communication between the charger 2010 and other devices. Charger 2010 further includes a near field communication component 2012, such as a coil, and a processor/memory component 2014 that can receive signals from and communicate signals to near field communication component 2012 and/or wireless communication component 2016.

Implantable battery and/or communication module 2020 includes a wireless communication component 2026, such as a Bluetooth link, that can facilitate communication between the charger 2010 and other devices. Implantable battery and/or communication module 2020 further includes a near field communication component 2022, such as a coil, and a processor/memory component 2024 that can receive signals from and communicate signals to near field communication component 2022 and/or wireless communication component 2026.

In some embodiments, the near field communication components 2012 and 2022 comprise coils capable of establishing near field wireless communication therebetween. In some embodiments, the coils can also be used to transfer power between a power source 2018 of the charger 2010 to a power source 2028 of the implantable battery and/or communication module 2020, for example, to charge the power source 2028 in the implanted system for continued use. In various embodiments, power source 2018 and/or power source 2028 can include one or more batteries, capacitors (e.g., supercapacitors), and/or other power storage devices that can store and provide electrical energy to other components. In some embodiments, power source 2018 in charger 2010 can include an external or removable power source, such as a removable or replaceable battery and/or a power cord that can be plugged into a standard wall receptacle.

In some examples, implantable battery and/or communication module 2020 is unable to communicate with an external component via wireless communication component 2026 until such communication is first enabled. In such embodiments, enabling such communication is performed via near field communication component 2022 to ensure that devices are not accidentally or undesirably paired with the implantable battery and/or communication module 2020.

In the exemplary embodiment of FIG. 20, the numbers in square boxes illustrate an exemplary sequential process for establishing wireless communication between the charger 2010 and the implantable battery and/or communication module 2020. In the illustrated embodiment, charger 2010 first establishes contact with the implantable battery and/or communication module 2020 via near field communication components 2012, 2022. In various embodiments, such near field communication is only operation within very short distances, such as within two inches, for example. This prevents other devices from accidentally or undesirably establishing near field communication with implantable battery and/or communication module 2020. During execution of this step, a user may position the charger 2010 proximate their pectoral region in which the implantable battery and/or communication module 2020 is implanted to enable such communication. In some examples, after pairing the charger 2010 and implantable battery and/or communication module 2020 via near field communication 2012, 2022, such devices can subsequently communicate via wireless communication 2016, 2026.

In some embodiments, an external device 2030 (e.g., a smartphone or other audio/media source) can include a wireless communication component 2036 and processor/memory 2034 capable of facilitating communication with implantable battery and/or communication module 2020 (e.g., via wireless communication component 2026), but may not include a near field communication component for pairing the external device 2030. Thus, in some examples, the paired charger 2010 can be configured to enable subsequent pairing of the implantable battery and/or communication module 2020 with an external device 2030.

The circled reference numerals show an order of exemplary pairing of external device 2030 with an implantable battery and/or communication module 2020. The charger 2010 can communicate with the external device 2030 via wireless communication components 2016, 2036, for example, to determine that a user wishes to pair the external device 2030 with the implantable battery and/or communication module 2020. The charger 2010 can then communicate with the implantable battery and/or communication module 2020 (e.g., via wireless communication component 2016, 2026) to pair the implantable battery and/or communication module 2020 with the external device 2030 to enable subsequent wireless communication between implantable battery and/or communication module 2020 and the external device 2030 (e.g., via wireless communication component 2026, 2036).

In some examples, once a device is paired with the implantable battery and/or communication module 2020, it can be used to subsequently pair additional devices to the implantable battery and/or communication module as described above with respect to the charger 2010. In other embodiments, only some devices include the ability to pair additional devices with the implantable battery and/or communication module 2020, such as only the charger 2010. In still further examples, every device must be paired with the implantable battery and/or communication module via a near field communication process (e.g., via field communication component 2022) before longer range wireless (e.g., Bluetooth) communication can be established.

Additionally or alternatively, once an external device is paired with the implantable battery and/or communication module 2020, the external device (e.g. external device 2030) may be used to perform additional functions. In some embodiments, the additional functions may comprise adjusting a transfer function of the signal processor. In some examples, the external device includes or otherwise communicate with one or more sensors and can be configured to update the transfer function of the signal processor based on one or more signals detected via the one or more sensors. In some such examples, one or more such sensors can include a microphone, a location sensor (e.g. GPS, location based on one or more available wireless networks, etc.), a clock, or other sensors known to one of ordinary skill in the art. In some embodiments, external device (e.g., 2030) including or in communication with such one or more sensors includes a smartphone, tablet, or computer.

In embodiments wherein the external device includes, or is in communication with, a microphone, the external device can be configured to reprogram the signal processor based on information collected from the microphone representative of the acoustic environment. For example, the external device can be configured to identify background noise (e.g. low-end noise) and update the signal processor transfer function accordingly. In some such examples, the external device can be configured to reduce gain for low-end signals and/or emphasize other sounds or frequency ranges, such as speech or other sounds having a higher frequency. In some embodiments, a user can initiate the process of identifying background noise for adjusting the operation of the signal processor via the external device, for example, via a user interface (e.g., a smartphone or tablet touchscreen).

In embodiments in which the external device includes or is in communication with a location sensor and/or a clock, the external device may reprogram the signal processor based on a detected location and/or time. For instance, in an example embodiment, when the external device is located in a place known to be loud (e.g. a mall or sports stadium), the external device can be configured to detect the location and automatically reprogram the signal processor to reduce background noise (e.g., a particular frequency or range of frequencies) and/or reduce the overall gain associated with the transfer function. Similarly, in some examples, when located in a place in which a wearer may wish to particularly recognize speech (e.g., a movie theater) the external device can be configured to reprogram the signal processor to emphasize frequencies associated with speech.

In some examples, the transfer function can be updated to reduce a contribution of identified background noise. In some embodiments, reducing a contribution of identified background noise comprises emphasizing signals having frequency content between approximately 200 Hz and 20 kHz. In some such examples, updating the transfer function to reduce a contribution of the identified background noise comprises emphasizing signals having frequency content between approximately 300 Hz and 8 kHz. Emphasizing signals in such frequency ranges can help emphasize human speech or other similar signals within a noisy environment.

Additionally or alternatively, the external device can be configured to reprogram the signal processor based on a determined time of day. For example, at times when the wearer generally doesn't want to be bothered (e.g. at night), the external device can be configured to lower the volume of all or most sounds. In some examples, the wearer may additionally or alternatively temporarily reprogram the signal processor via the external device to adjust the transfer function of the signal processor (e.g., to reduce volume) for a predetermined amount of time (e.g. 15 minutes, 1 hour, or 1 day).

In some examples, reprogramming the signal processor comprises adjusting the transfer function to effect a relative change (e.g., reduce volume). In some cases, reprogramming the signal processor comprises implementing a predefined transfer function in response to received data, such as location data indicating the wearer is in a particular location. In some such examples, a plurality of pre-programmed transfer functions are stored in a memory and can be implemented based on data acquired via one or more sensors of the external device.

In some embodiments, the external device can be configured to provide an input signal based on audio generated by the external device. For example, the external device can be a smartphone, and can provide an input signal to a wearers implantable battery and/or communication module comprising audio from a phone call, text to speech audio (e.g. reading a text message or an article out loud), and/or media audio (e.g. videos, music, games, etc.). The implantable battery and/or communication module can be configured to relay the input signal to the signal processor for the signal processor to convert into corresponding stimulation signals.

Figure 21:
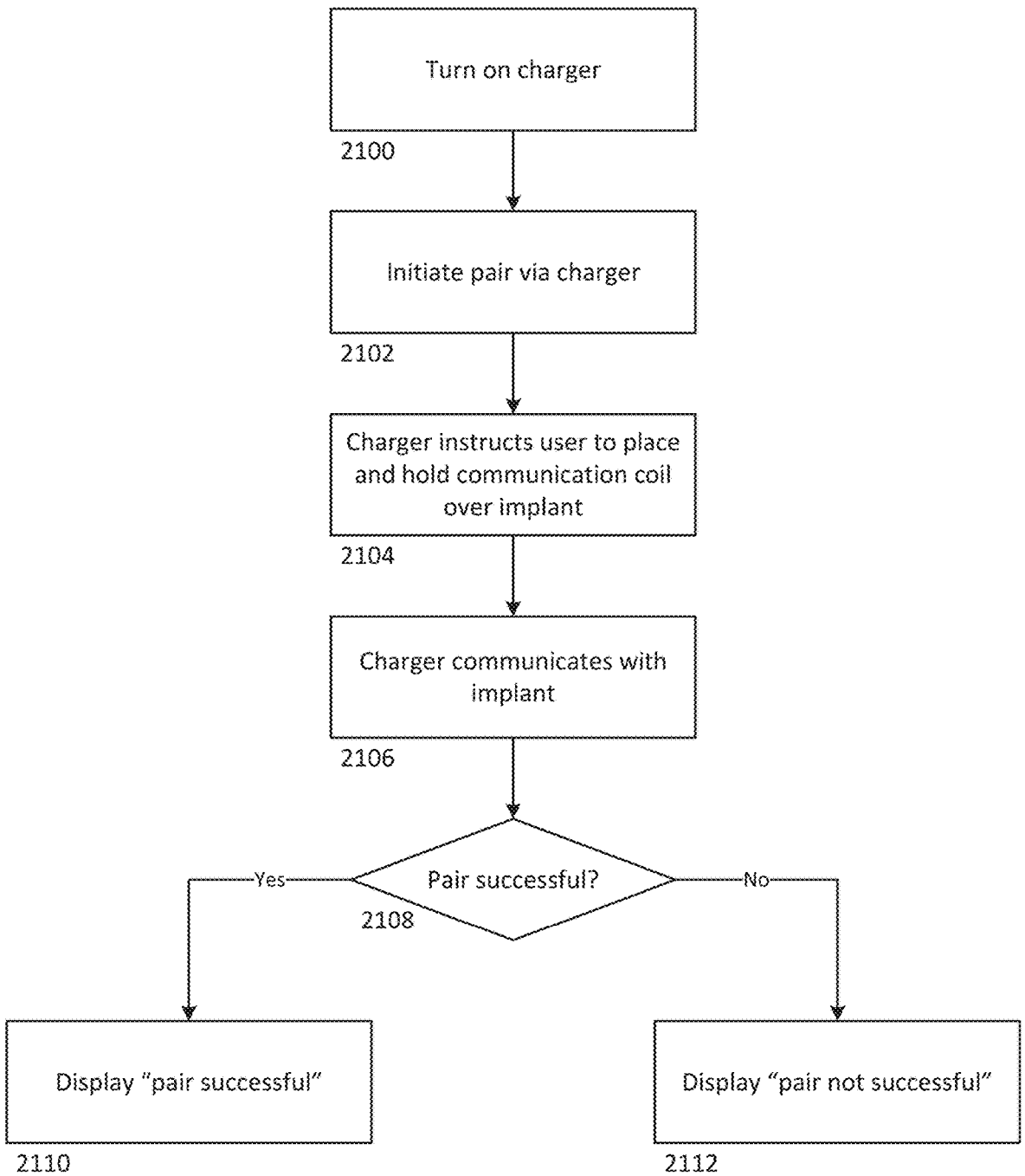
FIG. 21 shows a process flow diagram showing an exemplary method for pairing a charger with an implanted system.

FIG. 21 shows a process flow diagram showing an exemplary method for pairing a charger with an implanted system. The method includes turning on the charger (step 2100) and initiating a pairing process via the charger (step 2102). The charger may instruct the user to place and hold a communication coil associated with the charger over the implant (step 2104). When within range of coil communication, the charger communicates with the implant (step 2106), e.g., via an implantable battery and/or communication module. The charger can determine whether or not the pairing with the implant was successful (step 2108), and display to a user if the pairing was successful (step 2110) or not (step 2112).

Figure 22:
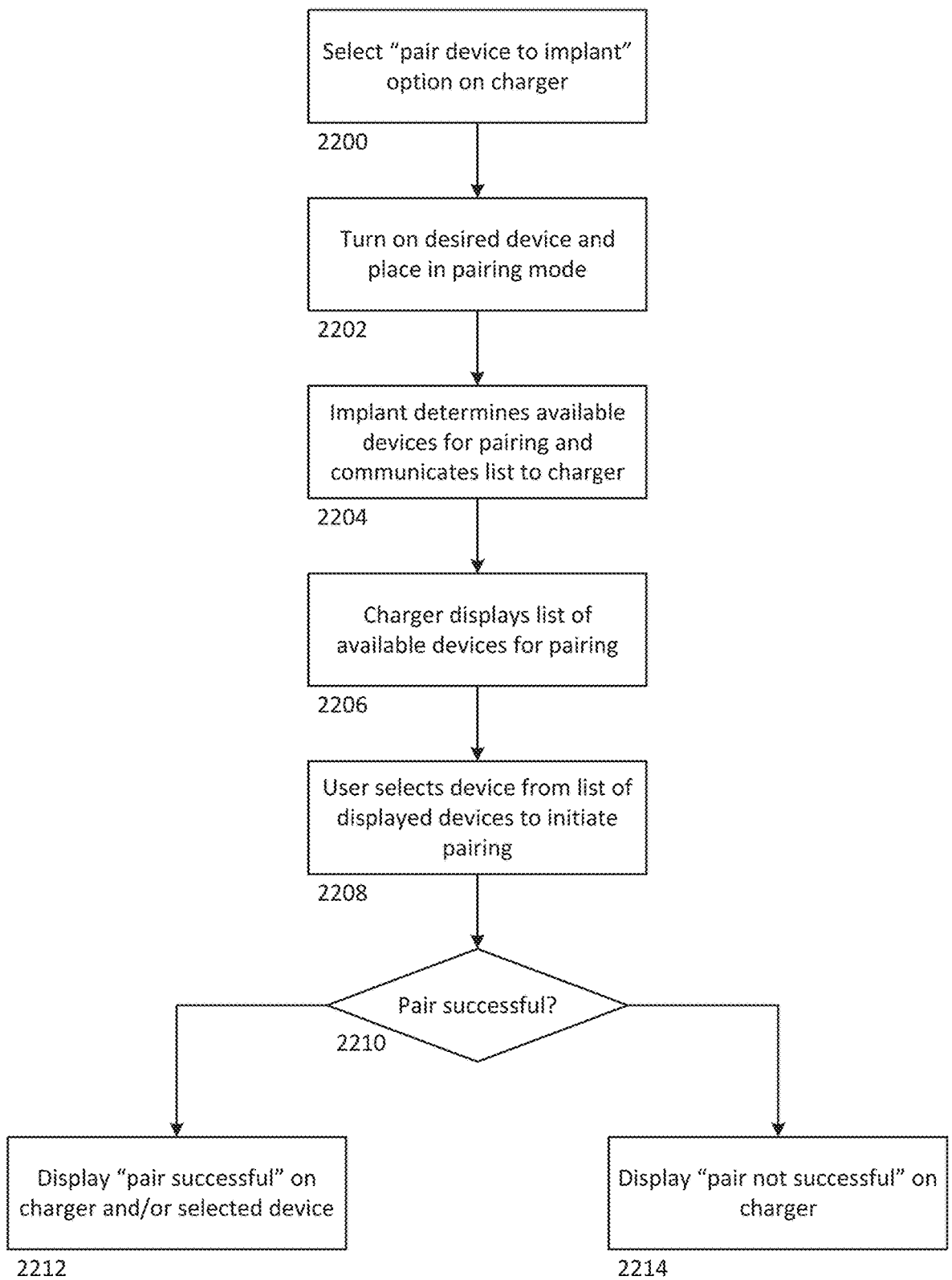
FIG. 22 shows a process flow diagram showing an exemplary method for pairing another device with an implanted system using a paired charger.

FIG. 22 shows a process flow diagram showing an exemplary method for pairing another device with an implanted system using a paired charger. The method includes selecting an option to pair a device to an implant on the charger (step 2200), turning on the desired device and placing it in a pairing mode (step 2202). The implant determines the devices available for pairing and communicates a list of available devices to the charger (step 2204), which displays the list of available devices to a user (step 2206). The user can select from a list of displayed devices to initiate the pairing (step 2208). The charger and/or selected device can determine if the pairing was successful step (step 2210). If the pairing is successful, a "pair successful" message can be displayed via the charger and/or the newly-paired device (step 2212). If the pair was unsuccessful, a "pair not successful" message can be displayed on the charger (step 2214). For example, in some embodiments, after attempting to initiate pairing between an implant (e.g., via the implantable battery and/or communication module of a system) and another device (e.g., step 2208), if, after a predetermined amount of time, the charger does not receive an indication confirming pairing from either the implant or the selected device, the charger may determine that the pair was unsuccessful, output the "pair not successful" message (step 2214), and stop attempting to establish the pairing.

In various examples, devices that can be paired to an implant (e.g., for communication with an implantable battery and/or communication module) via the charger such as via the method shown in FIG. 22 can include a remote, a smart device running an application for interfacing with the implant, a fob, an audio streaming device, or other consumer electronics capable of wireless communication (e.g., Bluetooth).

With reference back to FIG. 20, in various embodiments, once a device (e.g., charger 2010, external device 2030, etc.) has been paired with the implantable battery and/or communication module 2020 for wireless communication, information associated with the pairing (e.g., device identifiers, etc.) can be stored in one or more memory components (e.g., 2014, 2024, 2034) so that the pairing need not be performed again in the future. In some embodiments, one or more devices can be unpaired from communication with the implantable battery and/or communication module 2020. For instance, the device can be used to disconnect from the implantable battery and/or communication module 2020 if the device is no longer being used by the user (e.g., discarded, returned, given away, etc.). Additionally or alternatively, a device can be automatically unpaired if the device has not established wireless communication with the implantable battery and/or communication module 2020 within a certain amount of time since the last connection. For instance, in an exemplary embodiment, if a device transmitting a Bluetooth audio stream to an implanted system via the implantable battery and/or communication module becomes disconnected from the implantable battery and/or communication module for greater than 5 minutes, the device becomes unpaired from the implantable battery and/or communication module and must be re-paired for future use.

As described, in various embodiments, different external devices can interface with implanted components to adjust operation of the system in various ways. In some embodiments, not all components are capable of performing the same functions as other components. FIG. 23 is a chart showing the various parameters that are adjustable by each of a variety of external devices according to some exemplary systems. In the example of FIG. 23, entries in the chart including an 'X' represent a component configured to perform a corresponding function. For instance, in the illustrated embodiment, only the charger is capable of performing an initial wireless pairing with an implanted system, such as described with respect to FIGS. 20 and 21. In some such examples, the remaining devices that can be programmed for wireless communication with the implanted system are paired via the charger, such as described with respect to FIG. 22. Other examples are possible in which different components include different functionality than is represented by the example of FIG. 23, for instance, wherein components other than or in addition to the charger can initiate wireless pairing with the implanted system.

Generally, the modularity of such systems allows system modifications, such as repairing, replacing, upgrading, etc., of system components and/or transitioning from a partially- to fully-implantable system, to be performed with minimal disturbance of implanted system components. For example, an implanted cochlear electrode and electrical stimulator and/or acoustic stimulator can remain in place while other system components are implanted and/or replaced, reducing the risk of additional procedures damaging the patient's cochlear tissue. Additionally, the communication techniques as described herein can be used to help customize and/or optimize a signal processor transfer function for a particular patient, as well as enable the system to meet safety standards, provide adequate power and data transfer rates between system components, and operate at a high efficiency. It will be appreciated that, while generally described herein with respect to implantable hearing systems, communication techniques described can be used in a variety of other implantable systems, such as various neuromodulation devices/systems, including, for example, pain management, spinal cord stimulation, brain stimulation (e.g., deep brain stimulation), and the like.

Figure 24:
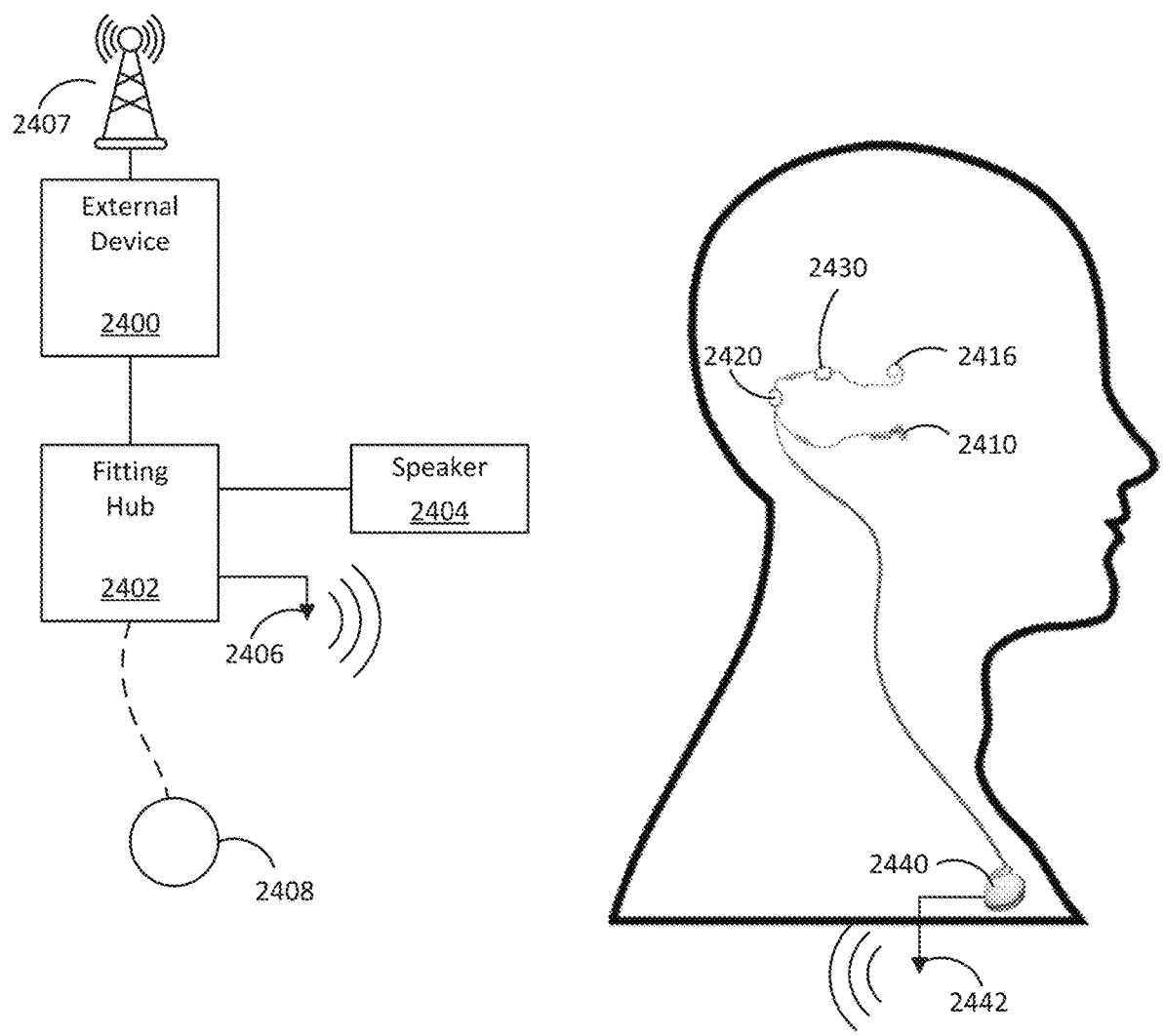
FIG. 24 shows an example configuration of an interfacing device configured to assist in system calibration.

In some embodiments, systems can communicate with external devices to assist in fitting and/or calibrating the implanted system. FIG. 24 shows an example configuration of an interfacing device configured to assist in system calibration. As shown, an external device 2400 (e.g., a laptop, PC, smartphone, tablet, smartwatch, etc.) communicates with a fitting hub 2402. The fitting hub 2402 includes or otherwise communicates with a speaker 2404, which can output a sound based on a command from the fitting hub 2402.

In the illustrated example, fitting hub 2402 includes a wireless communication interface 2406 (e.g., a Bluetooth interface) that can communicate with a communication interface 2442 of an implantable battery and/or communication module 2440. In some examples, the fitting hub 2402 includes or is otherwise capable of interfacing with a near field communication component 2408 (e.g., a communication coil) to enable Bluetooth communication between the fitting hub 2402 and an implanted system (e.g., via an implantable battery and/or communication module 2440) such as described elsewhere herein. Additionally or alternatively, another device (e.g., a charger) can be used to enable wireless (e.g., Bluetooth) communication between the fitting hub 2402 and the implantable battery and/or communication module 2440.

The illustrated system of FIG. 24 includes an implanted modular cochlear implant system including an implantable battery and/or communication module 2440, a signal processor 2420, a sensor 2410, a stimulator 2430, and a cochlear electrode 2416. Such components can be configured and arranged similar to various embodiments described herein and can configured to provide electrical signals from the stimulator 2430 via the cochlear electrode 2416 based on signals received at the signal processor from the sensor 2410.

During an exemplary calibration process, the fitting hub 2402 can be configured to output a sound via speaker 2404 and also communicate information about the sound (e.g., intensity, frequency content, etc.) to the implantable battery and/or communication module 2440 of the implanted system. The implanted system, e.g., via the signal processor 2420, can be configured to compare the output of the sensor 2410 (received at the signal processor 2420) to the actual sound emitted from the speaker 2404. This data can be repeated for a plurality of sounds from output from the speaker (e.g., various frequencies and/or amplitudes) and used to determine the relationships between sounds picked up from the sensor 2410 and the output from the sensor 2410 to the signal processor 2420. Based on this information, the signal processor 2420 transfer function can be calibrated so that stimulation signals sent to the stimulator 2430 based on the output from the sensor 2410 accurately represent the sound from the environment. Additionally or alternatively, the information can be used to identify how effectively the sensor responds to various external acoustic stimuli, such as different frequencies, intensities, etc. This information can be determined specifically for the wearer, since the sensor response may depend on various factors specific to the wearer and/or the positioning of the sensor.

In some embodiments, the fitting hub 2402 may be configured to output one or more sounds comprising a single frequency and/or single intensity. For example, each sound may have a signal frequency component at an intensity, such as various tones. Additionally or alternatively, the one or more sounds may comprise complex frequency and intensity components, such as sounds representing various beeps, words, noises, or other sounds known to one of ordinary skill in the art.

While described as taking place in the implanted system (e.g., the signal processor 2420), the calibration process can be similarly performed via the fitting hub 2402. For example, the speaker 2404 can output a sound based on instructions from the fitting hub 2402. The sensor 2410 can output a signal based on the sensor response to the sound emitted from speaker 2404, and the signal processor 2420 can receive the signal from the sensor 2410 and output stimulation signals to the stimulator 2430 based on the receives signals and the signal processor transfer function.

In various examples, the implantable battery and/or communication module 2440 can be configured to receive any combination of the signals from the sensor 2410, the stimulation signals from the signal processor 2420, or signals representative of one or both of such signals. The implantable battery and/or communication module 2440 can then communicate one or more signals to the fitting hub 2402 representative of the output of the sensor 2410 and/or the signal processor 2420 in response to the sound output from speaker 2404. The comparison of the sound output from the speaker 2404 and the corresponding resulting signal(s) in the implanted system can be performed via processing in the fitting hub 2402. Similar to discussed above, this comparison can be used to determine the relationships between sounds picked up from the sensor 2410 and the output from the sensor 2410 to the signal processor 2420. Based on this information, the signal processor 2420 transfer function can be calibrated so that stimulation signals sent to the stimulator 2430 based on the output from the sensor 2410 accurately represent the sound from the environment. Additionally or alternatively, the information can be used to identify how effectively the sensor responds to various external acoustic stimuli, such as different frequencies, intensities, etc. This information can be determined specifically for the wearer, since the sensor response may depend on various factors specific to the wearer and/or the positioning of the sensor.

As described, in various examples, the external device 2400 can be used in conjunction with the fitting hub 2402. For instance, in some examples, the external device 2400 can provide processing and control capabilities for processes described herein, and the fitting hub 2402 can act as the interface between the external device 2400 and the implanted system (e.g., by providing speaker 2404, wireless communication interface 2406, near field communication component 2408, etc.).

In some embodiments, features and/or functions of the fitting hub 2402 as described herein can be performed via the external device, such as via a laptop, PC, smartphone, tablet, etc. including various capabilities described with respect to the fitting hub. For instance, an external device can include a speaker capable of outputting desired sounds according to a command from the external device, as well as a wireless communication interface for communicating with the implanted system, e.g., via implantable battery and/or communication module 2440.

In some examples, the external device 2400 and/or the fitting hub 2402 may comprise a user interface in the form of an application on the external device. In such embodiments, features and/or functions of the fitting hub 2402 can be performed via the application. For instance, in some examples, the fitting hub can receive instructions to perform functions via an application running on the external device 2400. In some such embodiments, a wearer and/or physician can provide an input via the application, for example, during various processes described herein. In some embodiments, a wearer can receive a sound from the fitting hub 2402 and provide input, via the application, indicating whether the sound was heard or not heard, was too loud or too quiet, was distinguishable or not distinguishable from a previous sound, and/or other inputs. In some examples, an implant system (e.g., via fitting hub 2402 or implantable battery and/or communication module 2440) can be configured to update a signal processor transfer function in response to such received inputs.

In some embodiments, the fitting hub 2402 and/or the external device 2400 may be configured to communicate to a remote facility, for example, with a physician such as an audiologist. In some such embodiments, the fitting hub 2402 and/or the external device 2400 includes a remote communication device 2407 configured to communicate with such a remote facility, for example, via the internet. The remote communication device 2407 can communicate various information associated with the fitting hub 2402, the external device 2400, and the implanted cochlear implants, to an additional device, such as a device used by an audiologist. Additionally or alternatively, the remote communication device 2407 can be configured to receive inputs from such an additional device, such as inputs related to features and/or functions performed by the fitting hub, the external device, and/or the implanted cochlear implants. For example, in some instances, an audiologist operating at a remote facility can trigger the fitting hub 2402 to output one or more predetermined sounds and/or perform one or more fitting functions. Additionally or alternatively, the audiologist can receive information such as how often the wearer uses and/or updates features of the cochlear implant system.

In an example implementation, a physician can receive diagnostic information regarding any testing or other processes performed by the external device 2400, the fitting hub 2402, and/or the implanted cochlear implant system via the remote communication device 2407. In some such examples, the physician may receive data regarding how often tests or other processes are performed, the results of any performed tests or processes, how often various devices (e.g. fitting hub 2402) are used, and/or any feedback regarding the use or usability of the implanted cochlear implants.

In some examples, the physician can initiate or perform various tests or other processes from an additional device via the remote communication device 2407. In some embodiments, features and/or functions of the fitting hub 2402 as described herein can be performed or initiated by a physician using an additional device via the remote communication device 2407. In various examples, the physician can perform various features, such as providing one or more sounds via a speaker (e.g., 2404), performing a stapedial reflex test, or the like as described herein. The physician can receive one or more signals representative of the output of the sensor 2410 and/or the signal processor 2420 in response to the provided one or more sounds from the speaker. A comparison of the provided one or more sounds form the speaker and the corresponding resulting signal(s) in the implanted system can be performed by the additional device and/or by the physician receiving such information via the additional device.

In some embodiments, the remote communication device 2407 may communicate with an additional device (e.g., at a physician's remote facility) via a wireless connection (e.g. Bluetooth, Wi-Fi, NFC, cellular network, internet access, etc.). While the remote communication device 2407 is depicted as communicating via the external device 2400, the remote communication device 2407 can additionally or alternatively communicate via the fitting hub 2402, or a different component of the system. In various embodiments, such a remote communication device can be integrated into the external device 2400 and/or the fitting hub 2402. In some embodiments, the remote communication device 2407 and the wireless communication interface 2406 may be integrated together to facilitate communication with a remote facility and an implanted system. Alternatively, the remote communication device 2407 and the wireless communication interface 2406 may be separate, or partially separate components.

Figure 25:
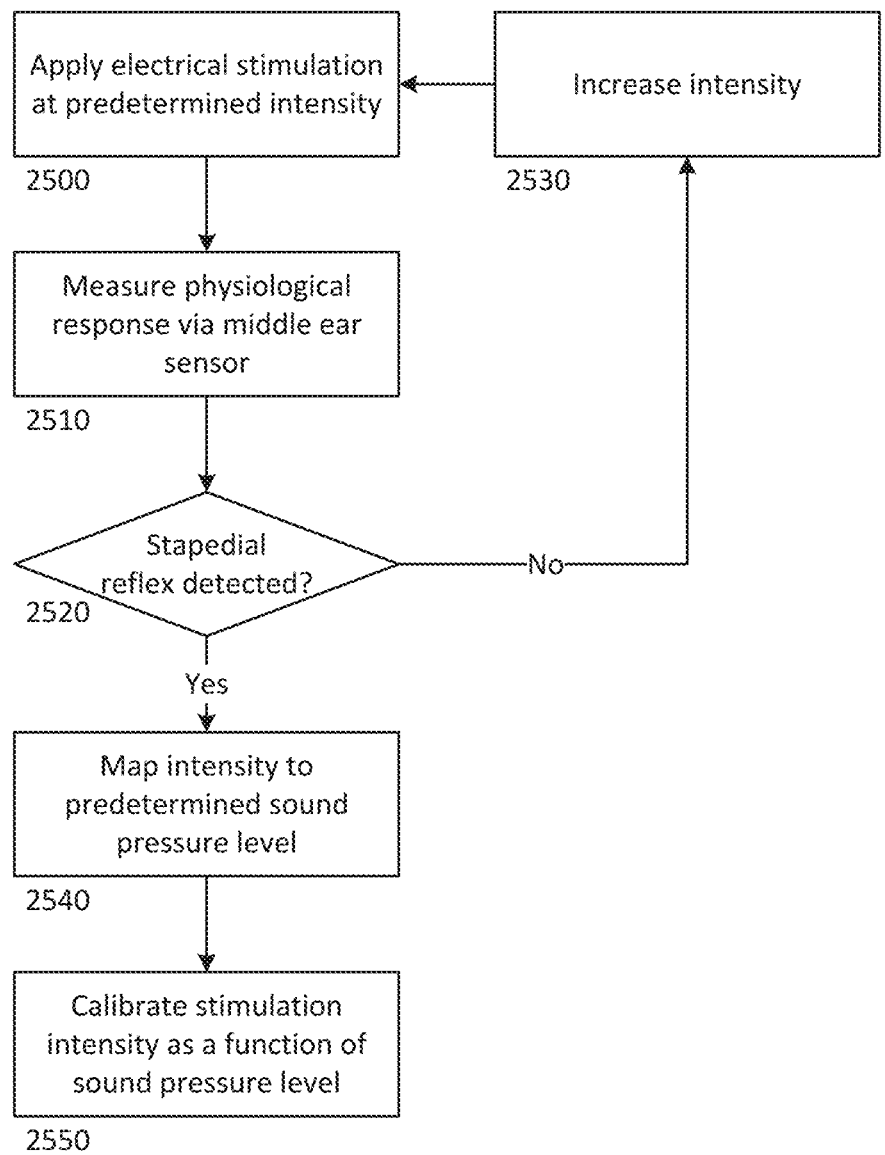
FIG. 25 is a process flow diagram showing an example process for calibrating an implanted system.

FIG. 25 is a process flow diagram showing an example process for calibrating an implanted system. In some examples, one or more sensors (e.g., a sensor contacting the incus such as sensor 540 shown in FIG. 5) can detect a physiological phenomenon known as a stapedial reflex, in which muscles in the middle ear contract in response to various stimuli, such as loud sounds or the expectation of loud sounds. In some examples, an implanted signal processor in communication with such a sensor can recognize the occurrence of a stapedial reflex based on a characteristic output, for instance, via preprogrammed signal recognition or via a learning process, in which the stapedial reflex is triggered and the response from the sensor is measured and learned.

The calibration process of FIG. 25 includes applying electrical stimulation at a predetermined intensity (step 2500) and measuring a physiological response via a middle ear sensor (step 2510). The measured physiological response can be used to detect whether or not a stapedial reflex has occurred (step 2520). If a stapedial reflex is not detected, the intensity of the electrical stimulation is increased (step 2530), and electrical stimulation at the new intensity is applied (step 2500) and the physiological response is measured (step 2510). This process can be repeated until the stapedial reflex is detected at step 2520.

Once the stapedial reflex is detected, the intensity that caused the stapedial reflex can be mapped to a predetermined sound pressure level (step 2540). For instance, in some examples, the lowest electrical intensity determined to cause the detected stapedial reflex can be mapped to an input sound pressure of 100 dB. The method can include calibrating stimulation intensities as a function of sound pressure level (step 2550) based on the mapping of the stapedial reflex-causing intensity to the predetermined sound pressure level.

The calibration process of FIG. 25 can be initiated in a variety of ways. For example, in various embodiments, the process can be initiated by one or more components in communication with the implanted system, such as a programmer, charger, external device, fitting hub, or the like. Such processes can be performed during an initial fitting and/or a calibration after a period of use of the system.

Leveraging fully implanted system and initiating the process via a wireless communication (e.g., from a programmer, fitting hub, external device etc.), greatly simplifies the process of triggering and/or detecting the stapedial reflex. For example, utilizing a cochlear electrode (e.g., 2416) to cause the stapedial reflex and sensing the reflex using an implanted middle ear sensor eliminates the need for tedious diagnostic equipment such as tympanometry equipment for analyzing a stapedial reflex.

In some examples, the systems and processes described with respect to FIG. 24 can be used in the calibration steps discussed with respect to FIG. 25. For instance, in an illustrative example, the fitting hub 2402 of FIG. 24 can cause a speaker 2404 to produce a sound having a sound pressure level of 100 dB while also communicating (e.g., via Bluetooth communication) the details of the sound (e.g., intensity, frequency, etc.) to the implantable battery and/or communication module 2440. The output of the sensor 2410 in response to the 100 dB sound can be identified and associated with the lowest electrical stimulation intensity that causes the detected stapedial reflex. Such a process can be repeated for a plurality of frequencies to link various external acoustic stimuli (e.g., from speaker 2404) to particular electrical stimulations.

Several embodiments discussed herein generally relate to a cochlear implant system. As discussed herein, cochlear implant systems can comprise a cochlear electrode implanted into the cochlear tissues of a wearer, as well as various other components such as an electrical stimulator, signal processor, and a middle ear sensor. In some embodiments, the cochlear implant system comprises components implanted into one or both sides of a wearer. For example, a system can comprise components implanted in a wearer's left side (e.g. for their left ear), their right side (e.g. for their right ear), or both.

Figure 26:
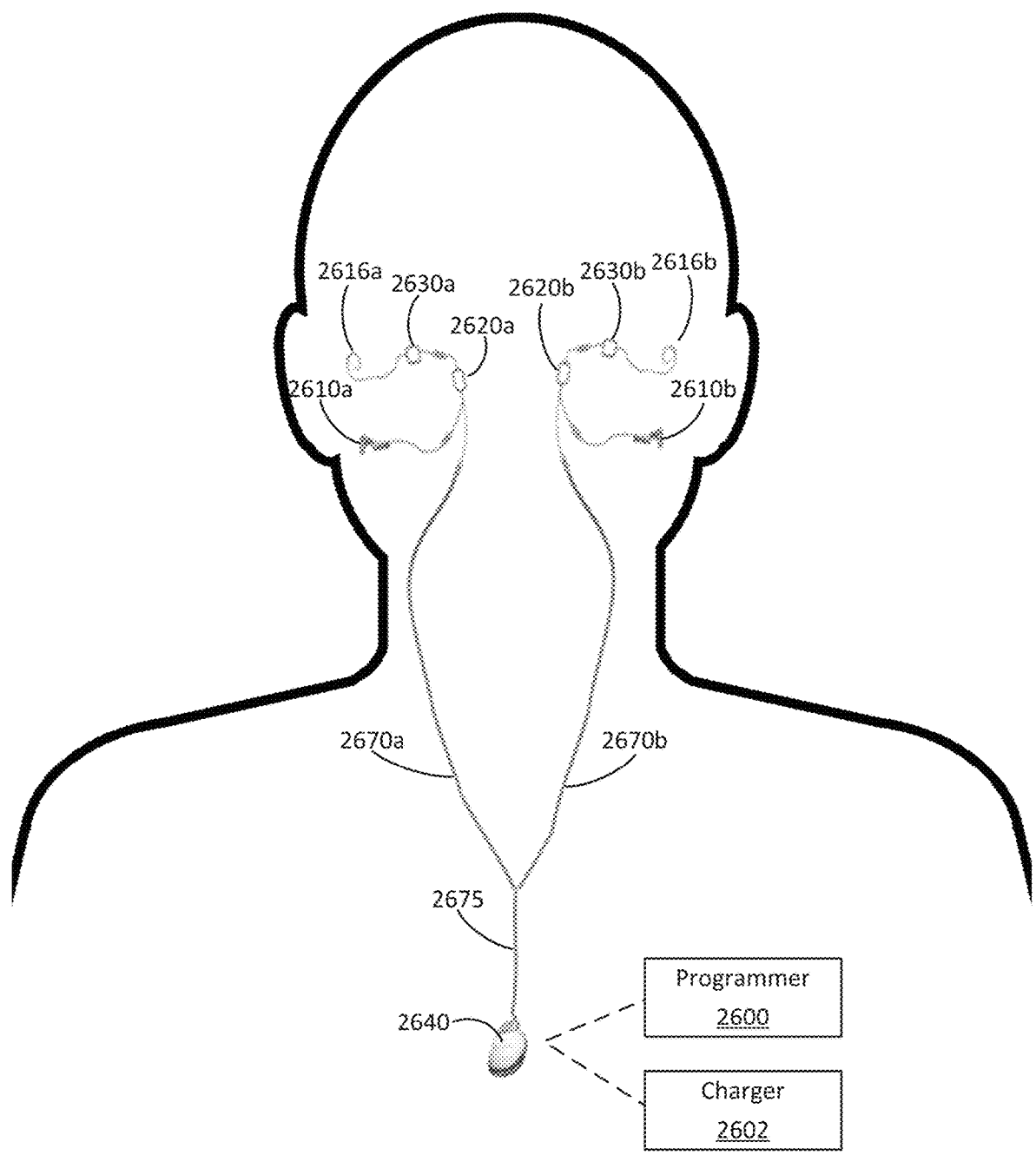
FIG. 26 shows an example embodiment wherein the cochlear implant system comprises components implanted for both sides of the wearer (e.g. for both their right ear and their left ear

FIG. 26 shows an example embodiment wherein the cochlear implant system comprises components implanted for both sides of the wearer (e.g. for both their right ear and their left ear). As shown, the cochlear implant system of FIG. 26 comprises a first subsystem comprising a first cochlear electrode 2616*a*, a first electrical stimulator 2630*a*, a first middle ear sensor 2610*a*, and a first signal processor 2620*a*, and a second subsystem comprising a second cochlear electrode 2616*b*, a second electrical stimulator 2630*b*, a second middle ear sensor 2610*b*, and a second signal processor 2620*b*. The first subsystem and the second subsystem can be configured similarly to other cochlear implant systems discussed herein. In some embodiments, the first electrical stimulator 2630*a* and the first signal processor 2620*a* can be housed in a first housing with the first cochlear electrode 2616*a* extending from the first housing. Additionally or alternatively, the second electrical stimulator 2630*b* and the second signal processor 2620*b* can be housed in a second housing with the second cochlear electrode 2616*b* extending from the second housing.

The cochlear implant system of FIG. 26 comprises an implantable battery and/or communication module 2640. In some embodiments, the cochlear implant system can comprise a plurality of implantable battery and/or communication modules, even though not shown in FIG. 26. The implantable battery and/or communication module 2640 can be configured to adjust a first transfer function associated with the first signal processor 2620*a* and adjust a second transfer function associated with the second signal processor 2620*b*.

In some such embodiments, the implantable battery and/or communication module 2640 can be in communication with the first signal processor 2620*a* via a first lead 2670*a* and be in communication with the second signal processor 2620*b* via a second lead 2670*b*. In some such embodiments, such as shown in FIG. 26, the first lead 2670*a* may be different than second lead 2670*b*.

Additionally or alternatively, the implantable battery and/or communication module 2640 can be in communication with both the first signal processor 2620*a* and the second signal processor 2620*b* via a bifurcated lead 2675. In some such examples, the implantable battery and/or communication module 2640 can be configured to simultaneously send an output signal to each of the first signal processor 2620*a* and the second signal processor 2620*b* via the bifurcated lead 2675. In some embodiments, the implantable battery and/or communication module 2640 provides the same output signal to both the first signal processor 2620*a* and the second signal processor 2620*b*. The implantable battery and/or communication module 2640 can be configured to communicate addressed output signals to the first signal processor 2620*a* and the second signal processor 2620*b* via the bifurcated lead 2675, wherein the addressed output signals comprises address information designating at least one of the first signal processor 2620*a* and the second signal processor 2620*b*. In some such embodiments, first signal processor 2620*a* and second signal processor 2620*b* can be configured to detect the address information and respond only to signal addressing the particular signal processor. For instance, in some examples, the first signal processor 2620*a* may be unaffected by an addressed output signal comprising address information designating the second signal processor 2620*b* and not the first signal processor 2620*a*. Similarly, the second signal processor 2620*b* may be unaffected by an addressed output signal comprising address information designating the first signal processor 2620*a* and not the second signal processor 2620*b*. Alternatively, the battery and/or communication module 2640 may communicate either the same signal or a different signal to first signal processor 2620*a* and second signal processor 2620*b* without bifurcated lead 2675, such as an embodiment having two separate outputs from the battery and/or communication module 2640.

As discussed herein, an implantable battery and/or communication module can be configured to communicate with a signal processor to adjust a transfer function associated therewith. In some examples, the implantable battery and/or communication module 2640 can be configured to adjust the first transfer function for the first signal processor 2620*a*, the second transfer function for the second signal processor 2620*b*, or a combination of the two, for example, in response to a received command. In such embodiments, the implantable battery and/or communication module 2640 may be configured to receive the commands from the external device via a wireless communication interface (e.g. Bluetooth, Wi-Fi, NFC, etc.).

In some embodiments, the cochlear implant system can receive a command to change a volume associated with the cochlear implant system. In some embodiments, the volume associated with the cochlear implant system may be an overall volume or a volume of a specific range of frequencies and/or tones (e.g. reduction of background noise, emphasis of speech, an increase of volume from one source relative to another, etc.). In some examples, the implantable battery and/or communication module 2640 can be configured to, in response to a command to change the volume, adjust a relative volume of both the first transfer function and the second transfer function by approximately the same amount.

However, in some examples, a wearer may have different amounts or types of hearing loss on one side vs the other. In such examples, increasing the volume of the first transfer function the same as the second transfer function may not correlate to a patient perceiving the same relative volume change on both sides. As such, the first transfer function and the second transfer function may be updated such that the patient perceives a similar change in output via the first electrical stimulator 2630*a* and the second electrical stimulator 2630*b* in response to a given stimulus.

In response to the command to change the volume, the implantable battery and/or communication module 2640 can be configured to determine an existing first transfer function associated with the first signal processor 2620*a* and determine an updated first transfer function based on the determined existing first transfer function and the received command. Additionally, the implantable battery and/or communication module 2640 can be configured to determine an existing second transfer function associated with the second signal processor 2620*b* and determine an updated second transfer function based on the determined existing second transfer function and the received command. In such embodiments, the updated first transfer function and the updated second transfer function may reflect a change in perceived volume as prescribed in the received command. However, the changes to the first transfer function and the second transfer function need not be the same, despite resulting from the same received command.

For instance, in some embodiments, in response to a command to change a volume, the implantable battery and/or communication module can be configured to individually change a volume associated with the first transfer function and a volume associated with the second transfer function. In some such embodiments, the adjustment to the first transfer function may reflect the same or a different adjustment than the adjustment to the second transfer function. In an example embodiment, in response to receiving a command to change the volume, the implantable battery and/or communication module can be configured to adjust the volume of the first transfer function by more or less than the second transfer function, such that a wearer perceives more or less change in the stimulation output via the first electrical stimulator 2630a than the second electrical stimulator 2630b.

Transfer functions associated with separate signal processors can be updated differently in response to a common command (e.g., "increase volume") in order to accommodate for different hearing profiles associated with each subsystem. For instance, in an example embodiment, a first subsystem and a second subsystem can be programmed with different transfer functions based on, for example, the wearer's hearing profile in the left and right ears, the operation of a middle ear sensor in each of the first and second subsystems (which might behave differently based on, for example, a wearer's anatomy), and the like. A command to "increase volume" might result in different adjustments to the different transfer functions. For example, a first transfer function might increase a gain by 10% while the second transfer function might increase a gain by 20% in one or more frequency ranges. Each change can be determined, for example, based on a prescribed response to a given command based on an existing transfer function.

In some embodiments, systems including two different subsystems, such as shown in FIG. 26, can be used to perform various functions described herein, such as detecting a stapedial reflex in a wearer. In an example embodiment, an acoustic stimulus can be provided to a first ear of the wearer, such as via an in-ear speaker (e.g., in communication with a fitting hub). The acoustic stimulus can be detected via first middle ear sensor 2610, which can provide an input signal to the first signal processor 2620a programmed with a first transfer function and output a corresponding stimulation signal to the first electrical stimulator 2630a. The first electrical stimulator 2630a can provide an electrical stimulus to the wearer's cochlear tissue based on the stimulation signal.

The implantable battery and/or communication module 2640 can receive information from the second signal processor 2620b representing data received from the second middle ear sensor 2610b. Generally, a stapedial reflex occurs in the inner ear of both sides of a person, even if the stimulus is applied to only a single ear. Accordingly, the implantable battery and/or communication module 2640 can be configured to detect a stapedial reflex triggered in the wearer based on the information received from the second signal processor 2620b in response to the stimulus detected by the first middle ear sensor 2610a.

In some embodiments, this phenomenon can be leveraged in order to perform various stapedial reflex processes described herein. For example, a fitting hub can provide a stimulus of increasing intensity to a first ear of a wearer until the implantable battery and/or communication module detects a stapedial reflex in the other ear of the wearer. Similar to described elsewhere herein, the intensity the sound that triggered the stapedial reflex can be used to calibrate the transfer function of the signal processor associated with the sensor used in the first ear. Such a process can be repeated for a plurality of frequencies and for the other ear.

Various non-limiting embodiments have been described. These and others are within the scope of the following enumerated embodiments.

The invention claimed is:

1. A method of compensating for variability in a middle ear sensor comprising:
   applying a plurality of stimulus signals to a middle ear sensor, the plurality of stimulus signals having known frequency content and including a corresponding plurality of frequencies or frequency ranges;
   for each of the plurality of stimulus signals:
      receiving the stimulus signal via a middle ear sensor,
      generating, with the middle ear sensor, an input signal based on the stimulus signal;
      applying an analog filter to the generated input signal to generate an analog filtered signal;
      applying a digital filter to the generated analog filtered signal to generate a digitally filtered signal corresponding to the stimulus signal; and
      measuring a frequency response of the digitally filtered signal with respect to the corresponding stimulus signal, the measuring the frequency response of the digitally filtered signal with respect to the corresponding stimulus signal comprising determining a ratio of a magnitude of the digitally filtered signal to a magnitude of the corresponding stimulus signal; and
   adjusting the digital filter to normalize the frequency response of the digitally filtered signals with respect to the stimulus signals across the plurality of frequencies or frequency ranges.

2. The method of claim 1, wherein the applying the plurality of stimulus signals comprises applying stimulus signals having frequencies ranging between 100 Hz and 10 kHz.

3. The method of claim 1, wherein adjusting the digital filter to normalize the frequency response of the digitally filtered signals with respect to the stimulus signals comprises adjusting the digital filter so that the determined ratio is approximately equal for each of the plurality of frequencies or frequency ranges.

4. The method of claim 1, wherein applying the analog filter to the generated input signals comprises applying a plurality of analog filters and/or analog amplifiers.

5. The method of claim 4, further comprising adjusting the analog filter to normalize the frequency response of the digitally filtered signals with respect to the stimulus signals.

6. The method of claim 1, further comprising applying a transfer function to the digitally filtered signals to generate stimulation signals.

7. The method of claim 6, further comprising adjusting the transfer function using an external wireless communication device via a wireless communication protocol.

8. The method of claim 7, wherein adjusting the transfer function comprises using the external wireless communication device to collect auditory data representative of a surrounding environment.

9. The method of claim 8, further comprising:
   identifying background noise in the collected auditory data of the external wireless communication device; and
   updating the transfer function to reduce a contribution of the identified background noise in the stimulus signals.

10. The method of claim 9, wherein updating the transfer function to reduce the contribution of the identified background noise comprises emphasizing signals having frequency content between approximately 200 Hz and 20 kHz.

11. The method of claim 10, wherein updating the transfer function to reduce the contribution of the identified background noise comprises emphasizing signals having frequency content between approximately 300 Hz and 8 kHz.

12. The method of claim 9, wherein updating the transfer function to reduce a contribution of identified background noise comprises emphasizing frequencies associated with human speech.

13. The method of claim 6, further comprising:
receiving information from a fitting hub regarding a sound output from a speaker of the fitting hub;
receiving input signals generated via the middle ear sensor in response to the sound output from the speaker; and
analyzing the information received from the fitting hub regarding the sound output from the speaker and the input signals from the middle ear sensor in response to the sound output from the speaker to determine a relationship between the sound output from the speaker of the fitting hub and the resulting input signals generated via the middle ear sensor in response to the sound output from the speaker.

14. The method of claim 13, further comprising updating the transfer function in response to the determined relationship.

15. The method of claim 6, further comprising providing an electrical signal to a cochlear electrode based on the stimulation signals.

16. The method of claim 15, wherein
applying the transfer function to the digitally filtered signals is performed by a signal processor;
providing the electrical signal to the cochlear electrode is performed by a stimulator; and
the signal processor and the stimulator are located in a single housing.

* * * * *